(12) United States Patent
Zuker et al.

(10) Patent No.: US 7,939,279 B2
(45) Date of Patent: *May 10, 2011

(54) MAMMALIAN T1R3 SWEET TASTE RECEPTORS

(75) Inventors: Charles S Zuker, San Diego, CA (US); Nicholas J. P. Ryba, Bethesda, MD (US); Isolde Erlenbach, Bethesda, MD (US); Grace Q Zhao, Los Angeles, CA (US)

(73) Assignees: The Regents of the University of California, Oakland, CA (US); The Department of Health and Human Services, Rockland, MD (US)

( * ) Notice: Subject to any disclaimer, the term of this patent is extended or adjusted under 35 U.S.C. 154(b) by 34 days.

This patent is subject to a terminal disclaimer.

(21) Appl. No.: 12/257,290

(22) Filed: Oct. 23, 2008

(65) Prior Publication Data

US 2009/0155819 A1    Jun. 18, 2009

Related U.S. Application Data

(60) Continuation of application No. 11/402,202, filed on Apr. 10, 2006, now Pat. No. 7,459,277, which is a division of application No. 10/679,102, filed on Oct. 2, 2003, now abandoned.

(51) Int. Cl.
*G01N 33/566* (2006.01)
*C07K 14/705* (2006.01)

(52) U.S. Cl. .......... 435/7.21; 435/7.1; 435/7.2; 436/501

(58) Field of Classification Search .................. None
See application file for complete search history.

(56) References Cited

U.S. PATENT DOCUMENTS

| 7,402,400 | B2 | 7/2008 | Zuker et al. |
| 2002/0160424 | A1 | 10/2002 | Adler et al. |

FOREIGN PATENT DOCUMENTS

| CA | 2451317 | 1/2003 |
| EP | 1270724 A2 | 1/2003 |
| WO | WO 00/06593 A1 | 2/2000 |
| WO | WO 01/64882 A2 | 9/2001 |
| WO | WO 01/66563 A2 | 9/2001 |
| WO | WO 01/83749 A2 | 11/2001 |
| WO | WO 02/064631 A2 | 8/2002 |
| WO | WO 02/086079 A | 10/2002 |
| WO | WO 03/001876 A2 | 1/2003 |
| WO | WO 03/025137 A2 | 3/2003 |

OTHER PUBLICATIONS

Ariyasu, T. et al., "Taste Receptor TIR3 is an Essential Molecule for the Cellular Recognition of the Disaccharide Trehalose," In Vitro Cellular & Developmental Biology, Jan. and Feb. 2003, pp. 80-88, vol. 39, No. 1/2.
Bachmanov, A. A. et al., "Positional Cloning of the Mouse Saccharin Preference (SAC) Locus," Chemical Senses, Sep. 2001, pp. 925-933, vol. 26, No. 26, IRL Press, Oxford, GB.
European Communication Pursuant to Article 96(2) EPC, EP 04794142.2, May 15, 2007, 4 pages.
European Examination Report, European Application No. 02749804.7, Feb. 23, 2009, 9 pages.
European Supplementary Search Report, European Application No. 02749804.7, Jul. 11, 2007, 8 pages.
European Supplementary Search Report, European Application No. 02749804.7, Dec. 3, 2007, 11 pages.
Hoon et al., "Putative Mammalian Taste Receptors: A Class of Taste-Specific GPCRs with Distinct Topographic Selectivity," Cell, Feb. 19, 1999, pp. 541-551, vol. 96, Cell Press.
Kitagawa, M., et al., "Molecular Genetic Identification of a Candidate Receptor Gene for Sweet Taste," Biochemical and Biophysical Research Communications, Apr. 27, 2001, pp. 236-242, vol. 283, No. 1.
Li et al., "Human Receptors for Sweet and Umami Taste," PNAS, Apr. 2, 2002, pp. 4692-4696, vol. 99, No. 7.
Li, X. et al., "High-Resolution Genetic Mapping of the Saccharin Preference Locus (Sac) and the Putative Sweet Taste Receptor (T1R1) Gene (Gpr70) to Mouse Distal Chromosome 4," Mammalian Genome, Jan. 2001, pp. 13-16, vol. 12, No. 1.
Max, M. et al., "Tas1r3, Encoding a New Candidate Taste Receptor, is Allelic to the Sweet Responsiveness Locus Sac," Nature Genetics, May 2001, pp. 492-498, vol. 28.
Montmayeur et al., "A Candidate Taste Receptor Gene Near a Sweet Taste Locus," Nature Neuroscience, May 2001, pp. 492-498, vol. 4, No. 5.
Nelson et al., "An Amino-Acid Taste Receptor," Nature, DOI 10.1038/nature726 www.nature.com, Feb. 24, 2002, 4 pages.
Nelson et al., "Mammalian Sweet Taste Receptors," Cell, Aug. 10, 2001, pp. 381-390, vol. 106, Cell Press.
Sainz, E. et al., "Identification of a Novel Member of the T1R Family of Putative Taste Receptors," Journal of Neurochemistry, May 2001, pp. 896-903, vol. 77, No. 3.
Canadian Office Action, Canadian Application No. 2,452,716, Nov. 3, 2009, 5 pages.
Japanese Office Action, Japanese Application No. 2003-510918, Aug. 20, 2009, 4 pages.
United States Office Action, U.S. Appl. No. 12/121,576, Jan. 6, 2010, 6 pages.
United States Office Action, U.S. Appl. No. 12/147,415, Feb. 16, 2010, 11 pages. European Examination Report, European Application No. 02749804.7, Sep. 10, 2010, 9 pages.

*Primary Examiner* — John D Ulm
(74) *Attorney, Agent, or Firm* — Fenwick & West LLP

(57) ABSTRACT

The present invention provides isolated nucleic acid and amino acid sequences of sweet taste receptors, the receptors comprising consisting of a monomer or homodimer of a T1R3 G-protein coupled receptor polypeptide, antibodies to such receptors, methods of detecting such nucleic acids and receptors, and methods of screening for modulators of sweet and amino acid taste receptors.

25 Claims, 17 Drawing Sheets

T1R1

T1R2

T1R3

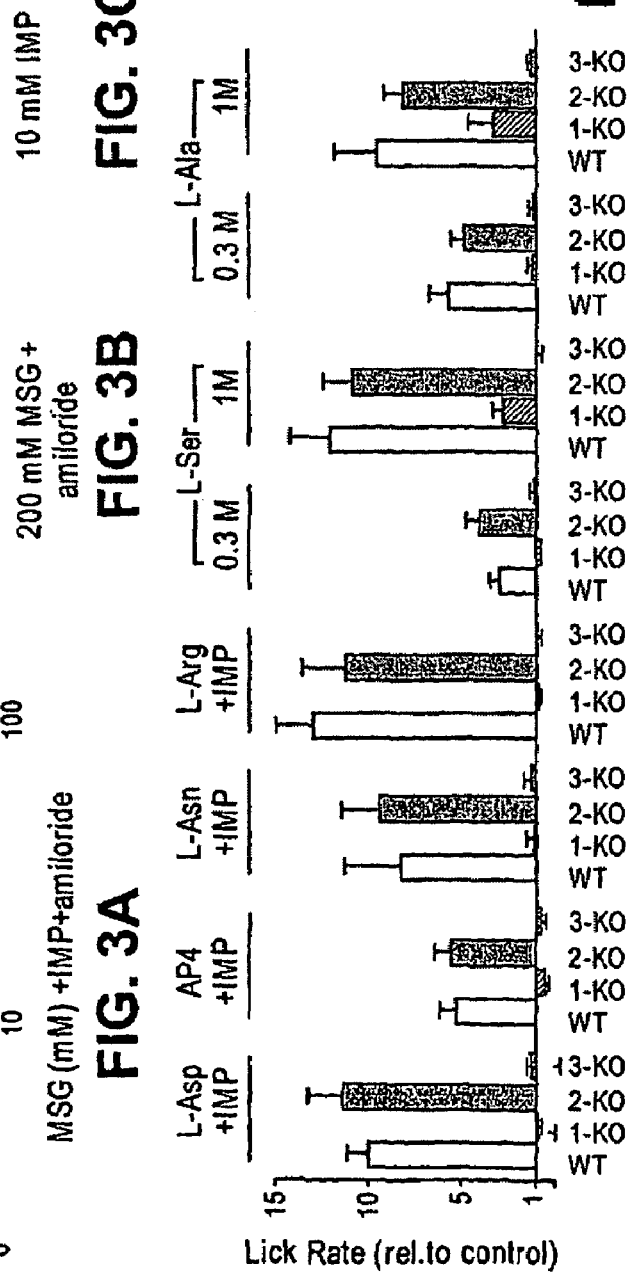

hT1R1 SEQ ID NO: 26

ATGCTGCTCTGCACGGCTCGCCTGGTCGGCCTGCAGCTTCTCATTTCCTGCTGCTGGGCC
TTTGCCTGCCATAGCACGGAGTCTTCTCCTGACTTCACCCTCCCCGGAGATTACCTCCTG
GCAGGCCTGTTCCCTCTCCATTCTGGCTGTCTGCAGGTGAGGCACAGACCCGAGGTGACC
CTGTGTGACAGGTCTTGTAGCTTCAATGAGCATGGCTACCACCTCTTCCAGGCTATGCGG
CTTGGGGTTGAGGAGATAAACAACTCCACGGCCCTGCTGCCCAACATCACCCTGGGGTAC
CAGCTGTATGATGTGTGTTCTGACTCTGCCAATGTGTATGCCACGCTGAGAGTGCTCTCC
CTGCCAGGGCAACACCACATAGAGCTCCAAGGAGACCTTCTCCACTATTCCCCTACGGTG
CTGGCAGTGATTGGGCCTGACAGCACCAACCGTGCTGCCACCACAGCCGCCCTGCTGAGC
CCTTTCCTGGTGCCCATGATTAGCTATGCGGCCAGCAGCGAGACGCTCAGCGTGAAGCGG
CAGTATCCCTCTTTCCTGCGCACCATCCCCAATGACAAGTACCAGGTGGAGACCATGGTG
CTGCTGCTGCAGAAGTTCGGGTGGACCTGGATCTCTCTGGTTGGCAGCAGTGACGACTAT
GGGCAGCTAGGGGTGCAGGCACTGGAGAACCAGGCCACTGGTCAGGGCATCTGCATTGC
TTTCAAGGACATCATGCCCTTCTCTGCCCAGGTGGGCGATGAGAGGATGCAGTGCCTCAT
GCGCCACCTGGCCCAGGCCGGGGCCACCGTCGTGGTTGTTTTTCCAGCCGGCAGTTGGC
CAGGGTGTTTTTCGAGTCCGTGGTGCTGACCAACCTGACTGGCAAGGTGTGGGTCGCCTC
AGAAGCCTGGGCCCTCTCCAGGCACATCACTGGGGTGCCCGGGATCCAGCGCATTGGAT
GGTGCTGGGCGTGGCCATCCAGAAGAGGGCTGTCCCTGGCCTGAAGGCGTTTGAAGAAGC
CTATGCCCGGGCAGACAAGAAGGCCCCTAGGCCTTGCCACAAGGGCTCCTGGTGCAGCAG
CAATCAGCTCTGCAGAGAATGCCAAGCTTTCATGGCACACACGATGCCCAAGCTCAAAGC
CTTCTCCATGAGTTCTGCCTACAACGCATACCGGGCTGTGTATGCGGTGGCCCATGGCCT
CCACCAGCTCCTGGGCTGTGCCTCTGGAGCTTGTTCCAGGGGCCGAGTCTACCCCTGGCA
GCTTTTGGAGCAGATCCACAAGGTGCATTTCCTTCTACACAAGGACACTGTGGCGTTTAA
TGACAACAGAGATCCCCTCAGTAGCTATAACATAATTGCCTGGGACTGGAATGGACCCAA
GTGGACCTTCACGGTCCTCGGTTCCTCCACATGGTCTCCAGTTCAGCTAAACATAAATGA
GACCAAAATCCAGTGGCACGGAAAGGACAACCAGGTGCCTAAGTCTGTGTGTTCCAGCGA
CTGTCTTGAAGGGCACCAGCGAGTGGTTACGGGTTTCCATCACTGCTGCTTTGAGTGTGT
GCCCTGTGGGGCTGGGACCTTCCTCAACAAGAGTGACCTCTACAGATGCCAGCCTTGTGG
GAAAGAAGAGTGGGCACCTGAGGGAAGCCAGACCTGCTTCCCGCGCACTGTGGTGTTTTT
GGCTTTGCGTGAGCACACCTCTTGGGTGCTGCTGGCAGCTAACACGCTGCTGCTGCTGCT
GCTGCTTGGGACTGCTGGCCTGTTTGCCTGGCACCTAGACACCCCTGTGGTGAGGTCAGC
AGGGGGCCGCCTGTGCTTTCTTATGCTGGGCTCCCTGGCAGCAGGTAGTGGCAGCCTCTA
TGGCTTCTTTGGGGAACCCACAAGGCCTGCGTGCTTGCTACGCCAGGCCCTCTTTGCCCT
TGGTTTCACCATCTTCCTGTCCTGCCTGACAGTTCGCTCATTCCAACTAATCATCATCTT
CAAGTTTTCCACCAAGGTACCTACATTCTACCACGCCTGGGTCCAAAACCACGGTGCTGG
CCTGTTTGTGATGATCAGCTCAGCGGCCCAGCTGCTTATCTGTCTAACTTGGCTGGTGGT
GTGGACCCCACTGCCTGCTAGGGAATACCAGCGCTTCCCCCATCTGGTGATGCTTGAGTG
CACAGAGACCAACTCCCTGGGCTTCATACTGGCCTTCCTCTACAATGGCCTCCTCTCCAT
CAGTGCCTTTGCCTGCAGCTACCTGGGTAAGGACTTGCCAGAGAACTACAACGAGGCCAA
ATGTGTCACCTTCAGCCTGCTCTTCAACTTCGTGTCCTGGATCGCCTTCTTCACCACGGC
CAGCGTCTACGACGGCAAGTACCTGCCTGCGGCCAACATGATGGCTGGGCTGAGCAGCCT
GAGCAGCGGCTTCGGTGGGTATTTTCTGCCTAAGTGCTACGTGATCCTCTGCCGCCCAGA
CCTCAACAGCACAGAGCACTTCCAGGCCTCCATTCAGGACTACACGAGGCGCTGCGGCTC
CACCTGA

FIG. 8 hH1R1    SEQ ID NO:27

MLLCTARLVGLQLLISCCWAFACHSTESSPDETLPGDYLLAGLFPLHSGCLQVRHRPEVTLCDR
SCSFNEHGYHLFQAMRLGVEEINNSTALLPNITLGYQLYDVCSDSANVYATLRYLSLPGQHHIE
LQGDLLHYSPTVLAVIGPDSTNRAATTAALLSPFLVPMISYAASSETLSVKRQYPSFLRTIPNDK
YQVETMVLLLQKFGWTWISLVGSSDDYGQLGVQALENQATGQGICIAFKDIMPFSAQVGDER
MQCLMRHLAQAGATVVVVFSSRQLARVFFESVVLTNLTGKVWVASEAWALSRHITGVPGIQR
IGMVLGVAIQKRAVPGLKAFEEAYARADKKAPRPCHKGSWCSSNQLRECQAFMAHTMPKL
KAFSMSSAYNAYRAVYAVAHGLHQLLGCASGACSRGRVYPWQLLEQIHKVHFLLHKDTVAF
NDNRDPLSSYNIIAWDWNGPKWTFVLGSSIMSPVQLNINETKIQWHGKDNQVPKSVCSSDC
LEGHQRVVTGFHCCFECVPCGAGTFLNKSDLYRCQPCGKEEWAPEGSQTCFPRTVVFLALRE
HTSWVLLAANTLLLLLLLGTAGLFAWHLDTPVVRSAGGRLCFTMLGSLAAGSSLYGFFGEPT
RPACLLRQALFALGFTIFLSCLTVRSFQLIIFKFSIKVPTFYHAMVQNHGAGLFWMLSSAAQLLI
CLIWLVVVTPLPAREYQRFPHLVMLECTEINSLGFILAFLYNGLLSISAFACSYLGKDLPENYN
EAKCVTFSLLFNFVSWLAFFTTASVYDGKYLPAANMAGLSISLSSGFGGYTLPKCYVLCRPDL
NSTEHFQASIQDYTRRCGST

FIG. 9

```
ATGGGGCCCA GGGCAAAGAC CATCTGCTCC CTGTTCTTCC TCCTATGGGT CCTGGCTGAG
CCGGCTGAGA ACTCGGACTT CTACCTGCCT GGGGATTACC TCCTGGGTGG CCTCTTCTCC
CTCCATGCCA ACATGAAGGG CATTGTTCAC CTTAACTTCC TGCAGGTGCC CATGTGCAAG
GAGTATGAAG TGAAGGTGAT AGGCTACAAC CTCATGCAGG CCATGCGCTT CGCGGTGGAG
GAGATCAACA ATGACAGCAG CCTGCTGCCT GGTGTGCTGC TGGGCTATGA GATCGTGGAT
GTGTGCTACA TCTCCAACAA TGTCCAGCCG GTGCTCTACT TCCTGGCACA CGAGGACAAC
CTCCTTCCCA TCCAAGAGGA CTACAGTAAC TACATTTCCC GTGTGGTGGC TGTCATTGGC
CCTGACAACT CCGAGTCTGT CATGACTGTG GCCAACTTCC TCTCCCTATT TCTCCTTCCA
CAGATCACCT ACAGCGCCAT CAGCGATGAG CTGCGAGACA AGGTGCGCTT CCCGGCTTTG
CTGCGTACCA CACCCAGCGC CGACCACCAC GTCGAGGCCA TGGTGCAGCT GATGCTGCAC
TTCGCTGGA ACTGGATCAT TGTGCTGGTG AGCAGCGACA CCTATGGCCG CGACAATGGC
CAGCTGCTTG GCGAGCGCGT GGCCCGGCGC GACATCTGCA TCGCCTTCCA GGAGACGCTG
CCCACACTGC AGCCCAACCA GAACATGACG TCAGAGGAGC GCCAGCGCCT GGTGACCATT
GTGGACAAGC TGCAGCAGAG CACAGCGCGC GTCGTGGTCG TGTTCTCGCC CGACCTGACC
CTGTACCACT TCTTCAATGA GGTGCTGCGC CAGAACTTCA CGGGCGCCGT GTGGATCGCC
TCCGAGTCCT GGGCCATCGA CCCGGTCCTG CACAACCTCA CGGAGCTGGG CCACTTGGGC
ACCTTCCTGG GCATCACCAT CCAGAGCGTG CCCATCCCGG GCTTCAGTGA GTTCCGCGAG
TGGGGCCCAC AGGCTGGGCC GCCAC
```

FIG. 10

Human T1R2 amino acid sequence—SEQ ID NO: 29

MGPRAKTICSLFFLLWVLAEPAENSDFYLPGDYLLGGLFSLHANMKGIVHLNFLQVPMCKEY
EVKVIGYNLMQAMRFAVEEINNDSSLLPGVLLGYEIVDVCYISNNVQPVLYFLAHEDNLLPI
QEDYSNYISRVVAVIGPDNSESVMTVANFLSLFLLPQITYSAISDELRDKVRFPALIRTTPS
ADHHVEAMVQLMLHFRWNWIIVLVSSDTYGRDNGQLLGERVARRDICIAFQETLPTLQPNQN
MTSEERQRLVTIVDKLQQSTARVVVVESPDLITLYHFFNEVLRQNFTGAVWIASESWAIDPVL
HNLTELGHLGTFLGITIQSVPIPGFSEFREWGPQAGPPPLSRTSQSYTCNQECDNCLNATLS
FNTILRLSGERVVYSVYSAVYAVAHALHSLLGCDKSTCTCKRVVYPWQLLEEIWKVNFTLLDH
QIFFDPQGDVALHLEIVQWQDRSQNPFQSVASYYPLQRQLKNIQDISWHTVNNTIPMSMCS
KRCQSGQKKPKPVGIHVCCFECIDCLPGTELNHIEDEYECQACPNNEWSYQSETSCFKRQLVE
LEWHEAPTIAVALLAALGFLSTLAILVIFWRHFQTPIVRSAGGPMCFLMTLLLVAYMVVPV
YVGPPKVSTCLCRQALFPLCFTICISCIAVRSFQIVCAFKMASRFPRAYSYWVRYQGPYVSM
AFITVLKMVIVIGMLARPQSHPRTDPDDPKITIVSCNPNYRNSLLFNTSLDLLISVVGFSF
AYMGKELPTNYNEAKFITLSMTFYFTSSVSLCTFMSAYSGVLITIVDLLIVTVINLLAISLGY
FGPKCYMILFYPERNTPAYFNSMIQGYTMRRD

FIG. 11 hT1R1 SEQ ID NO: 30

ATGCTGGGCCCTGCTGTCCTGGGCCTCAGCCTCTGGGCTCTCCTGCACCCTGGGACGGGG
GCCCCATTGTGCCTGTCACAGCAACTTAGGATGAAGGGGGACTACGTGCTGGGGGGGCTG
TTCCCCCTGGGCGAGGCCGAGGAGGCTGGCCTCCGCAGCCGGACACGGCCCAGCAGCCCT
GTGTGCACCAGGTTCTCCTCAAACGGCCTGCTCTGGGCACTGGCCATGAAAATGGCCGTG
GAGGAGATCAACAACAAGTCGGATCTGCTGCCCGGGCTGCGCCTGGGCTACGACCTCTTT
GATACGTGCTCGGAGCCTGTGGTGGCCATGAAGCCCAGCCTCATGTTCCTGGCCAAGGCA
GGCAGCCGCGACATCGCCGCCTACTGCAACTACACGCAGTACCAGCCCCGTGTGCTGGCT
GTCATCGGGCCCCACTCGTCAGAGCTCGCCATGGTCACCGGCAAGTTCTTCAGCTTCTTC
CTCATGCCCCAGGTCAGCTACGGTGCTAGCATGGAGCTGCTGAGCGCCCGGGAGACCTTC
CCCTCCTTCTTCCGCACCGTGCCCAGCGACCGTGTGCAGCTGACGGCCGCCGCGGAGCTG
CTGCAGGAGTTCGGCTGGAACTGGGTGGCCGCCCTGGGCAGCGACGACGAGTACGGCCGG
CAGGGCCTGAGCATCTTCTCGGCCCTGGCCGCGGCACGCGGCATCTGCATCGCGCACGAG
GGCCTGGTGCCGCTGCCCCGTGCCGATGACTCGCGGCTGGGGAAGGTGCAGGACGTCCTG
CACCAGGTGAACCAGAGCAGCGTGCAGGTGGTGCTGCTGTTCGCCTCCGTGCACGCCGCC
CACGCCCTCTTCAACTACAGCATCAGCAGCAGGCTCTCGCCCAAGGTGTGGGTGGCCAGC
GAGGCCTGGCTGACCTCTGACCTGGTCATGGGGCTGCCCGGCATGGCCCAGATGGGCACG
GTGCTTGGCTTCCTCCAGAGGGGTGCCCAGCTGCACGAGTTCCCCCAGTACGTGAAGACG
CACCTGGCCCTGGCCACCGACCCGGCCTTCTGCTCTGCCCTGGGCGAGAGGGAGCAGGGT
CTGGAGGAGGACGTGGTGGGCCAGCGCTGCCCGCAGTGTGACTGCATCACGCTGCAGAAC
GTGAGCGCAGGGCTAAATCACCACCAGACGTTCTCTGTCTACGCAGCTGTGTATAGCGTG
GCCCAGGCCCTGCACAACACTCTTCAGTGCAACGCCTCAGGCTGCCCCGCGCAGGACCCC
GTGAAGCCCTGGCAGCTCCTGGAGAACATGTACAACCTGACCTTCCACGTGGGCGGGCTG
CCGCTGCGGTTCGACAGCAGCGGAAACGTGGACATGGAGTACGACCTGAAGCTGTGGGTG
TGGCAGGGCTCAGTGCCCAGGCTCCACGACGTGGGCAGGTTCAACGGCAGCCTCAGGACA
GAGCGCCTGAAGATCCGCTGGCACACGTCTGACAACCAGAAGCCCGTGTCCCGGTGCTCG
CGGCAGTGCCAGGAGGGCCAGGTGCGCCGGGTCAAGGGGTTCCACTCCTGCTGCTACGAC
TGTGTGGACTGCGAGGCGGGCAGCTACCGGCAAAACCCAGACGACATCGCCTGCACCTTT
TGTGGCCAGGATGAGTGGTCCCCGGAGCGAAGCACACGCTGCTTCCGCCGCAGGTCTCGG
TTCCTGGCATGGGGCGAGCCGGCTGTGCTGCTGCTGCTCCTGCTGCTGAGCCTGGCGCTG
GGCCTTGTGCTGGCTGCTTTGGGGCTGTTCGTTCACCATCGGGACAGCCCACTGGTTCAG
GCCTCGGGGGGCCCCTGGCCTGCTTTGGCCTGGTGTGCCTGGGCCTGGTCTGCCTCAGC
GTCCTCCTGTTCCCTGGCCAGCCCAGCCCTGCCCGATGCCTGGCCCAGCAGCCCTTGTCC
CACCTCCCGCTCACGGGCTGCCTGAGCACACTCTTCCTGCAGGCGGCCGAGATCTTCGTG
GAGTCAGAACTGCCTCTGAGCTGGGCAGACCGGCTGAGTGGCTGCCTGCGGGGCCCTGG
GCCTGGCTGGTGGTGCTGCTGGCCATGCTGGTGGAGGTCGCACTGTGCACCTGGTACCTG
GTGGCCTTCCCGCCGGAGGTGGTGACGGACTGGCACATGCTGCCCACGGAGGCGCTGGTG
CACTGCCGCACACGCTCCTGGGTCAGCTTCGGCCTAGCGCACGCCACCAATGCCACGCTG
GCCTTTCTCTGCTTCCTGGGCACTTTCCTGGTGCGGAGCCAGCCGGGCTGCTACAACCGT
GCCCGTGGCCTCACCTTTGCCATGCTGGCCTACTTCATCACCTGGGTCTCCTTTGTGCCC
CTCCTGGCCAATGTGCAGGTGGTCCTCAGGCCCGCCGTGCAGATGGGCGCCCTCCTGCTC
TGTGTCCTGGGCATCCTGGCTGCCTTCCACCTGCCCAGGTGTTACCTGCTCATGCGGCAG
CCAGGGCTCAACACCCCCGAGTTCTTCCTGGGAGGGGCCCTGGGGATGCCCAAGGCCAG
AATGACGGGAACACAGGAAATCAGGGGAAACATGAGTGA

FIG. 12 hT1R3    SEQ ID NO: 31

MLGPAVLGLSLWALLHPGTGAPLCLSQQLRMKGDYVLGGLFPLGEAEEAGLRSRTRPSSPVCT
RFSSNGLLWALAMKMAVEEINNKSDLLPGLRLGYDLFDTCSEPVVAMKPSLMFLAKAGSRDI
AAYCNYTQYQPRVLAVIGPHSSELAMVTGKFFSFFLMPPHYGASMELLSARETFPSFFRTVPSDR
VQLTAAAELLQEFGWNWVAALGSDDEYGRQGLSIFSALAAARGICIAHEGLVPLPRADDSRLG

KVQDVLHQVNQSSVQVVLLFASVHAAHALFNYSISSRLSPKVWVASEAWLTSDLVMGLPGM
AQMGTVLGFLQRGAQLHEFPQYVKTHLALATDPAFCSALGEREQGLEEDVVGQRCPQCDCIT
LQNVSAGLNHHQTESVYAAVYSVAQALHNTLQCNASGCPAQDPVKPWQLLENMYNLTFHVG
GLPLRFDSSGNVDMEYDLKLIWWQGSVPRLHDVGRFNGSLRTERIKIRWHTSDNQKPVSRCS
RQCQEGQVRRVKGFHSCCYDCVDCEAGSYRQNPDDIACTFCGQDEWSPERSTRCFRRRSRFLA
WGEPAVLLLLLLSLALGLVLAALGLFVHHRDSPLVQASGGPLACFGLVCLSVLLFPG
QPSPARCLAQQPLSHLPLTGCLSTLFLQAAEIFVESELPLSWADRLGCLRGPWAWLVLLAML
VEVALCTWYLVAFPPEVVTDWHMLPTEALVHCRTRSWVSFGLAHATNATLAFLCFLGTFLVR
SQPGCYNRARGLTFAMLAYFITWVSFVPLLANVQVVLRPAVQMGALLLCVLGILAAFHLPRCY
LLMRQPGLNTPEFFLGGGPGDAQGQNDGNTGNQGKHE

FIG. 13

SEQUENCE LISTING

```
<160> NUMBER OF SEQ ID NOS: 32

<210> SEQ ID NO 1
<211> LENGTH: 840
<212> TYPE: PRT
<213> ORGANISM: Rattus sp.
<220> FEATURE:
<223> OTHER INFORMATION: rat T1R1 G-protein coupled receptor sweet
      taste receptor

<400> SEQUENCE: 1
```

Met Leu Phe Trp Ala Ala His Leu Leu Leu Ser Leu Gln Leu Val Tyr
 1               5                  10                  15

Cys Trp Ala Phe Ser Cys Gln Arg Thr Glu Ser Ser Pro Gly Phe Ser
            20                  25                  30

Leu Pro Gly Asp Phe Leu Leu Ala Gly Leu Phe Ser Leu His Gly Asp
        35                  40                  45

Cys Leu Gln Val Arg His Arg Pro Leu Val Thr Ser Cys Asp Arg Pro
    50                  55                  60

Asp Ser Phe Asn Gly His Gly Tyr His Leu Phe Gln Ala Met Arg Phe
65                  70                  75                  80

Thr Val Glu Glu Ile Asn Asn Ser Ser Ala Leu Leu Pro Asn Ile Thr
                85                  90                  95

Leu Gly Tyr Glu Leu Tyr Asp Val Cys Ser Glu Ser Ala Asn Val Tyr
            100                 105                 110

Ala Thr Leu Arg Val Leu Ala Leu Gln Gly Pro Arg His Ile Glu Ile
        115                 120                 125

Gln Lys Asp Leu Arg Asn His Ser Ser Lys Val Val Ala Phe Ile Gly
    130                 135                 140

Pro Asp Asn Thr Asp His Ala Val Thr Thr Ala Ala Leu Leu Gly Pro
145                 150                 155                 160

Phe Leu Met Pro Leu Val Ser Tyr Glu Ala Ser Ser Val Val Leu Ser
                165                 170                 175

Ala Lys Arg Lys Phe Pro Ser Phe Leu Arg Thr Val Pro Ser Asp Arg
            180                 185                 190

His Gln Val Glu Val Met Val Gln Leu Leu Gln Ser Phe Gly Trp Val
        195                 200                 205

Trp Ile Ser Leu Ile Gly Ser Tyr Gly Asp Tyr Gly Gln Leu Gly Val
    210                 215                 220

Gln Ala Leu Glu Glu Leu Ala Val Pro Arg Gly Ile Cys Val Ala Phe
225                 230                 235                 240

Lys Asp Ile Val Pro Phe Ser Ala Arg Val Gly Asp Pro Arg Met Gln
                245                 250                 255

Ser Met Met Gln His Leu Ala Gln Ala Arg Thr Thr Val Val Val Val
            260                 265                 270

Phe Ser Asn Arg His Leu Ala Arg Val Phe Phe Arg Ser Val Val Leu
        275                 280                 285

Ala Asn Leu Thr Gly Lys Val Trp Val Ala Ser Glu Asp Trp Ala Ile
    290                 295                 300

Ser Thr Tyr Ile Thr Ser Val Thr Gly Ile Gln Gly Ile Gly Thr Val
305                 310                 315                 320

Leu Gly Val Ala Val Gln Gln Arg Gln Val Pro Gly Leu Lys Glu Phe
                325                 330                 335

Glu Glu Ser Tyr Val Arg Ala Val Thr Ala Ala Pro Ser Ala Cys Pro
            340                 345                 350

Glu Gly Ser Trp Cys Ser Thr Asn Gln Leu Cys Arg Glu Cys His Thr
        355                 360                 365

Phe Thr Thr Arg Asn Met Pro Thr Leu Gly Ala Phe Ser Met Ser Ala
    370                 375                 380

Ala Tyr Arg Val Tyr Glu Ala Val Tyr Ala Val Ala His Gly Leu His
385                 390                 395                 400

Gln Leu Leu Gly Cys Thr Ser Glu Ile Cys Ser Arg Gly Pro Val Tyr
                405                 410                 415

Pro Trp Gln Leu Leu Gln Gln Ile Tyr Lys Val Asn Phe Leu Leu His
            420                 425                 430

Glu Asn Thr Val Ala Phe Asp Asp Asn Gly Asp Thr Leu Gly Tyr Tyr
        435                 440                 445

Asp Ile Ile Ala Trp Asp Trp Asn Gly Pro Glu Trp Thr Phe Glu Ile
    450                 455                 460

Ile Gly Ser Ala Ser Leu Ser Pro Val His Leu Asp Ile Asn Lys Thr
465                 470                 475                 480

Lys Ile Gln Trp His Gly Lys Asn Asn Gln Val Pro Val Ser Val Cys
                485                 490                 495

Thr Thr Asp Cys Leu Ala Gly His His Arg Val Val Val Gly Ser His
            500                 505                 510

His Cys Cys Phe Glu Cys Val Pro Cys Glu Ala Gly Thr Phe Leu Asn

```
            515                 520                 525
Met Ser Glu Leu His Ile Cys Gln Pro Cys Gly Thr Glu Glu Trp Ala
    530                 535                 540

Pro Lys Glu Ser Thr Thr Cys Phe Pro Arg Thr Val Glu Phe Leu Ala
545                 550                 555                 560

Trp His Glu Pro Ile Ser Leu Val Leu Ile Ala Ala Asn Thr Leu Leu
                565                 570                 575

Leu Leu Leu Leu Val Gly Thr Ala Gly Leu Phe Ala Trp His Phe His
            580                 585                 590

Thr Pro Val Val Arg Ser Ala Gly Gly Arg Leu Cys Phe Leu Met Leu
        595                 600                 605

Gly Ser Leu Val Ala Gly Ser Cys Ser Phe Tyr Ser Phe Phe Gly Glu
610                 615                 620

Pro Thr Val Pro Ala Cys Leu Leu Arg Gln Pro Leu Phe Ser Leu Gly
625                 630                 635                 640

Phe Ala Ile Phe Leu Ser Cys Leu Thr Ile Arg Ser Phe Gln Leu Val
                645                 650                 655

Ile Ile Phe Lys Phe Ser Thr Lys Val Pro Thr Phe Tyr Arg Thr Trp
            660                 665                 670

Ala Gln Asn His Gly Ala Gly Leu Phe Val Ile Val Ser Ser Thr Val
        675                 680                 685

His Leu Leu Ile Cys Leu Thr Trp Leu Val Met Trp Thr Pro Arg Pro
690                 695                 700

Thr Arg Glu Tyr Gln Arg Phe Pro His Leu Val Ile Leu Glu Cys Thr
705                 710                 715                 720

Glu Val Asn Ser Val Gly Phe Leu Leu Ala Phe Thr His Asn Ile Leu
                725                 730                 735

Leu Ser Ile Ser Thr Phe Val Cys Ser Tyr Leu Gly Lys Glu Leu Pro
            740                 745                 750

Glu Asn Tyr Asn Glu Ala Lys Cys Val Thr Phe Ser Leu Leu Leu Asn
        755                 760                 765

Phe Val Ser Trp Ile Ala Phe Phe Thr Met Ala Ser Ile Tyr Gln Gly
770                 775                 780

Ser Tyr Leu Pro Ala Val Asn Val Leu Ala Gly Leu Thr Thr Leu Ser
785                 790                 795                 800

Gly Gly Phe Ser Gly Tyr Phe Leu Pro Lys Cys Tyr Val Ile Leu Cys
                805                 810                 815

Arg Pro Glu Leu Asn Asn Thr Glu His Phe Gln Ala Ser Ile Gln Asp
            820                 825                 830

Tyr Thr Arg Arg Cys Gly Thr Thr
        835                 840

<210> SEQ ID NO 2
<211> LENGTH: 842
<212> TYPE: PRT
<213> ORGANISM: Mus sp.
<220> FEATURE:
<223> OTHER INFORMATION: mouse T1R1 G-protein coupled receptor sweet
      taste receptor

<400> SEQUENCE: 2

Met Leu Phe Trp Ala Ala His Leu Leu Leu Ser Leu Gln Leu Ala Val
  1               5                  10                  15

Ala Tyr Cys Trp Ala Phe Ser Cys Gln Arg Thr Glu Ser Ser Pro Gly
             20                  25                  30

Phe Ser Leu Pro Gly Asp Phe Leu Leu Ala Gly Leu Phe Ser Leu His
```

```
                    35                  40                  45
Ala Asp Cys Leu Gln Val Arg His Arg Pro Leu Val Thr Ser Cys Asp
                50                  55                  60

Arg Ser Asp Ser Phe Asn Gly His Gly Tyr His Leu Phe Gln Ala Met
 65                  70                  75                  80

Arg Phe Thr Val Glu Glu Ile Asn Asn Ser Thr Ala Leu Leu Pro Asn
                    85                  90                  95

Ile Thr Leu Gly Tyr Glu Leu Tyr Asp Val Cys Ser Glu Ser Ser Asn
                100                 105                 110

Val Tyr Ala Thr Leu Arg Val Pro Ala Gln Gln Gly Thr Gly His Leu
                115                 120                 125

Glu Met Gln Arg Asp Leu Arg Asn His Ser Ser Lys Val Val Ala Leu
                130                 135                 140

Ile Gly Pro Asp Asn Thr Asp His Ala Val Thr Thr Ala Ala Leu Leu
145                 150                 155                 160

Ser Pro Phe Leu Met Pro Leu Val Ser Tyr Glu Ala Ser Ser Val Ile
                165                 170                 175

Leu Ser Gly Lys Arg Lys Phe Pro Ser Phe Leu Arg Thr Ile Pro Ser
                180                 185                 190

Asp Lys Tyr Gln Val Glu Val Ile Val Arg Leu Leu Gln Ser Phe Gly
                195                 200                 205

Trp Val Trp Ile Ser Leu Val Gly Ser Tyr Gly Asp Tyr Gly Gln Leu
                210                 215                 220

Gly Val Gln Ala Leu Glu Glu Leu Ala Thr Pro Arg Gly Ile Cys Val
225                 230                 235                 240

Ala Phe Lys Asp Val Val Pro Leu Ser Ala Gln Ala Gly Asp Pro Arg
                245                 250                 255

Met Gln Arg Met Met Leu Arg Leu Ala Arg Ala Arg Thr Thr Val Val
                260                 265                 270

Val Val Phe Ser Asn Arg His Leu Ala Gly Val Phe Phe Arg Ser Val
                275                 280                 285

Val Leu Ala Asn Leu Thr Gly Lys Val Trp Ile Ala Ser Glu Asp Trp
                290                 295                 300

Ala Ile Ser Thr Tyr Ile Thr Asn Val Pro Gly Ile Gln Gly Ile Gly
305                 310                 315                 320

Thr Val Leu Gly Val Ala Ile Gln Gln Arg Gln Val Pro Gly Leu Lys
                325                 330                 335

Glu Phe Glu Glu Ser Tyr Val Gln Ala Val Met Gly Ala Pro Arg Thr
                340                 345                 350

Cys Pro Glu Gly Ser Trp Cys Gly Thr Asn Gln Leu Cys Arg Glu Cys
                355                 360                 365

His Ala Phe Thr Thr Trp Asn Met Pro Glu Leu Gly Ala Phe Ser Met
                370                 375                 380

Ser Ala Ala Tyr Asn Val Tyr Glu Ala Val Tyr Ala Val Ala His Gly
385                 390                 395                 400

Leu His Gln Leu Leu Gly Cys Thr Ser Gly Thr Cys Ala Arg Gly Pro
                405                 410                 415

Val Tyr Pro Trp Gln Leu Leu Gln Gln Ile Tyr Lys Val Asn Phe Leu
                420                 425                 430

Leu His Lys Lys Thr Val Ala Phe Asp Asp Lys Gly Asp Pro Leu Gly
                435                 440                 445

Tyr Tyr Asp Ile Ile Ala Trp Asp Trp Asn Gly Pro Glu Trp Thr Phe
450                 455                 460
```

```
Glu Val Ile Gly Ser Ala Ser Leu Ser Pro Val His Leu Asp Ile Asn
465                 470                 475                 480

Lys Thr Lys Ile Gln Trp His Gly Lys Asn Gln Val Pro Val Ser
            485                 490                 495

Val Cys Thr Arg Asp Cys Leu Glu Gly His His Arg Leu Val Met Gly
            500                 505                 510

Ser His His Cys Cys Phe Glu Cys Met Pro Cys Glu Ala Gly Thr Phe
        515                 520                 525

Leu Asn Thr Ser Glu Leu His Thr Cys Gln Pro Cys Gly Thr Glu Glu
    530                 535                 540

Trp Ala Pro Glu Gly Ser Ser Ala Cys Phe Ser Arg Thr Val Glu Phe
545                 550                 555                 560

Leu Gly Trp His Glu Pro Ile Ser Leu Val Leu Leu Ala Ala Asn Thr
                565                 570                 575

Leu Leu Leu Leu Leu Leu Ile Gly Thr Ala Gly Leu Phe Ala Trp Arg
            580                 585                 590

Leu His Thr Pro Val Val Arg Ser Ala Gly Gly Arg Leu Cys Phe Leu
        595                 600                 605

Met Leu Gly Ser Leu Val Ala Gly Ser Cys Ser Leu Tyr Ser Phe Phe
    610                 615                 620

Gly Lys Pro Thr Val Pro Ala Cys Leu Leu Arg Gln Pro Leu Phe Ser
625                 630                 635                 640

Leu Gly Phe Ala Ile Phe Leu Ser Cys Leu Thr Ile Arg Ser Phe Gln
                645                 650                 655

Leu Val Ile Ile Phe Lys Phe Ser Thr Lys Val Pro Thr Phe Tyr His
            660                 665                 670

Thr Trp Ala Gln Asn His Gly Ala Gly Ile Phe Val Ile Val Ser Ser
        675                 680                 685

Thr Val His Leu Phe Leu Cys Leu Thr Trp Leu Ala Met Trp Thr Pro
    690                 695                 700

Arg Pro Thr Arg Glu Tyr Gln Arg Phe Pro His Leu Val Ile Leu Glu
705                 710                 715                 720

Cys Thr Glu Val Asn Ser Val Gly Phe Leu Val Ala Phe Ala His Asn
                725                 730                 735

Ile Leu Leu Ser Ile Ser Thr Phe Val Cys Ser Tyr Leu Gly Lys Glu
            740                 745                 750

Leu Pro Glu Asn Tyr Asn Glu Ala Lys Cys Val Thr Phe Ser Leu Leu
        755                 760                 765

Leu His Phe Val Ser Trp Ile Ala Phe Phe Thr Met Ser Ser Ile Tyr
    770                 775                 780

Gln Gly Ser Tyr Leu Pro Ala Val Asn Val Leu Ala Gly Leu Ala Thr
785                 790                 795                 800

Leu Ser Gly Gly Phe Ser Gly Tyr Phe Leu Pro Lys Cys Tyr Val Ile
                805                 810                 815

Leu Cys Arg Pro Glu Leu Asn Asn Thr Glu His Phe Gln Ala Ser Ile
            820                 825                 830

Gln Asp Tyr Thr Arg Arg Cys Gly Thr Thr
        835                 840

<210> SEQ ID NO 3
<211> LENGTH: 840
<212> TYPE: PRT
<213> ORGANISM: Homo sapiens
<220> FEATURE:
<223> OTHER INFORMATION: human T1R1 G-protein coupled receptor sweet
      taste receptor
```

```
<400> SEQUENCE: 3

Met Leu Leu Cys Thr Ala Arg Leu Val Gly Leu Gln Leu Leu Ile Ser
 1               5                  10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val His Ile Ser Tyr Ala Ala Ser Ser Glu Thr Leu Ser
                165                 170                 175

Val Lys Arg Gln Tyr Pro Ser Phe Leu Arg Thr Ile Pro Asn Asp Lys
            180                 185                 190

Tyr Gln Val Glu Thr Met Val Leu Leu Gln Lys Phe Gly Trp Thr
        195                 200                 205

Trp Ile Ser Leu Val Gly Ser Ser Asp Asp Tyr Gly Gln Leu Gly Val
    210                 215                 220

Gln Ala Leu Glu Asn Gln Ala Leu Val Arg Gly Ile Cys Ile Ala Phe
225                 230                 235                 240

Lys Asp Ile Met Pro Phe Ser Ala Gln Val Gly Asp Glu Arg Met Gln
                245                 250                 255

Cys Leu Met Arg His Leu Ala Gln Ala Gly Ala Thr Val Val Val Val
            260                 265                 270

Phe Ser Ser Arg Gln Leu Ala Arg Val Phe Phe Glu Ser Val Val Leu
        275                 280                 285

Thr Asn Leu Thr Gly Lys Val Trp Val Ala Ser Glu Ala Trp Ala Leu
    290                 295                 300

Ser Arg His Ile Thr Gly Val Pro Gly Ile Gln Arg Ile Gly Met Val
305                 310                 315                 320

Leu Gly Val Ala Ile Gln Lys Arg Ala Val Pro Gly Leu Lys Ala Phe
                325                 330                 335

Glu Glu Ala Tyr Ala Arg Ala Asp Lys Glu Ala Pro Arg Pro Cys His
            340                 345                 350

Lys Gly Ser Trp Cys Ser Ser Asn Gln Leu Cys Arg Glu Cys Gln Ala
        355                 360                 365

Phe Met Ala His Thr Met Pro Lys Leu Lys Ala Phe Ser Met Ser Ser
    370                 375                 380

Ala Tyr Asn Ala Tyr Arg Ala Val Tyr Ala Val Ala His Gly Leu His
385                 390                 395                 400

Gln Leu Leu Gly Cys Ala Ser Glu Leu Cys Ser Arg Gly Arg Val Tyr
                405                 410                 415
```

```
Pro Trp Gln Leu Leu Glu Gln Ile His Lys Val His Phe Leu Leu His
        420                 425                 430

Lys Asp Thr Val Ala Phe Asn Asp Asn Arg Asp Pro Leu Ser Ser Tyr
        435                 440                 445

Asn Ile Ile Ala Trp Asp Trp Asn Gly Pro Lys Trp Thr Phe Thr Val
        450                 455                 460

Leu Gly Ser Ser Thr Trp Ser Pro Val Gln Leu Asn Ile Asn Glu Thr
465                 470                 475                 480

Lys Ile Gln Trp His Gly Lys Asn His Gln Val Pro Lys Ser Val Cys
                485                 490                 495

Ser Ser Asp Cys Leu Glu Gly His Gln Arg Val Val Thr Gly Phe His
                500                 505                 510

His Cys Cys Phe Glu Cys Val Pro Cys Gly Ala Gly Thr Phe Leu Asn
                515                 520                 525

Lys Ser Glu Leu Tyr Arg Cys Gln Pro Cys Gly Thr Glu Glu Trp Ala
                530                 535                 540

Pro Glu Gly Ser Gln Thr Cys Phe Pro Arg Thr Val Val Phe Leu Ala
545                 550                 555                 560

Leu Arg Glu His Thr Ser Trp Val Leu Leu Ala Ala Asn Thr Leu Leu
                565                 570                 575

Leu Leu Leu Leu Leu Gly Thr Ala Gly Leu Phe Ala Trp His Leu Asp
                580                 585                 590

Thr Pro Val Val Arg Ser Ala Gly Gly Arg Leu Cys Phe Leu Met Leu
                595                 600                 605

Gly Ser Leu Ala Ala Gly Ser Gly Ser Leu Tyr Gly Phe Phe Gly Glu
610                 615                 620

Pro Thr Arg Pro Ala Cys Leu Leu Arg Gln Ala Leu Phe Ala Leu Gly
625                 630                 635                 640

Phe Thr Ile Phe Leu Ser Cys Leu Thr Val Arg Ser Phe Gln Leu Ile
                645                 650                 655

Ile Ile Phe Lys Phe Ser Thr Lys Val Pro Thr Phe Tyr His Ala Trp
                660                 665                 670

Val Gln Asn His Gly Ala Gly Leu Phe Val Met Ile Ser Ser Ala Ala
                675                 680                 685

Gln Leu Leu Ile Cys Leu Thr Trp Leu Val Val Trp Thr Pro Leu Pro
                690                 695                 700

Ala Arg Glu Tyr Gln Arg Phe Pro His Leu Val Met Leu Glu Cys Thr
705                 710                 715                 720

Glu Thr Asn Ser Leu Gly Phe Ile Leu Ala Phe Leu Tyr Asn Gly Leu
                725                 730                 735

Leu Ser Ile Ser Ala Phe Ala Cys Ser Tyr Leu Gly Lys Asp Leu Pro
                740                 745                 750

Glu Asn Tyr Asn Glu Ala Lys Cys Val Thr Phe Ser Leu Leu Phe Asn
                755                 760                 765

Phe Val Ser Trp Ile Ala Phe Phe Thr Thr Ala Ser Val Tyr Asp Gly
                770                 775                 780

Lys Tyr Leu Pro Ala Ala Asn Met Met Ala Gly Leu Ser Ser Leu Ser
785                 790                 795                 800

Ser Gly Phe Gly Gly Tyr Phe Leu Pro Lys Cys Tyr Val Ile Leu Cys
                805                 810                 815

Arg Pro Asp Leu Asn Ser Thr Glu His Phe Gln Ala Ser Ile Gln Asp
                820                 825                 830

Tyr Thr Arg Arg Cys Gly Ser Thr
```

<210> SEQ ID NO 4
<211> LENGTH: 2771
<212> TYPE: DNA
<213> ORGANISM: Rattus sp.
<220> FEATURE:
<223> OTHER INFORMATION: rat T1R1 G-protein coupled receptor sweet taste receptor

<400> SEQUENCE: 4

| | | | | |
|---|---|---|---|---|
| attcacatca gagctgtgct cagccatgct gggcagaggg acgacggctg gccagcatgc | 60 |
| tcttctgggc tgctcacctg ctgctcagcc tgcagttggt ctactgctgg gctttcagct | 120 |
| gccaaaggac agagtcctct ccaggcttca gccttcctgg ggacttcctc cttgcaggtc | 180 |
| tgttctccct ccatggtgac tgtctgcagg tgagacacag acctctggtg acaagttgtg | 240 |
| acaggcccga cagcttcaac ggccatggct accacctctt ccaagccatg cggttcactg | 300 |
| ttgaggagat aaacaactcc tcggccctgc ttcccaacat caccctgggg tatgagctgt | 360 |
| acgacgtgtg ctcagaatct gccaatgtgt atgccaccct gagggtgctt gccctgcaag | 420 |
| ggccccgcca catagagata cagaaagacc ttcgcaacca ctcctccaag gtggtggcct | 480 |
| tcatcgggcc tgacaacact gaccacgctg tcactaccgc tgccttgctg gtccttttcc | 540 |
| tgatgcccct ggtcagctat gaggcaagca gcgtggtact cagtgccaag cgcaagttcc | 600 |
| cgtctttcct tcgtaccgtc cccagtgacc ggcaccaggt ggaggtcatg gtgcagctgc | 660 |
| tgcagagttt gggtgggtg tggatctcgc tcattggcag ctacggtgat tacgggcagc | 720 |
| tgggtgtgca ggcgctggag gagctggccg tgccccgggg catctgcgtc gccttcaagg | 780 |
| acatcgtgcc tttctctgcc cggtgggtg acccgaggat gcagagcatg atgcagcatc | 840 |
| tggctcaggc caggaccacc gtggttgtgg tcttctctaa ccggcacctg gctagagtgt | 900 |
| tcttcaggtc cgtggtgctg gccaacctga ctggcaaagt gtgggtcgcc tcagaagact | 960 |
| gggccatctc cacgtacatc accagcgtga ctgggatcca aggcattggg acggtgctcg | 1020 |
| gtgtggccgt ccagcagaga caagtccctg gctgaagga gtttgaggag tcttatgtca | 1080 |
| gggctgtaac agctgctccc agcgcttgcc cggaggggtc ctggtgcagc actaaccagc | 1140 |
| tgtgccggga gtgccacacg ttcacgactc gtaacatgcc cacgcttgga gccttctcca | 1200 |
| tgagtgccgc ctacagagtg tatgaggctg tgtacgctgt ggcccacggc ctccaccagc | 1260 |
| tcctgggatg tacttctgag atctgttcca gaggcccagt ctacccctgg cagcttcttc | 1320 |
| agcagatcta caaggtgaat tttcttctac atgagaatac tgtggcattt gatgacaacg | 1380 |
| gggacactct aggttactac gacatcatcg cctgggactg gaatggacct gaatggacct | 1440 |
| ttgagatcat tggctctgcc tcactgtctc cagttcatct ggacataaat aagacaaaaa | 1500 |
| tccagtggca cggaaagaac aatcaggtgc ctgtgtcagt gtgtaccacg actgtctgg | 1560 |
| cagggcacca cagggtggtt gtgggttccc accactgctg ctttgagtgt gtgccctgcg | 1620 |
| aagctgggac ctttctcaac atgagtgagc ttcacatctg ccagccttgt ggaacagaag | 1680 |
| aatgggcacc caaggagagc actacttgct tcccacgcac ggtggagttc ttggcttggc | 1740 |
| atgaacccat ctctttggtg ctaatagcag ctaacacgct attgctgctg ctgctggttg | 1800 |
| ggactgctgg cctgttgcc tggcattttc acacacctg agtgaggtca gctggggta | 1860 |
| ggctgtgctt cctcatgctg ggttccctgg tggccggaag ttgcagcttc tatagcttct | 1920 |
| tcggggagcc cacggtgccc gcgtgcttgc tgcgtcagcc cctcttttct ctcgggtttg | 1980 |
| ccatcttcct ctcctgcctg acaatccgct ccttccaact ggtcatcatc ttcaagtttt | 2040 |

```
ctaccaaggt gcccacattc taccgtacct gggcccaaaa ccatggtgca ggtctattcg   2100
tcattgtcag ctccacggtc catttgctca tctgtctcac atggcttgta atgtggaccc   2160
cacgacccac cagggaatac cagcgcttcc cccatctggt gattctcgag tgcacagagg   2220
tcaactctgt aggcttcctg ttggctttca cccacaacat tctcctctcc atcagtacct   2280
tcgtctgcag ctacctgggt aaggaactgc cagagaacta taatgaagcc aaatgtgtca   2340
ccttcagcct gctcctcaac ttcgtatcct ggatcgcctt cttcaccatg ccagcattt    2400 accagggcag ctacctgcct gcggtcaatg tgctggcagg gctgaccaca ctgagcggcg   2460
gcttcagcgg ttacttcctc cccaagtgct atgtgattct ctgccgtcca gaactcaaca   2520
atacagaaca ctttcaggcc tccatccagg actacgag cgctgcggc actacctgat       2580 ccactggaaa ggtgcagacg ggaaggaagc ctctcttctt gtgctgaagg tggcgggtcc   2640
agtggggccg agagcttgag gtgtctggga gagctccggc acagcttacg atgtataagc   2700
acgcggaaga atccagtgca ataaagacgg gaagtgtgaa aaaaaaaaa aaaaaaaaa     2760 aaaaaaaaaa a                                                       2771

<210> SEQ ID NO 5
<211> LENGTH: 2579
<212> TYPE: DNA
<213> ORGANISM: Mus sp.
<220> FEATURE:
<223> OTHER INFORMATION: mouse T1R1 G-protein coupled receptor sweet
      taste receptor

<400> SEQUENCE: 5
tttggccagc atgcttttct gggcagctca cctgctgctc agcctgcagc tggccgttgc     60
ttactgctgg gctttcagct gccaaaggac agaatcctct ccaggtttca gcctccctgg   120
ggacttcctc ctggcaggcc tgttctccct ccatgctgac tgtctgcagg tgagacacag   180
acctctggtg acaagttgtg acaggtctga cagcttcaac ggccatggct atcacctctt   240
ccaagccatg cggttcaccg ttgaggagat aaacaactcc acagctctgc ttcccaacat   300
cacccctggg tatgaactgt atgacgtgtg ctcagagtct ccaatgtct atgccaccct    360 gagggtgccc gcccagcaag ggacaggcca cctagagatg cagagagatc ttcgcaacca   420
ctcctccaag gtggtggcac tcattgggcc tgataacact gaccacgctg tcaccactgc   480
tgccctgctg agcccttttc tgatgccccct ggtcagctat gaggcgagca gcgtgatcct   540
cagtgggaag cgcaagttcc cgtccttctt gcgcaccatc cccagcgata agtaccaggt   600
ggaagtcata gtgcggctgc tgcagagctt cggctgggtc tggatctcgc tcgttggcag   660
ctatggtgac tacgggcagc tgggcgtaca ggcgctggag gagctggcca ctccacgggg   720
catctgcgtc gccttcaagg acgtggtgcc tctctccgcc caggcgggtg acccaaggat   780
gcagcgcatg atgctgcgtc tggctcgagc caggaccacc gtggtcgtgg tcttctctaa   840
ccggcacctg gctggagtgt cttcaggtc tgtggtgctg gccaacctga ctggcaaagt   900
gtggatcgcc tccgaagact gggccatctc cacgtacatc accaatgtgc ccgggatcca   960
gggcattggg acggtgctgg gggtggccat ccagcagaga caagtccctg gcctgaagga   1020
gtttgaagag tcctatgtcc aggcagtgat gggtgctccc agaacttgcc cagaggggtc   1080
ctggtgcggc actaaccagc tgtgcaggga gtgtcacgct tcacgacat ggaacatgcc    1140 cgagcttgga gccttctcca tgagcgctgc ctacaatgtg tatgaggctg tgtatgctgt   1200
ggcccacggc ctccaccagc tcctgggatg tacctctggg acctgtgcca gaggcccagt   1260
```

```
ctacccctgg cagcttcttc agcagatcta caaggtgaat ttccttctac ataagaagac    1320
tgtagcattc gatgacaagg gggaccctct aggttattat gacatcatcg cctgggactg    1380
gaatggacct gaatggacct ttgaggtcat tggttctgcc tcactgtctc cagttcatct    1440
agacataaat aagacaaaaa tccagtggca cgggaagaac aatcaggtgc ctgtgtcagt    1500
gtgtaccagg gactgtctcg aagggcacca caggttggtc atgggttccc accactgctg    1560
cttcgagtgc atgccctgtg aagctgggac atttctcaac acgagtgagc ttcacacctg    1620
ccagccttgt ggaacagaag aatgggcccc tgaggggagc tcagcctgct tctcacgcac    1680
cgtggagttc ttggggtggc atgaacccat ctctttggtg ctattagcag ctaacacgct    1740
attgctgctg ctgctgattg ggactgctgg cctgtttgcc tggcgtcttc acacgcctgt    1800
tgtgaggtca gctgggggta ggctgtgctt cctcatgctg ggttccttgg tagctgggag    1860
ttgcagcctc tacagcttct tcgggaagcc cacggtgccc gcgtgcttgc tgcgtcagcc    1920
cctcttttct ctcgggtttg ccattttcct tcctgtctg acaatccgct ccttccaact    1980
ggtcatcatc ttcaagtttt ctaccaaggt acccacattc taccacactt gggcccaaaa    2040
ccatggtgcc ggaatattcg tcattgtcag ctccacggtc catttgttcc tctgtctcac    2100
gtggcttgca atgtggaccc cacggcccac cagggagtac cagcgcttcc cccatctggt    2160
gattcttgag tgcacagagg tcaactctgt gggcttcctg gtggctttcg cacacaacat    2220
cctcctctcc atcagcacct ttgtctgcag ctacctgggt aaggaactgc cggagaacta    2280
taacgaagcc aaatgtgtca ccttcagcct gctcctccac ttcgtatcct ggatcgcttt    2340
cttcaccatg tccagcattt accagggcag ctacctaccc gcggtcaatg tgctggcagg    2400
gctggccact ctgagtggcg gcttcagcgg ctatttcctc cctaaatgct acgtgattct    2460
ctgccgtcca gaactcaaca acacagaaca ctttcaggcc tccatccagg actacacgag    2520
gcgctgcggc actacctgag gcgctgcggc actacctgag gcgctgcggc actacctga    2579

<210> SEQ ID NO 6
<211> LENGTH: 2333
<212> TYPE: DNA
<213> ORGANISM: Homo sapiens
<220> FEATURE:
<223> OTHER INFORMATION: human T1R1 G-protein coupled receptor sweet
      taste receptor

<400> SEQUENCE: 6
aggtcttgta gcttcaatga gcatggctac cacctcttcc aggctatgcg gcttggggtt      60
gaggagataa acaactccac ggccctgctg cccaacatca cctgggggta ccagctgtat    120
gatgtgtgtt ctgactctgc caatgtgtat gccacgctga gagtgctctc cctgccaggg    180
caacaccaca tagagctcca aggagacctt ctccactatt cccctacggt gctggcagtg    240
attgggcctg acagcaccaa ccgtgctgcc accacagccg ccctgctgag ccctttcctg    300
gtgcatatta gctatgcggc cagcagcgag acgctcagcg tgaagcggca gtatccctct    360
ttcctgcgca ccatccccaa tgacaagtac caggtggaga ccatggtgct gctgctgcag    420
aagttcgggt ggacctggat ctctctggtt ggcagcagtg acgactatgg gcagctaggg    480
gtgcaggcac tggagaacca ggccctggtc aggggcatct gcattgcttt caaggacatc    540
atgcccttct ctgcccaggt gggcgatgag aggatgcagt gcctcatgcg ccacctggcc    600
caggccgggg ccaccgtcgt ggttgttttt tccagccgcc agttggccag ggtgtttttc    660
gagtccgtgt tgctgaccaa cctgactggc aagtgtgggg tcgcctcaga agcctgggcc    720
ctctccaggc acatcactgg ggtgcccggg atccagcgca ttgggatggt gctgggcgtg    780
```

```
gccatccaga agagggctgt ccctggcctg aaggcgtttg aagaagccta tgcccgggca    840
gacaaggagg cccctaggcc ttgcacaagg ctcctggtg cagcagcaat cagctctgca     900
gagaatgcca agctttcatg gcacacacga tgcccaagct caaagccttc tccatgagtt    960
ctgcctacaa cgcataccgg gctgtgtatg cggtggccca tggcctccac cagctcctgg   1020
gctgtgcctc tgagctctgt tccaggggcc gagtctaccc ctggcagctt ttggagcaga   1080
tccacaaggt gcatttcctt ctacacaagg acactgtggc gtttaatgac aacagagatc   1140
ccctcagtag ctataacata attgcctggg actggaatgg acccaagtgg accttcacgg   1200
tcctcggttc ctccacatgg tctccagttc agctaaacat aaatgagacc aaaatccagt   1260
ggcacggaaa gaaccaccag gtgcctaagt ctgtgtgttc cagcgactgt cttgaagggc   1320
accagcgagt ggttacgggt ttccatcact gctgctttga gtgtgtgccc tgtggggctg   1380
ggaccttcct caacaagagc gagctctaca gatgccagcc ttgtggaaca gaagagtggg   1440
cacctgaggg aagccagacc tgcttcccgc gcactgtggt gttttttggct ttgcgtgagc   1500
acacctcttg ggtgctgctg gcagctaaca cgctgctgct gctgctgctg cttgggactg   1560
ctggcctgtt tgcctggcac ctagacaccc ctgtggtgag gtcagcaggg ggccgcctgt   1620
gctttcttat gctgggctcc ctggcagcag gtagtggcag cctctatggc ttctttgggg   1680
aacccacaag gcctgcgtgc ttgctacgcc aggccctctt tgcccttggt ttcaccatct   1740
tcctgtcctg cctgacagtt cgctcattcc aactaatcat catcttcaag ttttccacca   1800
aggtacctac attctaccac gcctgggtcc aaaaccacgg tgctggcctg tttgtgatga   1860
tcagctcagc ggcccagctg cttatctgtc taacttggct ggtggtgtgg accccactgc   1920
ctgctaggga ataccagcgc ttcccccatc tggtgatgct tgagtgcaca gagaccaact   1980
ccctgggctt catactggcc ttcctctaca atggcctcct ctccatcagt gcctttgcct   2040
gcagctacct gggtaaggac ttgccagaga actacaacga ggccaaatgt gtcaccttca   2100
gcctgctctt caacttcgtg tcctggatcg ccttcttcac cacggccagc gtctacgacg   2160
gcaagtacct gcctgcggcc aacatgatgg ctgggctgag cagcctgagc agcggcttcg   2220
gtgggtattt tctgcctaag tgctacgtga tcctctgccg cccagacctc aacagcacag   2280
agcacttcca ggcctccatt caggactaca cgaggcgctg cggctccacc tga           2333
```

<210> SEQ ID NO 7
<211> LENGTH: 843
<212> TYPE: PRT
<213> ORGANISM: Rattus sp.
<220> FEATURE:
<223> OTHER INFORMATION: rat T1R2 G-protein coupled receptor sweet
taste receptor

<400> SEQUENCE: 7

Met Gly Pro Gln Ala Arg Thr Leu Cys Leu Leu Ser Leu Leu Leu His
1               5                   10                  15

Val Leu Pro Lys Pro Gly Lys Leu Val Glu Asn Ser Asp Phe His Leu
            20                  25                  30

Ala Gly Asp Tyr Leu Leu Gly Gly Leu Phe Thr Leu His Ala Asn Val
        35                  40                  45

Lys Ser Ile Ser His Leu Ser Tyr Leu Gln Val Pro Lys Cys Asn Glu
    50                  55                  60

Phe Thr Met Lys Val Leu Gly Tyr Asn Leu Met Gln Ala Met Arg Phe
65                  70                  75                  80

Ala Val Glu Glu Ile Asn Asn Cys Ser Ser Leu Leu Pro Gly Val Leu

```
                  85                  90                  95
Leu Gly Tyr Glu Met Val Asp Val Cys Tyr Leu Ser Asn Asn Ile His
                100                 105                 110
Pro Gly Leu Tyr Phe Leu Ala Gln Asp Asp Leu Leu Pro Ile Leu
                115                 120                 125
Lys Asp Tyr Ser Gln Tyr Met Pro His Val Val Ala Val Ile Gly Pro
                130                 135                 140
Asp Asn Ser Glu Ser Ala Ile Thr Val Ser Asn Ile Leu Ser His Phe
145                 150                 155                 160
Leu Ile Pro Gln Ile Thr Tyr Ser Ala Ile Ser Asp Lys Leu Arg Asp
                165                 170                 175
Lys Arg His Phe Pro Ser Met Leu Arg Thr Val Pro Ser Ala Thr His
                180                 185                 190
His Ile Glu Ala Met Val Gln Leu Met Val His Phe Gln Trp Asn Trp
                195                 200                 205
Ile Val Val Leu Val Ser Asp Asp Tyr Gly Arg Glu Asn Ser His
                210                 215                 220
Leu Leu Ser Gln Arg Leu Thr Lys Thr Ser Asp Ile Cys Ile Ala Phe
225                 230                 235                 240
Gln Glu Val Leu Pro Ile Pro Glu Ser Ser Gln Val Met Arg Ser Glu
                245                 250                 255
Glu Gln Arg Gln Leu Asp Asn Ile Leu Asp Lys Leu Arg Arg Thr Ser
                260                 265                 270
Ala Arg Val Val Val Phe Ser Pro Glu Leu Ser Leu Tyr Ser Phe
                275                 280                 285
Phe His Glu Val Leu Arg Trp Asn Phe Thr Gly Phe Val Trp Ile Ala
                290                 295                 300
Ser Glu Ser Trp Ala Ile Asp Pro Val Leu His Asn Leu Thr Glu Leu
305                 310                 315                 320
Arg His Thr Gly Thr Phe Leu Gly Val Thr Ile Gln Arg Val Ser Ile
                325                 330                 335
Pro Gly Phe Ser Gln Phe Arg Val Arg Arg Asp Lys Pro Gly Tyr Pro
                340                 345                 350
Val Pro Asn Thr Thr Asn Leu Arg Thr Thr Cys Asn Gln Asp Cys Asp
                355                 360                 365
Ala Cys Leu Asn Thr Thr Lys Ser Phe Asn Asn Ile Leu Ile Leu Ser
                370                 375                 380
Gly Glu Arg Val Val Tyr Ser Val Tyr Ser Ala Val Tyr Ala Val Ala
385                 390                 395                 400
His Ala Leu His Arg Leu Leu Gly Cys Asn Arg Val Arg Cys Thr Lys
                405                 410                 415
Gln Lys Val Tyr Pro Trp Gln Leu Leu Arg Glu Ile Trp His Val Asn
                420                 425                 430
Phe Thr Leu Leu Gly Asn Arg Leu Phe Phe Asp Gln Gln Gly Asp Met
                435                 440                 445
Pro Met Leu Leu Asp Ile Ile Gln Trp Gln Trp Asp Leu Ser Gln Asn
                450                 455                 460
Pro Phe Gln Ser Ile Ala Ser Tyr Ser Pro Thr Ser Lys Arg Leu Thr
465                 470                 475                 480
Tyr Ile Asn Asn Val Ser Trp Tyr Thr Pro Asn Asn Thr Val Pro Val
                485                 490                 495
Ser Met Cys Ser Lys Ser Cys Gln Pro Gly Gln Met Lys Lys Ser Val
                500                 505                 510
```

-continued

```
Gly Leu His Pro Cys Cys Phe Glu Cys Leu Asp Cys Met Pro Gly Thr
            515                 520                 525

Tyr Leu Asn Arg Ser Ala Asp Glu Phe Asn Cys Leu Ser Cys Pro Gly
        530                 535                 540

Ser Met Trp Ser Tyr Lys Asn Asp Ile Thr Cys Phe Gln Arg Arg Pro
545                 550                 555                 560

Thr Phe Leu Glu Trp His Glu Val Pro Thr Ile Val Val Ala Ile Leu
                565                 570                 575

Ala Ala Leu Gly Phe Phe Ser Thr Leu Ala Ile Leu Phe Ile Phe Trp
            580                 585                 590

Arg His Phe Gln Thr Pro Met Val Arg Ser Ala Gly Gly Pro Met Cys
        595                 600                 605

Phe Leu Met Leu Val Pro Leu Leu Leu Ala Phe Gly Met Val Pro Val
610                 615                 620

Tyr Val Gly Pro Pro Thr Val Phe Ser Cys Phe Cys Arg Gln Ala Phe
625                 630                 635                 640

Phe Thr Val Cys Phe Ser Ile Cys Leu Ser Cys Ile Thr Val Arg Ser
                645                 650                 655

Phe Gln Ile Val Cys Val Phe Lys Met Ala Arg Arg Leu Pro Ser Ala
            660                 665                 670

Tyr Ser Phe Trp Met Arg Tyr His Gly Pro Tyr Val Phe Val Ala Phe
        675                 680                 685

Ile Thr Ala Ile Lys Val Ala Leu Val Val Gly Asn Met Leu Ala Thr
690                 695                 700

Thr Ile Asn Pro Ile Gly Arg Thr Asp Pro Asp Asp Pro Asn Ile Met
705                 710                 715                 720

Ile Leu Ser Cys His Pro Asn Tyr Arg Asn Gly Leu Leu Phe Asn Thr
                725                 730                 735

Ser Met Asp Leu Leu Leu Ser Val Leu Gly Phe Ser Phe Ala Tyr Met
            740                 745                 750

Gly Lys Glu Leu Pro Thr Asn Tyr Asn Glu Ala Lys Phe Ile Thr Leu
        755                 760                 765

Ser Met Thr Phe Ser Phe Thr Ser Ser Ile Ser Leu Cys Thr Phe Met
770                 775                 780

Ser Val His Asp Gly Val Leu Val Thr Ile Met Asp Leu Leu Val Thr
785                 790                 795                 800

Val Leu Asn Phe Leu Ala Ile Gly Leu Gly Tyr Phe Gly Pro Lys Cys
                805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
        835                 840
```

<210> SEQ ID NO 8
<211> LENGTH: 843
<212> TYPE: PRT
<213> ORGANISM: Mus sp.
<220> FEATURE:
<223> OTHER INFORMATION: mouse T1R2 G-protein coupled receptor sweet
      taste receptor

<400> SEQUENCE: 8

```
Met Gly Pro Gln Ala Arg Thr Leu His Leu Leu Phe Leu Leu Leu His
1               5                   10                  15

Ala Leu Pro Lys Pro Val Met Leu Val Gly Asn Ser Asp Phe His Leu
            20                  25                  30
```

```
Ala Gly Asp Tyr Leu Leu Gly Gly Leu Phe Thr Leu His Ala Asn Val
         35                  40                  45

Lys Ser Val Ser His Leu Ser Tyr Leu Gln Val Pro Lys Cys Asn Glu
 50                  55                  60

Tyr Asn Met Lys Val Leu Gly Tyr Asn Leu Met Gln Ala Met Arg Phe
 65                  70                  75                  80

Ala Val Glu Glu Ile Asn Asn Cys Ser Ser Leu Leu Pro Gly Val Leu
                 85                  90                  95

Leu Gly Tyr Glu Met Val Asp Val Cys Tyr Leu Ser Asn Asn Ile Gln
            100                 105                 110

Pro Gly Leu Tyr Phe Leu Ser Gln Ile Asp Asp Phe Leu Pro Ile Leu
            115                 120                 125

Lys Asp Tyr Ser Gln Tyr Arg Pro Gln Val Val Ala Val Ile Gly Pro
130                 135                 140

Asp Asn Ser Glu Ser Ala Ile Thr Val Ser Asn Ile Leu Ser Tyr Phe
145                 150                 155                 160

Leu Val Pro Gln Val Thr Tyr Ser Ala Ile Thr Asp Lys Leu Gln Asp
                165                 170                 175

Lys Arg Arg Phe Pro Ala Met Leu Arg Thr Val Pro Ser Ala Thr His
            180                 185                 190

His Ile Glu Ala Met Val Gln Leu Met Val His Phe Gln Trp Asn Trp
            195                 200                 205

Ile Val Val Leu Val Ser Asp Asp Tyr Gly Arg Glu Asn Ser His
210                 215                 220

Leu Leu Ser Gln Arg Leu Thr Asn Thr Gly Asp Ile Cys Ile Ala Phe
225                 230                 235                 240

Gln Glu Val Leu Pro Val Pro Glu Pro Asn Gln Ala Val Arg Pro Glu
                245                 250                 255

Glu Gln Asp Gln Leu Asp Asn Ile Leu Asp Lys Leu Arg Arg Thr Ser
            260                 265                 270

Ala Arg Val Val Val Ile Phe Ser Pro Glu Leu Ser Leu His Asn Phe
            275                 280                 285

Phe Arg Glu Val Leu Arg Trp Asn Phe Thr Gly Phe Val Trp Ile Ala
            290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg His Asp Lys Pro Gly Tyr Arg
            340                 345                 350

Met Pro Asn Glu Thr Ser Leu Arg Thr Thr Cys Asn Gln Asp Cys Asp
            355                 360                 365

Ala Cys Met Asn Ile Thr Glu Ser Phe Asn Asn Val Leu Met Leu Ser
370                 375                 380

Gly Glu Arg Val Val Tyr Ser Val Tyr Ser Ala Val Tyr Ala Val Ala
385                 390                 395                 400

His Thr Leu His Arg Leu Leu His Cys Asn Gln Val Arg Cys Thr Lys
                405                 410                 415

Gln Ile Val Tyr Pro Trp Gln Leu Leu Arg Glu Ile Trp His Val Asn
            420                 425                 430

Phe Thr Leu Leu Gly Asn Gln Leu Phe Phe Asp Glu Gln Gly Asp Met
            435                 440                 445

Pro Met Leu Leu Asp Ile Ile Gln Trp Gln Trp Gly Leu Ser Gln Asn
450                 455                 460
```

```
Pro Phe Gln Ser Ile Ala Ser Tyr Ser Pro Thr Glu Thr Arg Leu Thr
465                 470                 475                 480

Tyr Ile Ser Asn Val Ser Trp Tyr Thr Pro Asn Asn Thr Val Pro Ile
            485                 490                 495

Ser Met Cys Ser Lys Ser Cys Gln Pro Gly Gln Met Lys Lys Pro Ile
        500                 505                 510

Gly Leu His Pro Cys Cys Phe Glu Cys Val Asp Cys Pro Pro Asp Thr
            515                 520                 525

Tyr Leu Asn Arg Ser Val Asp Glu Phe Asn Cys Leu Ser Cys Pro Gly
        530                 535                 540

Ser Met Trp Ser Tyr Lys Asn Asn Ile Ala Cys Phe Lys Arg Arg Leu
545                 550                 555                 560

Ala Phe Leu Glu Trp His Glu Val Pro Thr Ile Val Val Thr Ile Leu
                565                 570                 575

Ala Ala Leu Gly Phe Ile Ser Thr Leu Ala Ile Leu Leu Ile Phe Trp
            580                 585                 590

Arg His Phe Gln Thr Pro Met Val Arg Ser Ala Gly Gly Pro Met Cys
        595                 600                 605

Phe Leu Met Leu Val Pro Leu Leu Ala Phe Gly Met Val Pro Val
610                 615                 620

Tyr Val Gly Pro Pro Thr Val Phe Ser Cys Phe Cys Arg Gln Ala Phe
625                 630                 635                 640

Phe Thr Val Cys Phe Ser Val Cys Leu Ser Cys Ile Thr Val Arg Ser
                645                 650                 655

Phe Gln Ile Val Cys Val Phe Lys Met Ala Arg Arg Leu Pro Ser Ala
            660                 665                 670

Tyr Gly Phe Trp Met Arg Tyr His Gly Pro Tyr Val Phe Val Ala Phe
        675                 680                 685

Ile Thr Ala Val Lys Val Ala Leu Val Ala Gly Asn Met Leu Ala Thr
690                 695                 700

Thr Ile Asn Pro Ile Gly Arg Thr Asp Pro Asp Asp Pro Asn Ile Ile
705                 710                 715                 720

Ile Leu Ser Cys His Pro Asn Tyr Arg Asn Gly Leu Leu Phe Asn Thr
                725                 730                 735

Ser Met Asp Leu Leu Leu Ser Val Leu Gly Phe Ser Phe Ala Tyr Val
            740                 745                 750

Gly Lys Glu Leu Pro Thr Asn Tyr Asn Glu Ala Lys Phe Ile Thr Leu
        755                 760                 765

Ser Met Thr Phe Ser Phe Thr Ser Ser Ile Ser Leu Cys Thr Phe Met
770                 775                 780

Ser Val His Asp Gly Val Leu Val Thr Ile Met Asp Leu Leu Val Thr
785                 790                 795                 800

Val Leu Asn Phe Leu Ala Ile Gly Leu Gly Tyr Phe Gly Pro Lys Cys
                805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
        835                 840

<210> SEQ ID NO 9
<211> LENGTH: 838
<212> TYPE: PRT
<213> ORGANISM: Homo sapiens
<220> FEATURE:
<223> OTHER INFORMATION: human T1R2 G-protein coupled receptor sweet
``` taste receptor

<400> SEQUENCE: 9

```
Met Gly Pro Arg Ala Lys Thr Ile Cys Ser Leu Phe Phe Leu Leu Trp
 1               5                  10                  15

Val Leu Ala Glu Pro Ala Glu Asn Ser Asp Phe Tyr Leu Pro Gly Asp
             20                  25                  30

Tyr Leu Leu Gly Gly Leu Phe Ser Leu His Ala Asn Met Lys Gly Ile
         35                  40                  45

Val His Leu Asn Phe Leu Gln Val Pro Met Cys Lys Glu Tyr Glu Val
     50                  55                  60

Lys Val Ile Gly Tyr Asn Leu Met Gln Ala Met Arg Phe Ala Val Glu
 65                  70                  75                  80

Glu Ile Asn Asn Asp Ser Ser Leu Leu Pro Gly Val Leu Leu Gly Tyr
                 85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
            340                 345                 350

Thr Ser Gln Ser Tyr Thr Cys Asn Gln Glu Cys Asp Asn Cys Leu Asn
        355                 360                 365

Ala Thr Leu Ser Phe Asn Thr Ile Leu Arg Leu Ser Gly Glu Arg Val
    370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
```

-continued

```
                405                 410                 415
Pro Trp Gln Leu Leu Glu Glu Ile Trp Lys Val Asn Phe Thr Leu Leu
            420                 425                 430
Asp His Gln Ile Phe Phe Asp Pro Gln Gly Asp Val Ala Leu His Leu
            435                 440                 445
Glu Ile Val Gln Trp Gln Trp Asp Arg Ser Gln Asn Pro Phe Gln Ser
450                 455                 460
Val Ala Ser Tyr Tyr Pro Leu Gln Arg Gln Leu Lys Asn Ile Gln Asp
465                 470                 475                 480
Ile Ser Trp His Thr Val Asn Asn Thr Ile Pro Met Ser Met Cys Ser
            485                 490                 495
Lys Arg Cys Gln Ser Gly Gln Lys Lys Pro Val Gly Ile His Val
            500                 505                 510
Cys Cys Phe Glu Cys Ile Asp Cys Leu Pro Gly Thr Phe Leu Asn His
            515                 520                 525
Thr Glu Asp Glu Tyr Glu Cys Gln Ala Cys Pro Asn Asn Glu Trp Ser
            530                 535                 540
Tyr Gln Ser Glu Thr Ser Cys Phe Lys Arg Gln Leu Val Phe Leu Glu
545                 550                 555                 560
Trp His Glu Ala Pro Thr Ile Ala Val Ala Leu Leu Ala Ala Leu Gly
            565                 570                 575
Phe Leu Ser Thr Leu Ala Ile Leu Val Ile Phe Trp Arg His Phe Gln
            580                 585                 590
Thr Pro Ile Val Arg Ser Ala Gly Gly Pro Met Cys Phe Leu Met Leu
            595                 600                 605
Thr Leu Leu Leu Val Ala Tyr Met Val Val Pro Val Tyr Val Gly Pro
            610                 615                 620
Pro Lys Val Ser Thr Cys Leu Cys Arg Gln Ala Leu Phe Pro Leu Cys
625                 630                 635                 640
Phe Thr Ile Cys Ile Ser Cys Ile Ala Val Arg Ser Phe Gln Ile Val
            645                 650                 655
Cys Ala Phe Lys Met Ala Ser Arg Phe Pro Arg Ala Tyr Ser Tyr Trp
            660                 665                 670
Val Arg Tyr Gln Gly Pro Tyr Val Ser Met Ala Phe Ile Thr Val Leu
            675                 680                 685
Lys Met Val Ile Val Val Ile Gly Met Leu Ala Arg Pro Gln Ser His
            690                 695                 700
Pro Arg Thr Asp Pro Asp Asp Pro Lys Ile Thr Ile Val Ser Cys Asn
705                 710                 715                 720
Pro Asn Tyr Arg Asn Ser Leu Leu Phe Asn Thr Ser Leu Asp Leu Leu
            725                 730                 735
Leu Ser Val Val Gly Phe Ser Phe Ala Tyr Met Gly Lys Glu Leu Pro
            740                 745                 750
Thr Asn Tyr Asn Glu Ala Lys Phe Ile Thr Leu Ser Met Thr Phe Tyr
            755                 760                 765
Phe Thr Ser Ser Val Ser Leu Cys Thr Phe Met Ser Ala Tyr Ser Gly
            770                 775                 780
Val Leu Val Thr Ile Val Asp Leu Leu Val Thr Val Leu Asn Leu Leu
785                 790                 795                 800
Ala Ile Ser Leu Gly Tyr Phe Gly Pro Lys Cys Tyr Met Ile Leu Phe
            805                 810                 815
Tyr Pro Glu Arg Asn Thr Pro Ala Tyr Phe Asn Ser Met Ile Gln Gly
            820                 825                 830
```

Tyr Thr Met Arg Arg Asp
    835

<210> SEQ ID NO 10
<211> LENGTH: 2993
<212> TYPE: DNA
<213> ORGANISM: Rattus sp.
<220> FEATURE:
<223> OTHER INFORMATION: rat T1R2 G-protein coupled receptor sweet
      taste receptor

<400> SEQUENCE: 10

| | | | | | |
|---|---|---|---|---|---|
| cactttgctg | tcatgggtcc | ccaggcaagg | acactctgct | tgctgtctct | cctgctgcat | 60 |
| gttctgccta | agccaggcaa | gctggtagag | aactctgact | tccacctggc | cggggactac | 120 |
| ctcctgggtg | gcctctttac | cctccatgcc | aacgtgaaga | gcatctccca | cctcagctac | 180 |
| ctgcaggtgc | ccaagtgcaa | tgagttcacc | atgaaggtgt | gggctacaa | cctcatgcag | 240 |
| gccatgcgtt | tcgctgtgga | ggagatcaac | aactgtagct | ccctgctacc | cggcgtgctg | 300 |
| ctcggctacg | agatggtgga | tgtctgttac | ctctccaaca | atatccaccc | tgggctctac | 360 |
| ttcctggcac | aggacgacga | cctcctgccc | atcctcaaag | actacagcca | gtacatgccc | 420 |
| cacgtggtgg | ctgtcattgg | ccccgacaac | tctgagtccg | ccattaccgt | gtccaacatt | 480 |
| ctctctcatt | tcctcatccc | acagatcaca | tacagcgcca | tctccgacaa | gctgcgggac | 540 |
| aagcggcact | tccctagcat | gctacgcaca | gtgcccagcg | ccacccacca | catcgaggcc | 600 |
| atggtgcagc | tgatggttca | cttccaatgg | aactggattg | tggtgctggt | gagcgacgac | 660 |
| gattacggcc | gcgagaacag | ccacctgttg | agccagcgtc | tgaccaaaac | gagcgacatc | 720 |
| tgcattgcct | tccaggaggt | tctgcccata | cctgagtcca | gccaggtcat | gaggtccgag | 780 |
| gagcagagac | aactggacaa | catcctggac | aagctgcggc | ggacctcggc | gcgcgtcgtg | 840 |
| gtggtgttct | cgcccgagct | gagcctgtat | agcttctttc | acgaggtgct | ccgctggaac | 900 |
| ttcacgggtt | ttgtgtggat | cgcctctgag | tcctgggcta | tcgacccagt | tctgcataac | 960 |
| ctcacggagc | tgcgccacac | gggtactttt | ctgggcgtca | ccatccagag | ggtgtccatc | 1020 |
| cctggcttca | gtcagttccg | agtgcgccgt | gacaagccag | ggtatcccgt | gcctaacacg | 1080 |
| accaacctgc | ggacgacctg | caaccaggac | tgtgacgcct | gcttgaacac | caccaagtcc | 1140 |
| ttcaacaaca | tccttatact | ttcgggggag | cgcgtggtct | acagcgtgta | ctcggcagtt | 1200 |
| tacgcggtgg | cccatgccct | ccacagactc | ctcggctgta | accgggtccg | ctgcaccaag | 1260 |
| caaaaggtct | accccgtggca | gctactcagg | gagatctggc | acgtcaactt | cacgctcctg | 1320 |
| ggtaaccggc | tcttctttga | ccaacaaggg | gacatgccga | tgctcttgga | catcatccag | 1380 |
| tggcagtggg | acctgagcca | gaatcccttc | caaagcatcg | cctcctattc | cccaccagc | 1440 |
| aagaggctaa | cctacattaa | caatgtgtcc | tggtacaccc | caacaacac | ggtccctgtc | 1500 |
| tccatgtgtt | ccaagagctg | ccagccaggg | caaatgaaaa | agtctgtggg | cctccacccct | 1560 |
| tgttgcttcg | agtgcttgga | ttgtatgcca | ggcacctacc | tcaaccgctc | agcagatgag | 1620 |
| tttaactgtc | tgtcctgccc | gggttccatg | tggtcctaca | agaacgacat | cacttgcttc | 1680 |
| cagcggcggc | ctaccttcct | ggagtggcac | gaagtgccca | ccatcgtggt | ggccatactg | 1740 |
| gctgccctgg | gcttcttcag | tacactggcc | attcttttca | tcttctggag | acatttccag | 1800 |
| acacccatgg | tgcgctcggc | cggtggcccc | atgtgcttcc | tgatgctcgt | gcccctgctg | 1860 |
| ctggcgtttg | ggatggtgcc | cgtgtatgtg | gggccccca | cggtcttctc | atgcttctgc | 1920 |
| cgacaggctt | tcttcaccgt | ctgcttctcc | atctgcctat | cctgcatcac | cgtgcgctcc | 1980 |

-continued

| | |
|---|---|
| ttccagatcg tgtgtgtctt caagatggcc agacgcctgc caagtgccta cagttttttgg | 2040 |
| atgcgttacc acgggccta tgtcttcgtg gccttcatca cggccatcaa ggtggccctg | 2100 |
| gtggtgggca acatgctggc caccaccatc aaccccattg ccggaccga cccggatgac | 2160 |
| cccaacatca tgatcctctc gtgccaccct aactaccgca acgggctact gttcaacacc | 2220 |
| agcatggact tgctgctgtc tgtgctgggt ttcagcttcg cttacatggg caaggagctg | 2280 |
| cccaccaact acaacgaagc caagttcatc actctcagca tgaccttctc cttcacctcc | 2340 |
| tccatctccc tctgcacctt catgtctgtg cacgacggcg tgctggtcac catcatggac | 2400 |
| ctcctggtca ctgtgctcaa cttcctggcc atcggcttgg gatactttgg ccccaagtgt | 2460 |
| tacatgatcc tttctaccc ggagcgcaac acctcagcct atttcaatag catgatccag | 2520 |
| ggctacacca tgaggaagag ctagctccgc ccaccggcct cagcagcaga gccccggcc | 2580 |
| acgttaatgg tgttcctctg ccattctctg cagcgtagct attttaccc acatagcgct | 2640 |
| taaaataccc atgatgcact ctcccccgac ccccaagcca tttcactggc caggacctac | 2700 |
| cacccactta tagatgaaac caccaaggcg ccctatgggg ctccaaggat ggcctaccac | 2760 |
| tgccatctgg tggtcacagt gagcacatgc gggccgtggc ccatggctcc cagccagctg | 2820 |
| gtggctagtg gctgtgaggc cagatgtctg tgtatctgag ttcctgggaa gcagagactg | 2880 |
| gggctcctgt gttctaatgg tcagatgggc atcatgggcc cttcattatt gcttacgaat | 2940 |
| aaacttccct ccggtgaaaa aaaaaaaaa aaaaaaaaa aaaaaaaaa aaa | 2993 |

<210> SEQ ID NO 11
<211> LENGTH: 2532
<212> TYPE: DNA
<213> ORGANISM: Mus sp.
<220> FEATURE:
<223> OTHER INFORMATION: mouse T1R2 G-protein coupled receptor sweet
      taste receptor

<400> SEQUENCE: 11

| | |
|---|---|
| atgggacccc aggcgaggac actccatttg ctgtttctcc tgctgcatgc tctgcctaag | 60 |
| ccagtcatgc tggtagggaa ctccgacttt cacctggctg gggactacct cctgggtggc | 120 |
| ctctttaccc tccatgccaa cgtgaagagt gtctctcacc tcagctacct gcaggtgccc | 180 |
| aagtgcaatg agtacaacat gaaggtgttg ggctacaacc tcatgcaggc catgcgattc | 240 |
| gccgtggagg aaatcaacaa ctgtagctct ttgctgcccg gcgtgctgct cggctacgag | 300 |
| atggtggatg tctgctacct ctccaacaat atccagcctg gctctacttt cctgtcacag | 360 |
| atagatgact tcctgcccat cctcaaagac tacagccagt acaggcccca gtggtggct | 420 |
| gttattggcc cagacaactc tgagtctgcc atcaccgtgt ccaacattct ctcctacttc | 480 |
| ctcgtgccac aggtcacata tagcgccatc accgacaagc tgcaagacaa gcggcgcttc | 540 |
| cctgccatgc tgcgcactgt gcccagcgcc acccaccaca tcgaggccat ggtgcaactg | 600 |
| atggttcact tccagtggaa ctggatcgtg gtgctggtga gcgatgacga ttatggccga | 660 |
| gagaacagcc acctgctgag ccagcgtctg accaacactg cgacatctg cattgccttc | 720 |
| caggaggttc tgcccgtacc agaacccaac caggctgtga ggcctgagga gcaggaccaa | 780 |
| ctggacaaca tcctggacaa gctgcggcgg acttcggcgc gtgtggtggt gatattctcg | 840 |
| ccggagctga gcctgcacaa cttcttccgt gaggtgctgc gctggaactt cacgggcttt | 900 |
| gtgtggattg cctctgagtc ctgggccatc gaccctgttc tacacaacct cacagagctg | 960 |
| cgccacacgg gcactttcct gggtgtcacc atccagaggg tgtccatccc tggcttcagc | 1020 |
| cagttccgag tgcgccatga caagccaggg tatcgcatgc taacgagac cagcctgcgg | 1080 |

```
actacctgta accaggactg cgacgcctgc atgaacatca ctgagtcctt caacaacgtt   1140
ctcatgcttt cggggagcg tgtggtctac agcgtgtact cggccgtcta cgcggtggcc   1200 cacacccctcc acagactcct ccactgcaat caggtccgct gcaccaagca aatcgtctat   1260
ccatggcagc tactcaggga gatctggcat gtcaacttca cgctcctggg caaccagctc   1320
ttcttcgacg aacaagggga catgccgatg ctcctggaca tcatccagtg gcagtggggc   1380
ctgagccaga acccccttcca aagcatcgcc tcctactccc ccaccgagac gaggctgacc   1440
tacattagca atgtgtcctg gtacaccccc aacaacacgg tccccatatc catgtgttct   1500
aagagttgcc agcctgggca aatgaaaaaa cccataggcc tccacccatg ctgcttcgag   1560
tgtgtggact gtccgccgga cacctacctc aaccgatcag tagatgagtt taactgtctg   1620
tcctgcccgg gttccatgtg gtcttacaag aacaacatcg cttgcttcaa gcggcggctg   1680
gccttcctgg agtggcacga agtgcccact atcgtggtga ccatcctggc cgccctgggc   1740
ttcatcagta cgctggccat tctgctcatc ttctggagac atttccagac gcccatggtg   1800
cgctcggcgg cggcccccat gtgcttcctg atgctggtgc cctgctgct ggcgttcggg   1860 atggtccccg tgtatgtggg cccccccacg gtcttctcct gtttctgccg ccaggctttc   1920
ttcaccgttt gcttctccgt ctgcctctcc tgcatcacgg tgcgctcctt ccagattgtg   1980
tgcgtcttca agatggccag acgcctgcca agcgcctacg tttctggat gcgttaccac   2040 gggccctacg tcttcgtggc cttcatcacg gccgtcaagg tggccctggt ggcgggcaac   2100
atgctggcca ccaccatcaa ccccattggc cggaccgacc ccgatgaccc caatatcata   2160
atcctctcct gccaccctaa ctaccgcaac gggctactct tcaacaccag catggacttg   2220
ctgctgtccg tgctgggttt cagcttcgcg tacgtgggca aggaactgcc caccaactac   2280
aacgaagcca agttcatcac cctcagcatg accttctcct tcacctcctc catctccctc   2340
tgcacgttca gtgtctgtcca cgatggcgtg ctggtcacca tcatggattc cctggtcact   2400
gtgctcaact ttctggccat cggcttgggg tactttggcc ccaaatgtta catgatcctt   2460 ttctaccegg agcgcaacac ttcagcttat ttcaatagca tgattcaggg ctacacgatg   2520
aggaagagct ag                                                      2532
```

<210> SEQ ID NO 12
<211> LENGTH: 2010
<212> TYPE: DNA
<213> ORGANISM: Homo sapiens
<220> FEATURE:
<223> OTHER INFORMATION: human T1R2 G-protein coupled receptor sweet
      taste receptor

<400> SEQUENCE: 12

```
atcacctaca gcgccatcag cgatgagctg cgagacaagg tgcgcttccc ggctttgctg    60
cgtaccacac ccagcgccga ccaccacgtc gaggccatgg tgcagctgat gctgcacttc    120
cgctggaact ggatcattgt gctggtgagc agcgacacct atggccgcga caatggccag    180
ctgcttggcg agcgcgtggc ccggcgcgac atctgcatcg ccttccagga gacgctgccc    240
acactgcagc ccaaccagaa catgacgtca gaggagcgcc agcgcctggt gaccattgtg    300
gacaagctgc agcagagcac agcgcgcgtc gtggtcgtgt tctcgcccga cctgaccctg    360 taccactttct tcaatgaggt gctgcgccag aacttcacgg gcgccgtgtg gatcgcctcc    420
gagtcctggg ccatcgaccc ggtcctgcac aacctcacgg agctgggcca cttgggcacc    480
ttcctgggca tcaccatcca gagcgtgccc atcccgggct tcagtgagtt ccgcgagtgg    540
```

```
ggcccacagg ctgggccgcc acccctcagc aggaccagcc agagctatac ctgcaaccag     600
gagtgcgaca actgcctgaa cgccaccttg tccttcaaca ccattctcag gctctctggg     660
gagcgtgtcg tctacagcgt gtactctgcg gtctatgctg tggcccatgc cctgcacagc     720
ctcctcggct gtgacaaaag cacctgcacc aagagggtgg tctaccccctg gcagctgctt    780 gaggagatct ggaaggtcaa cttcactctc ctggaccacc aaatcttctt cgacccgcaa     840
ggggacgtgg ctctgcactt ggagattgtc cagtggcaat gggaccggag ccagaatccc     900
ttccagagcg tcgcctccta ctaccccctg cagcgacagc tgaagaacat caagacatct     960
ctgcacaccg tcaacaacac gatccctatg tccatgtgtt ccaagaggtg ccagtcaggg    1020
caaaagaaga agcctgtggg catccacgtc tgctgcttcg agtgcatcga ctgccttccc    1080
ggcaccttcc tcaaccacac tgaatgcccg aataacgagt ggtcctacca gagtgagacc    1140
tcctgcttca gcggcagct ggtcttcctg gaatggcatg aggcacccac catcgctgtg    1200
gccctgctgg ccgccctggg cttcctcagc accctggcca tcctggtgat attctggagg    1260
cacttccaga cacccatagt tcgctcggct gggggcccca tgtgcttcct gatgctgaca    1320
ctgctgctgg tggcatacat ggtggtcccg gtgtacgtgg ggcgcccaa ggtctccacc    1380 tgcctctgcc gccaggccct cttcccctc tgcttcacaa tttgcatctc ctgtatcgcc    1440
gtgcgttctt tccagatcgt ctgcgccttc aagatggcca gccgcttccc acgcgcctac    1500
agctactggg tccgctacca ggggcctac gtctctatgg catttatcac ggtactcaaa    1560
atggtcattg tggtaattgg catgctggca cggcctcagt cccaccccg tactgacccc    1620 gatgacccca agatcacaat tgtctcctgt aaccccaact accgcaacag cctgctgttc    1680
aacaccagcc tggacctgct gctctcagtg gtgggtttca gcttcgccta catgggcaaa    1740
gagctgccca ccaactacaa cgaggccaag ttcatcaccc tcagcatgac cttctatttc    1800
acctcatccg tctccctctg caccttcatg tctgcctaca gcggggtgct ggtcaccatc    1860
gtggacctct tggtcactgt gctcaacctc ctggccatca gcctgggcta cttcggcccc    1920
aagtgctaca tgatcctctt ctaccccgag cgcaacacgc ccgcctactt caacagcatg    1980
atccagggct acaccatgag gagggactag                                      2010

<210> SEQ ID NO 13
<211> LENGTH: 3200
<212> TYPE: DNA
<213> ORGANISM: Homo sapiens
<220> FEATURE:
<223> OTHER INFORMATION: human T1R3 G-protein coupled receptor sweet
      taste receptor genomic sequence

<400> SEQUENCE: 13
gctcactcca tgtgaggccc cagtcggggc agccacctgc cgtgcctgtt ggaagttgcc      60
tctgccatgc tgggccctgc tgtcctgggc ctcagcctct gggctctcct gcaccctggg     120
acgggggccc cattgtgcct gtcacagcaa cttaggatga aggggactac cgtgctgggg     180
gggctgttcc ccctgggcga ggccgaggag ctggcctcc gcagccggac acggcccagc     240
agccctgtgt gcaccaggta cagaggtggg acggcctggg tcggggtcag ggtgaccagg     300
tctggggtgc tcctgagctg ggccgaggt ggccatctgc ggttctgtgt ggccccaggt     360
tctcctcaaa cggcctgctc tgggcactgg ccatgaaaat ggccgtggag gagatcaaca     420
acaagtcgga tctgctgccc gggctgcgcc tgggctacga cctctttgat acgtgctcgg     480
agcctgtggt ggcatgaag cccagcctca tgttcctggc caaggcaggc agccgcgaca     540
tcgccgccta ctgcaactac acgcagtacc agccccgtgt gctggctgtc atcgggcccc     600
```

```
actcgtcaga gctcgccatg gtcaccggca agttcttcag cttcttcctc atgcccagg      660 tggcgccccc caccatcacc caccccacc cagccctgcc cgtgggagcc cctgtgtcag       720
gagatgcctc ttggcccttg caggtcagct acggtgctag catggagctg ctgagcgccc     780
gggagacctt cccctccttc ttccgcaccg tgcccagcga ccgtgtgcag ctgacggccg     840
ccgcggagct gctgcaggag ttcggctgga actgggtggc cgccctgggc agcgacgacg     900
agtacggccg gcagggcctg agcatcttct cggccctggc cgcggcacgc ggcatctgca     960
tcgcgcacga gggcctggtg ccgctgcccc gtgccgatga ctcgcggctg gggaaggtgc    1020
aggacgtcct gcaccaggtg aaccagagca gcgtgcaggt ggtgctgctg ttcgcctccg    1080
tgcacgccgc ccacgccctc ttcaactaca gcatcagcag caggctctcg cccaaggtgt    1140
gggtggccag cgaggcctgg ctgacctctg acctggtcat gggctgccc ggcatggccc     1200 agatgggcac ggtgcttggc ttcctccaga ggggtgccca gctgcacgag ttcccccagt    1260
acgtgaagac gcacctggcc ctggccaccg acccggcctt ctgctctgcc ctgggcgaga    1320
gggagcaggg tctggaggag gacgtggtgg gccagcgctg cccgcagtgt gactgcatca    1380
cgctgcagaa cgtgagcgca gggctaaatc accaccagac gttctctgtc tacgcagctg    1440
tgtatagcgt ggcccaggcc ctgcacaaca ctcttcagtg caacgcctca ggctgccccg    1500
cgcaggaccc cgtgaagccc tggcaggtga cccgggaga tggggggtgtg ctgtcctctg    1560 catgtgccca ggccaccagg cacggccacc acgcctgagc tggaggtggc tggcggctca    1620
gccccgtccc ccgcccgcag ctcctggaga acatgtacaa cctgaccttc cacgtgggcg    1680
ggctgccgct gcggttcgac agcagcggaa acgtggacat ggagtacgac ctgaagctgt    1740
gggtgtggca gggctcagtg cccaggctcc acgacgtggg caggttcaac ggcagcctca    1800
ggacagagcg cctgaagatc cgctggcaca cgtctgacaa ccaggtgagg tgagggtggg    1860
tgtgccaggc gtgcccgtgg tagccccgc ggcagggcgc agcctggggg tggggccgt      1920 tccagtctcc cgtgggcatg cccagccgag cagagccaga ccccaggcct gtgcgcagaa    1980
gcccgtgtcc cggtgctcgc ggcagtgcca ggagggccag gtgcgccggg tcaagggtt    2040 ccactcctgc tgctacgact gtgtggactg cgaggcgggc agctaccggc aaaacccagg    2100
tgagccgcct tcccggcagg cggggtggg aacgcagcag gggagggtcc tgccaagtcc    2160
tgactctgag accagagccc acagggtaca agacgaacac ccagcgccct tctcctctct    2220
cacagacgac atcgcctgca ccttttgtgg ccaggatgag tggtccccgg agcgaagcac    2280
acgctgcttc cgccgcaggt ctcggttcct ggcatggggc gagccggctg tgctgctgct    2340
gctcctgctg ctgagcctgg cgctgggcct tgtgctggct gctttgggc tgttcgttca    2400 ccatcgggac agcccactgg ttcaggcctc ggggggggccc ctggcctgct ttggcctggt    2460
gtgcctgggc ctggtctgcc tcagcgtcct cctgttccct ggccagccca gccctgcccg    2520
atgcctggcc cagcagccct gtcccaccct cccgctcacg gctgcctga gcacactctt    2580 cctgcaggcg gccgagatct tcgtggagtc agaactgcct ctgagctggg cagaccggct    2640
gagtggctgc tgcggggggc cctgggcctg gctggtggtg ctgctggcca tgctggtgga    2700
ggtcgcactg tgcacctggt acctggtggc cttcccgccg gaggtggtga cggactggca    2760
catgctgccc acggaggcgc tggtgcactg ccgcacacgc tcctgggtca gcttcggcct    2820
agcgcacgcc accaatgcca cgctggcctt tctctgcttc ctgggcactt tcctggtgcg    2880
gagccagccc ggctgctaca accgtgcccg tggcctcacc tttgccatgc tggcctactt    2940
catcacctgg gtctcctttg tgcccctcct ggccaatgtg caggtggtcc tcaggcccgc    3000
```

```
cgtgcagatg ggcgccctcc tgctctgtgt cctgggcatc ctggctgcct tccacctgcc    3060
caggtgttac ctgctcatgc ggcagccagg gctcaacacc cccgagttct tcctgggagg    3120
gggccctggg gatgcccaag gccagaatga cgggaacaca ggaaatcagg ggaaacatga    3180
gtgacccaac cctgtgatct                                                3200

<210> SEQ ID NO 14
<211> LENGTH: 2559
<212> TYPE: DNA
<213> ORGANISM: Homo sapiens
<220> FEATURE:
<223> OTHER INFORMATION: human T1R3 G-protein coupled receptor sweet
      taste receptor CDS

<400> SEQUENCE: 14
atgctgggcc ctgctgtcct gggcctcagc ctctgggctc tcctgcaccc tgggacgggg      60
gccccattgt gcctgtcaca gcaacttagg atgaagggggg actacgtgct ggggggggctg   120 ttccccctgg gcgaggccga ggaggctggc ctccgcagcc ggacacggcc cagcagccct    180
gtgtgcacca ggttctcctc aaacggcctg ctctgggcac tggccatgaa aatggccgtg    240
gaggagatca acaacaagtc ggatctgctg cccgggctgc gcctgggcta cgacctcttt    300
gatacgtgct ggagcctgt ggtggccatg aagcccagcc tcatgttcct ggccaaggca    360
ggcagccgcg acatcgccgc ctactgcaac tacacgcagt accagccccg tgtgctggct    420
gtcatcgggc ccactcgtc agagctgcc atggtcaccg gcaagttctt cagcttcttc    480
ctcatgcccc aggtcagcta cggtgctagc atggagctgc tgagcgcccg ggagaccttc    540
cctcccttct ccgcaccgt gcccagcgac cgtgtgcagc tgacggccgc cgcggagctg    600
ctgcaggagt cggctggaa ctgggtggcc gccctgggca gcgacgacga gtacggccgg    660
cagggcctga gcatcttctc ggccctggcc gcggcacgcg gcatctgcat cgcgcacgag    720
ggcctggtgc cgctgcccg tgccgatgac tcgcggctgg gaaggtgca ggacgtcctg    780 caccaggtga accagagcag cgtgcaggtg gtgctgctgt cgcctccgt gcacgccgcc    840 cacgccctct tcaactacag catcagcagc aggctctcgc caaggtgtg ggtggccagc    900 gaggcctggc tgacctctga cctggtcatg gggctgcccg gcatggccca gatgggcacg    960
gtgcttggct tcctccagag gggtgcccag ctgcacgagt tcccccagta cgtgaagacg   1020
cacctggccc tggccaccga cccggccttc tgctctgccc tgggcgagag ggagcagggt   1080
ctggaggagg acgtggtggg ccagcgctgc ccgcagtgtg actgcatcac gctgcagaac   1140
gtgagcgcag gctaaatca ccaccagacg ttctctgtct acgcagctgt gtatagcgtg   1200
gcccaggccc tgcacaacac tcttcagtgc aacgcctcag gctgccccgc gcaggacccc   1260
gtgaagccct ggcagctcct ggagaacatg tacaacctga ccttccacgt gggcgggctg   1320
ccgctgcggt tcgacagcag cggaaacgtg gacatggagt acgacctgaa gctgtgggtg   1380
tggcagggct cagtgcccag gctccacgac gtgggcaggt caacggcag cctcaggaca   1440 gagcgcctga gatccgctg gcacacgtct gacaaccaga gcccgtgtc cggtgctcg    1500 cggcagtgcc aggagggcca ggtgcgccgg gtcaagggggt tccactcctg ctgctacgac    1560
tgtgtggact gcgaggcggg cagctaccgg caaaacccag acgacatcgc ctgcacctc    1620 tgtggccagg atgagtggtc cccggagcga agcacacgct gcttccgccg caggtctcgg    1680
ttcctggcat ggggcgagcc ggctgtgctg ctgctgctcc tgctgctgag cctggcgctg    1740
ggccttgtgc tggctgcttt ggggctgttc gttcaccatc gggacagccc actggttcag    1800
```

-continued

```
gcctcgggggg ggcccctggc ctgctttggc ctggtgtgcc tgggcctggt ctgcctcagc    1860
gtcctcctgt tccctggcca gcccagccct gcccgatgcc tggcccagca gcccttgtcc    1920
cacctcccgc tcacgggctg cctgagcaca ctcttcctgc aggcggccga gatcttcgtg    1980
gagtcagaac tgcctctgag ctgggcagac cggctgagtg gctgcctgcg ggggccctgg    2040
gcctggctgg tggtgctgct ggccatgctg gtggaggtcg cactgtgcac ctggtacctg    2100
gtggccttcc cgccggaggt ggtgacggac tggcacatgc tgcccacgga ggcgctggtg    2160
cactgccgca cacgctcctg ggtcagcttc ggcctagcgc acgccaccaa tgccacgctg    2220
gcctttctct gcttcctggg cactttcctg gtgcggagcc agccgggctg ctacaaccgt    2280
gcccgtggcc tcacctttgc catgctggcc tacttcatca cctgggtctc ctttgtgccc    2340
ctcctggcca atgtgcaggt ggtcctcagg cccgccgtgc agatgggcgc cctcctgctc    2400
tgtgtcctgg gcatcctggc tgccttccac ctgcccaggt gttacctgct catgcggcag    2460
ccagggctca acaccccga gttcttcctg gagggggcc ctggggatgc ccaaggccag    2520
aatgacggga acacaggaaa tcaggggaaa catgagtga                           2559
```

<210> SEQ ID NO 15
<211> LENGTH: 852
<212> TYPE: PRT
<213> ORGANISM: Homo sapiens
<220> FEATURE:
<223> OTHER INFORMATION: human T1R3 G-protein coupled receptor sweet
      taste receptor

<400> SEQUENCE: 15

| Met | Leu | Gly | Pro | Ala | Val | Leu | Gly | Leu | Ser | Leu | Trp | Ala | Leu | Leu | His |
|---|---|---|---|---|---|---|---|---|---|---|---|---|---|---|---|
| 1 | | | | 5 | | | | | 10 | | | | | 15 | |

Pro Gly Thr Gly Ala Pro Leu Cys Leu Ser Gln Gln Leu Arg Met Lys
              20                  25                  30

Gly Asp Tyr Val Leu Gly Gly Leu Phe Pro Leu Gly Glu Ala Glu Glu
          35                  40                  45

Ala Gly Leu Arg Ser Arg Thr Arg Pro Ser Ser Pro Val Cys Thr Arg
      50                  55                  60

Phe Ser Ser Asn Gly Leu Leu Trp Ala Leu Ala Met Lys Met Ala Val
 65                  70                  75                  80

Glu Glu Ile Asn Asn Lys Ser Asp Leu Leu Pro Gly Leu Arg Leu Gly
                  85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Ala Arg Gly Ile Cys Ile Ala His Glu

```
            225                 230                 235                 240
Gly Leu Val Pro Leu Pro Arg Ala Asp Asp Ser Arg Leu Gly Lys Val
                245                 250                 255
Gln Asp Val Leu His Gln Val Asn Gln Ser Ser Val Gln Val Val Leu
                260                 265                 270
Leu Phe Ala Ser Val His Ala Ala His Ala Leu Phe Asn Tyr Ser Ile
                275                 280                 285
Ser Ser Arg Leu Ser Pro Lys Val Trp Val Ala Ser Glu Ala Trp Leu
            290                 295                 300
Thr Ser Asp Leu Val Met Gly Leu Pro Gly Met Ala Gln Met Gly Thr
305                 310                 315                 320
Val Leu Gly Phe Leu Gln Arg Gly Ala Gln Leu His Glu Phe Pro Gln
                325                 330                 335
Tyr Val Lys Thr His Leu Ala Leu Ala Thr Asp Pro Ala Phe Cys Ser
                340                 345                 350
Ala Leu Gly Glu Arg Glu Gln Gly Leu Glu Glu Asp Val Val Gly Gln
                355                 360                 365
Arg Cys Pro Gln Cys Asp Cys Ile Thr Leu Gln Asn Val Ser Ala Gly
            370                 375                 380
Leu Asn His His Gln Thr Phe Ser Val Tyr Ala Ala Val Tyr Ser Val
385                 390                 395                 400
Ala Gln Ala Leu His Asn Thr Leu Gln Cys Asn Ala Ser Gly Cys Pro
                405                 410                 415
Ala Gln Asp Pro Val Lys Pro Trp Gln Leu Leu Glu Asn Met Tyr Asn
                420                 425                 430
Leu Thr Phe His Val Gly Gly Leu Pro Leu Arg Phe Asp Ser Ser Gly
                435                 440                 445
Asn Val Asp Met Glu Tyr Asp Leu Lys Leu Trp Val Trp Gln Gly Ser
            450                 455                 460
Val Pro Arg Leu His Asp Val Gly Arg Phe Asn Gly Ser Leu Arg Thr
465                 470                 475                 480
Glu Arg Leu Lys Ile Arg Trp His Thr Ser Asp Asn Gln Lys Pro Val
                485                 490                 495
Ser Arg Cys Ser Arg Gln Cys Gln Glu Gly Gln Val Arg Arg Val Lys
                500                 505                 510
Gly Phe His Ser Cys Cys Tyr Asp Cys Val Asp Cys Glu Ala Gly Ser
                515                 520                 525
Tyr Arg Gln Asn Pro Asp Asp Ile Ala Cys Thr Phe Cys Gly Gln Asp
            530                 535                 540
Glu Trp Ser Pro Glu Arg Ser Thr Arg Cys Phe Arg Arg Ser Arg
545                 550                 555                 560
Phe Leu Ala Trp Gly Glu Pro Ala Val Leu Leu Leu Leu Leu Leu Leu
                565                 570                 575
Ser Leu Ala Leu Gly Leu Val Leu Ala Ala Leu Gly Leu Phe Val His
                580                 585                 590
His Arg Asp Ser Pro Leu Val Gln Ala Ser Gly Gly Pro Leu Ala Cys
            595                 600                 605
Phe Gly Leu Val Cys Leu Gly Leu Val Cys Leu Ser Val Leu Leu Phe
            610                 615                 620
Pro Gly Gln Pro Ser Pro Ala Arg Cys Leu Ala Gln Pro Leu Ser
625                 630                 635                 640
His Leu Pro Leu Thr Gly Cys Leu Ser Thr Leu Phe Leu Gln Ala Ala
                645                 650                 655
```

```
Glu Ile Phe Val Glu Ser Glu Leu Pro Leu Ser Trp Ala Asp Arg Leu
            660                 665                 670

Ser Gly Cys Leu Arg Gly Pro Trp Ala Trp Leu Val Val Leu Leu Ala
        675                 680                 685

Met Leu Val Glu Val Ala Leu Cys Thr Trp Tyr Leu Val Ala Phe Pro
    690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
                725                 730                 735

Asn Ala Thr Leu Ala Phe Leu Cys Phe Leu Gly Thr Phe Leu Val Arg
            740                 745                 750

Ser Gln Pro Gly Cys Tyr Asn Arg Ala Arg Gly Leu Thr Phe Ala Met
        755                 760                 765

Leu Ala Tyr Phe Ile Thr Trp Val Ser Phe Val Pro Leu Leu Ala Asn
    770                 775                 780

Val Gln Val Val Leu Arg Pro Ala Val Gln Met Gly Ala Leu Leu Leu
785                 790                 795                 800

Cys Val Leu Gly Ile Leu Ala Ala Phe His Leu Pro Arg Cys Tyr Leu
                805                 810                 815

Leu Met Arg Gln Pro Gly Leu Asn Thr Pro Glu Phe Phe Leu Gly Gly
            820                 825                 830

Gly Pro Gly Asp Ala Gln Gly Gln Asn Asp Gly Asn Thr Gly Asn Gln
        835                 840                 845

Gly Lys His Glu
    850

<210> SEQ ID NO 16
<211> LENGTH: 3240
<212> TYPE: DNA
<213> ORGANISM: Mus sp.
<220> FEATURE:
<223> OTHER INFORMATION: mouse Sac non taster 129 T1R3 G-protein
      coupled receptor sweet taste receptor genomic sequence

<400> SEQUENCE: 16
acatctgtgg ctccaacccc acacacccat ctattgttag tgctggagac ttctacctac    60
catgccagct ttggctatca tgggtctcag cctggctgct ttcctggagc ttgggatggg   120
ggcctctttg tgtctgtcac agcaattcaa ggcacaaggg gactacatac tgggcgggct   180
atttcccctg gctcgaccg aggaggccac tctcaaccag agagcacaac ccaacagcac   240
cctgtgtaac aggtatggag gctagtagct ggggtgggag tgaaccgaag cttggcagct   300
ttggctccgt ggtactacca atctggggaa ggggtggtga tcagtttcca tgtggcctca   360
ggttctcacc cctcggtttg ttcctggcca tggctatgaa gatggctgtg gaggagatca   420
acaatggatc tgccttgctc cctgggctgc ggctgggcta tgacctattt gacacatgct   480
ccgagccagt ggtcaccatg aaatccagtc tcatgttcct ggccaaggtg ggcagtcaaa   540
gcattgctgc ctactgcaac tacacacagt accaaccccg tgtgctggct gtcatcggcc   600
cccactcatc agagcttgcc ctcattacag gcaagttctt cagcttcttc ctcatgccac   660
aggtgagccc acttcctttg tgttctcaac cgattgcacc cattgagctc tcacatcaga   720
aagtgcttct tgatcaccac aggtcagcta tagcgccagc atggatcggc taagtgaccg   780
ggaaacgttt ccatccttct tccgcacagt gcccagtgac cgggtgcagc tgcaggcagt   840
tgtgactctg ttgcagaact tcagctggaa ctgggtggcc gccttaggga gtgatgatga   900
```

```
ctatggccgg gaaggtctga gcatcttttc tagtctggcc aatgcacgag gtatctgcat    960
cgcacatgag ggcctggtgc cacaacatga cactagtggc caacagttgg gcaaggtgct   1020
ggatgtgcta cgccaagtga accaaagtaa agtacaagtg gtggtgctgt ttgcctctgc   1080
ccgtgctgtc tactcccttt ttagttacag catccatcat ggcctctcac ccaaggtatg   1140
ggtggccagt gagtcttggc tgacatctga cctggtcatg acacttccca atattgcccg   1200
tgtgggcact gtgcttgggt ttttgcagcg gggtgcccta ctgcctgaat tttcccatta   1260
tgtggagact caccttgccc tggccgctga cccagcattc tgtgcctcac tgaatgcgga   1320
gttggatctg gaggaacatg tgatgggca acgctgtcca cagtgtgacg acatcatgct   1380
gcagaaccta tcatctgggc tgttgcagaa cctatcagct gggcaattgc accaccaaat   1440
atttgcaacc tatgcagctg tgtacagtgt ggctcaagcc cttcacaaca ccctacagtg   1500
caatgtctca cattgccacg tatcagaaca tgttctaccc tggcaggtaa gggtagggtt   1560
ttttgctggg ttttgcctgc tcctgcagga acactgaacc aggcagagcc aaatcatgtt   1620
gtgactggag aggccttacc ctgactccac tccacagctc ctggagaaca tgtacaatat   1680
gagtttccat gctcgagact tgacactaca gtttgatgct gaagggaatg tagacatgga   1740
atatgacctg aagatgtggg tgtggcagag ccctacacct gtattacata ctgtgggcac   1800
cttcaacggc acccttcagc tgcagcagtc taaaatgtac tggccaggca accaggtaag   1860
gacaagacag gcaaaaagga tggtgggtag aagcttgtcg gtcttgggcc agtgctagcc   1920
aaggggaggc ctaacccaag gctccatgtc caggtgccag tctcccagtg ttcccgccag   1980
tgcaaagatg gccaggttcg ccgagtaaag ggctttcatt cctgctgcta tgactgcgtg   2040
gactgcaagg cgggcagcta ccggaagcat ccaggtgaac cgtcttccct agacagtctg   2100
cacagccggg ctaggggca gaagcattca agtctggcaa gcgccctccc gcggggctaa   2160
tgtggagaca gttactgtgg gggctggctg gggaggtcgg tctcccatca gcagacccca   2220
cattactttt cttccttcca tcactacaga tgacttcacc tgtactccat gtaaccagga   2280
ccagtggtcc ccagagaaaa gcacagcctg cttacctcgc aggcccaagt ttctggcttg   2340
gggggagcca gttgtgctgt cactcctcct gctgctttgc ctggtgctgg gtctagcact   2400
ggctgctctg gggctctctg tccaccactg ggacagccct cttgtccagg cctcaggcgg   2460
ctcacagttc tgctttggcc tgatctgcct aggcctcttc tgcctcagtg tccttctgtt   2520
cccaggacgg ccaagctctg ccagctgcct tgcacaacaa ccaatggctc acctccctct   2580
cacaggctgc ctgagcacac tcttcctgca agcagctgag acctttgtgg agtctgagct   2640
gccactgagc tgggcaaact ggctatgcag ctaccttcgg ggactctggg cctggctagt   2700
ggtactgttg ccacttttg tggaggcagc actatgtgcc tggtatttga ccgctttccc   2760
accagaggtg gtgacagact ggtcagtgct gcccacagag gtactggagc actgccacgt   2820
gcgttcctgg gtcagcctgg gcttggtgca catcaccaat gcaatgttag cttttcctct   2880
ctttctgggc actttcctgg tacagagcca gcctggccgc tacaaccgtg cccgtggtct   2940
caccttcgcc atgctagctt atttcatcac ctgggtctct tttgtgcccc tcctggccaa   3000
tgtgcaggtg gcctaccagc cagctgtgca gatgggtgct atcctagtct gtgccctggg   3060
catcctggtc accttccacc tgcccaagtg ctatgtgctt ctttggctgc aaagctcaa   3120
cacccaggag ttcttcctgg gaaggaatgc caagaaagca gcagatgaga acagtggcgg   3180
tggtgaggca gctcaggaac acaatgaatg accactgacc cgtgaccttc cctttaggga   3240
```

<210> SEQ ID NO 17

<211> LENGTH: 2577
<212> TYPE: DNA
<213> ORGANISM: Mus sp.
<220> FEATURE:
<223> OTHER INFORMATION: mouse Sac non taster 129 T1R3 G-protein
      coupled receptor sweet taste receptor CDS

<400> SEQUENCE: 17

| | |
|---|---:|
| atgccagctt tggctatcat gggtctcagc ctggctgctt tcctggagct tgggatgggg | 60 |
| gcctctttgt gtctgtcaca gcaattcaag gcacaagggg actacatact gggcgggcta | 120 |
| tttcccctgg gctcgaccga ggaggccact ctcaaccaga gagcacaacc caacagcacc | 180 |
| ctgtgtaaca ggttctcacc cctcggtttg ttcctggcca tggctatgaa gatggctgtg | 240 |
| gaggagatca acaatggatc tgccttgctc cctgggctgc ggctgggcta tgacctattt | 300 |
| gacacatgct ccgagccagt ggtcaccatg aaatccagtc tcatgttcct ggccaaggtg | 360 |
| ggcagtcaaa gcattgctgc ctactgcaac tacacacagt accaaccccg tgtgctggct | 420 |
| gtcatcggcc cccactcatc agagcttgcc ctcattacag gcaagttctt cagcttcttc | 480 |
| ctcatgccac aggtcagcta tagcgccagc atggatcggc taagtgaccg ggaaacgttt | 540 |
| ccatccttct ccgcacagt gcccagtgac cgggtgcagc tgcaggcagt tgtgactctg | 600 |
| ttgcagaact tcagctggaa ctgggtggcc gccttaggga gtgatgatga ctatggccgg | 660 |
| gaaggtctga gcatcttttc tagtctgcc aatgcacgag gtatctgcat cgcacatgag | 720 |
| ggcctggtgc acaacatga cactagtggc caacagttgg gcaaggtgct ggatgtgcta | 780 |
| cgccaagtga accaaagtaa agtacaagtg gtggtgctgt ttgcctctgc ccgtgctgtc | 840 |
| tactcccttt ttagttacag catccatcat ggcctctcac ccaaggtatg ggtggccagt | 900 |
| gagtcttggc tgacatctga cctggtcatg acacttccca atattgcccg tgtgggcact | 960 |
| gtgcttgggt ttttgcagcg gggtgccta ctgcctgaat tttcccatta tgtggagact | 1020 |
| caccttgccc tggccgctga cccagcattc tgtgcctcac tgaatgcgga gttggatctg | 1080 |
| gaggaacatg tgatggggca acgctgtcca cagtgtgacg acatcatgct gcagaaccta | 1140 |
| tcatctgggc tgttgcagaa cctatcagct gggcaattgc accaccaaat atttgcaacc | 1200 |
| tatgcagctg tgtacagtgt ggctcaagcc cttcacaaca cctacagtg caatgtctca | 1260 |
| cattgccacg tatcagaaca tgttctaccc tggcagctcc tggagaacat gtacaatatg | 1320 |
| agtttccatg ctcgagactt gacactacag tttgatgctg aagggaatgt agacatggaa | 1380 |
| tatgacctga agatgtgggt gtggcagagc cctacacctg tattacatac tgtgggcacc | 1440 |
| ttcaacggca cccttcagct gcagcagtct aaaatgtact ggccaggcaa ccaggtgcca | 1500 |
| gtctcccagt gttcccgcca gtgcaaagat ggccagttc gccgagtaaa gggctttcat | 1560 |
| tcctgctgct atgactgcgt ggactgcaag gcgggcagct accggaagca tccagatgac | 1620 |
| ttcacctgta ctccatgtaa ccaggaccag tggtccccag agaaaagcac agcctgctta | 1680 |
| cctcgcaggc ccaagtttct ggcttggggg gagccagttg tgctgtcact cctcctgctg | 1740 |
| ctttgcctgg tgctgggtct agcactggct gctctgggc tctctgtcca ccactgggac | 1800 |
| agccctcttg tccaggcctc aggcggctca cagttctgct ttggcctgat ctgcctaggc | 1860 |
| ctcttctgcc tcagtgtcct tctgttccca ggacggccaa gctctgccag ctgccttgca | 1920 |
| caacaaccaa tggctcacct ccctctcaca ggctgcctga gcacactctt cctgcaagca | 1980 |
| gctgagacct tgtggagtc tgagctgcca ctgagctggg caaactggct atgcagctac | 2040 |
| cttcggggac tctgggcctg gctagtggta ctgttggcca cttttgtgga ggcagcacta | 2100 |
| tgtgcctggt atttgaccgc tttcccacca gaggtggtga cagactggtc agtgctgccc | 2160 |

-continued

```
acagaggtac tggagcactg ccacgtgcgt tcctgggtca gcctgggctt ggtgcacatc    2220
accaatgcaa tgttagcttt cctctgcttt ctgggcactt tcctggtaca gagccagcct    2280
ggccgctaca accgtgcccg tggtctcacc ttcgccatgc tagcttattt catcacctgg    2340
gtctcttttg tgcccctcct ggccaatgtg caggtggcct accagccagc tgtgcagatg    2400
ggtgctatcc tagtctgtgc cctgggcatc ctggtcacct tccacctgcc caagtgctat    2460
gtgcttcttt ggctgccaaa gctcaacacc caggagttct tcctgggaag gaatgccaag    2520
aaagcagcag atgagaacag tggcggtggt gaggcagctc aggaacacaa tgaatga      2577
```

<210> SEQ ID NO 18
<211> LENGTH: 858
<212> TYPE: PRT
<213> ORGANISM: Mus sp.
<220> FEATURE:
<223> OTHER INFORMATION: mouse Sac non taster 129 T1R3 G-protein
      coupled receptor sweet taste receptor

<400> SEQUENCE: 18

```
Met Pro Ala Leu Ala Ile Met Gly Leu Ser Leu Ala Ala Phe Leu Glu
 1               5                  10                  15

Leu Gly Met Gly Ala Ser Leu Cys Leu Ser Gln Gln Phe Lys Ala Gln
            20                  25                  30

Gly Asp Tyr Ile Leu Gly Gly Leu Phe Pro Leu Gly Ser Thr Glu Glu
        35                  40                  45

Ala Thr Leu Asn Gln Arg Ala Gln Pro Asn Ser Thr Leu Cys Asn Arg
    50                  55                  60

Phe Ser Pro Leu Gly Leu Phe Leu Ala Met Ala Met Lys Met Ala Val
65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Ser
            100                 105                 110

Ser Leu Met Phe Leu Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Tyr Gly Arg Glu Gly Leu Ser
    210                 215                 220

Ile Phe Ser Ser Leu Ala Asn Ala Arg Gly Ile Cys Ile Ala His Glu
225                 230                 235                 240

Gly Leu Val Pro Gln His Asp Thr Ser Gly Gln Gln Leu Gly Lys Val
                245                 250                 255

Leu Asp Val Leu Arg Gln Val Asn Gln Ser Lys Val Gln Val Val Val
            260                 265                 270

Leu Phe Ala Ser Ala Arg Ala Val Tyr Ser Leu Phe Ser Tyr Ser Ile
        275                 280                 285
```

-continued

His His Gly Leu Ser Pro Lys Val Trp Val Ala Ser Glu Ser Trp Leu
            290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr His Leu Ala Leu Ala Ala Asp Pro Ala Phe Cys Ala
            340                 345                 350

Ser Leu Asn Ala Glu Leu Asp Leu Glu Glu His Val Met Gly Gln Arg
        355                 360                 365

Cys Pro Gln Cys Asp Asp Ile Met Leu Gln Asn Leu Ser Ser Gly Leu
    370                 375                 380

Leu Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Val Ser Glu His Val Leu Pro Trp Gln
            420                 425                 430

Leu Leu Glu Asn Met Tyr Asn Met Ser Phe His Ala Arg Asp Leu Thr
        435                 440                 445

Leu Gln Phe Asp Ala Glu Gly Asn Val Asp Met Glu Tyr Asp Leu Lys
    450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
                485                 490                 495

Asn Gln Val Pro Val Ser Gln Cys Ser Arg Gln Cys Lys Asp Gly Gln
            500                 505                 510

Val Arg Arg Val Lys Gly Phe His Ser Cys Cys Tyr Asp Cys Val Asp
        515                 520                 525

Cys Lys Ala Gly Ser Tyr Arg Lys His Pro Asp Asp Phe Thr Cys Thr
    530                 535                 540

Pro Cys Asn Gln Asp Gln Trp Ser Pro Glu Lys Ser Thr Ala Cys Leu
545                 550                 555                 560

Pro Arg Arg Pro Lys Phe Leu Ala Trp Gly Glu Pro Val Val Leu Ser
                565                 570                 575

Leu Leu Leu Leu Leu Cys Leu Val Leu Gly Leu Ala Leu Ala Ala Leu
            580                 585                 590

Gly Leu Ser Val His His Trp Asp Ser Pro Leu Val Gln Ala Ser Gly
        595                 600                 605

Gly Ser Gln Phe Cys Phe Gly Leu Ile Cys Leu Gly Leu Phe Cys Leu
    610                 615                 620

Ser Val Leu Leu Phe Pro Gly Arg Pro Ser Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Thr Phe Val Glu Ser Glu Leu Pro Leu Ser
            660                 665                 670

Trp Ala Asn Trp Leu Cys Ser Tyr Leu Arg Gly Leu Trp Ala Trp Leu
        675                 680                 685

Val Val Leu Leu Ala Thr Phe Val Glu Ala Ala Leu Cys Ala Trp Tyr
    690                 695                 700

Leu Thr Ala Phe Pro Pro Glu Val Val Thr Asp Trp Ser Val Leu Pro
705                 710                 715                 720

```
Thr Glu Val Leu Glu His Cys His Val Arg Ser Trp Val Ser Leu Gly
            725                 730                 735
Leu Val His Ile Thr Asn Ala Met Leu Ala Phe Leu Cys Phe Leu Gly
        740                 745                 750
Thr Phe Leu Val Gln Ser Gln Pro Gly Arg Tyr Asn Arg Ala Arg Gly
    755                 760                 765
Leu Thr Phe Ala Met Leu Ala Tyr Phe Ile Thr Trp Val Ser Phe Val
770                 775                 780
Pro Leu Leu Ala Asn Val Gln Val Ala Tyr Gln Pro Ala Val Gln Met
785                 790                 795                 800
Gly Ala Ile Leu Val Cys Ala Leu Gly Ile Leu Val Thr Phe His Leu
                805                 810                 815
Pro Lys Cys Tyr Val Leu Leu Trp Leu Pro Lys Leu Asn Thr Gln Glu
            820                 825                 830
Phe Phe Leu Gly Arg Asn Ala Lys Lys Ala Ala Asp Glu Asn Ser Gly
        835                 840                 845
Gly Gly Glu Ala Ala Gln Glu His Asn Glu
    850                 855
```

<210> SEQ ID NO 19
<211> LENGTH: 2577
<212> TYPE: DNA
<213> ORGANISM: Mus sp.
<220> FEATURE:
<223> OTHER INFORMATION: mouse Sac taster SWR T1R3 G-protein coupled
      receptor sweet taste receptor CDS

<400> SEQUENCE: 19

```
atgccagctt tggctatcat gggtctcagc ctggctgctt tcctggagct tgggatgggg      60
gcctctttgt gtctgtcaca gcaattcaag gcacaagggg actacatact gggcgggcta     120
tttcccctgg gctcaaccga ggaggccact ctcaaccaga aacacaaacc caacagcatc     180
ctgtgtaaca ggttctcacc cctcggtttg ttcctggcca tggctatgaa gatggctgtg     240
gaggagatca caatggatc tgccttgctc cctgggctgc ggctgggcta tgacctattt     300
gacacatgct ccgagccagt ggtcaccatg aaatccagtc tcatgttcct ggccaaggtg     360
ggcagtcaaa gcattgctgc ctactgcaac tacacacagt accaaccccg tgtgctggct     420
gtcatcggcc cccactcatc agagcttgcc ctcattacag gcaagttctt cagcttcttc     480
ctcatgccac aggtcagcta tagcgccagc atggatcggc taagtgaccg gaaacgtttt     540
ccatccttct tccgcacagt gcccagtgac cgggtgcagc tgcaggcagt tgtgactctg     600
ttgcagaact tcagctggaa ctgggtggcc gccttaggga gtgatgatga ctatggccgg     660
gaaggtctga gcatcttttc tagtctggcc aatgcacgag gtatctgcat cgcacatgag     720
ggcctggtgc acaacatga cactagtggc aacagttgg gcaaggtgct ggatgtgcta     780
tgccaagtga ccaaagtaa agtacaagtg gtggtgctgt tgcctctgc ccgtgctgtc     840
tactcccttt ttagttacag catccatcat ggcctctcac ccaaggtatg ggtggccagt     900
gagtcttggc tgacatctga cctggtcatg acacttccca atattgcccg tgtgggcact     960
gtgcttgggt ttttgcagcg gggtgcccta ctgcctgaat tccccattat tgtggagact    1020
caccttgccc tggccgctga cccagcattc tgtgcctcac tgaatgcgga gttggatctg    1080
gaggaacatg tgatggggca acgctgtcca cagtgtgacg acatcatgct gcagaaccta    1140
tcatctgggc tgttgcagaa cctatcagct ggcaattgc accaccaaat atttgcaacc    1200
tatgcagctg tgtacagtgt ggctcaagcc cttcacaaca cctacagtg caatgtctca    1260
```

```
cattgccatg tatcagaaca tgttctaccc tggcagctcc tggagaacat gtacaatatg    1320
agtttccatg ctcgagactt gacactacag tttgatgctg aagggaatgt agacatggaa    1380
tatgacctga agatgtgggt gtggcagagc cctacacctg tattacatac tgtgggcacc    1440
ttcaacggca cccttcagct gcagcagtct aaaatgtact ggccaggcaa ccaggtgcca    1500
gtctcccagt gttcccgcca gtgcaaagat ggccaggttc gccgagtaaa gggcttcat    1560 tcctgctgct atgactgcgt ggactgcaag gcgggcagct accggaagca tccagatgac    1620
ttcacctgta ctccatgtaa ccaggaccag tggtccccag agaaaagcac agcctgctta    1680
cctcgcaggc ccaagtttct ggcttggggg gagccagttg tgctgtcact cctcctgctg    1740 cttttgcctgg tgctgggtct agcactggct gctctgggc tctctgtcca ccactgggac    1800
agccctcttg tccaggcctc aggcggctca cagttctgct ttggcctgat ctgcctaggc    1860
ctcttctgcc tcagtgtcct tctgttccca ggacggccaa gctctgccag ctgccttgca    1920
caacaaccaa tggctcacct ccctctcaca ggctgcctga gcacactctt cctgcaagca    1980
gctgagacct tgtggagtc tgagctgcca ctgagctggg caaactggct atgcagctac    2040
cttcggggac tctgggcctg gctagtggta ctgtcggcca ctttgtgga ggcagcacta    2100 tgtgcctggt atttgaccgc tttcccacca gaggtggtga cagactggtc agtgctgccc    2160
acagaggtac tggagcactg ccacgtgcgt tcctgggtca gcctgggctt ggtgcacatc    2220
accaatgcaa tgttagcttt cctctgcttt ctgggcactt tcctggtaca gagccagcct    2280
ggccgctaca accgtgcccg tggtctcacc ttcgccatgc tagcttattt catcacctgg    2340
gtctcttttg tgcccctcct ggccaatgtg caggtggcct accagccagc tgtgcagatg    2400
ggtgctatcc tagtctgtgc cctgggcatc ctggtcacct tccacctgcc caagtgctat    2460
gtgcttcttt ggctgccaaa gctcaacacc caggagttct tcctgggaag gaatgccaag    2520
aaagcagcag atgagaacag tggcggtggt gaggcagctc aggaacacaa tgaatga      2577
```

<210> SEQ ID NO 20
<211> LENGTH: 858
<212> TYPE: PRT
<213> ORGANISM: Mus sp.
<220> FEATURE:
<223> OTHER INFORMATION: mouse Sac taster SWR T1R3 G-protein coupled
      receptor sweet taste receptor

<400> SEQUENCE: 20

```
Met Pro Ala Leu Ala Ile Met Gly Leu Ser Leu Ala Ala Phe Leu Glu
  1               5                  10                  15

Leu Gly Met Gly Ala Ser Leu Cys Leu Ser Gln Gln Phe Lys Ala Gln
             20                  25                  30

Gly Asp Tyr Ile Leu Gly Gly Leu Phe Pro Leu Gly Ser Thr Glu Glu
         35                  40                  45

Ala Thr Leu Asn Gln Arg Thr Gln Pro Asn Ser Ile Leu Cys Asn Arg
     50                  55                  60

Phe Ser Pro Leu Gly Leu Phe Leu Ala Met Ala Met Lys Met Ala Val
 65                  70                  75                  80

Glu Glu Ile Asn Asn Gly Ser Ala Leu Leu Pro Gly Leu Arg Leu Gly
                 85                  90                  95

Tyr Asp Leu Phe Asp Thr Cys Ser Glu Pro Val Val Thr Met Lys Ser
            100                 105                 110

Ser Leu Met Phe Leu Ala Lys Val Gly Ser Gln Ser Ile Ala Ala Tyr
        115                 120                 125
```

-continued

```
Cys Asn Tyr Thr Gln Tyr Gln Pro Arg Val Leu Ala Val Ile Gly Pro
    130                 135                 140
His Ser Ser Glu Leu Ala Leu Ile Thr Gly Lys Phe Phe Ser Phe Phe
145                 150                 155                 160
Leu Met Pro Gln Val Ser Tyr Ser Ala Ser Met Asp Arg Leu Ser Asp
                165                 170                 175
Arg Glu Thr Phe Pro Ser Phe Phe Arg Thr Val Pro Ser Asp Arg Val
                180                 185                 190
Gln Leu Gln Ala Val Val Thr Leu Leu Gln Asn Phe Ser Trp Asn Trp
                195                 200                 205
Val Ala Ala Leu Gly Ser Asp Asp Tyr Gly Arg Glu Gly Leu Ser
    210                 215                 220
Ile Phe Ser Ser Leu Ala Asn Ala Arg Gly Ile Cys Ile Ala His Glu
225                 230                 235                 240
Gly Leu Val Pro Gln His Asp Thr Ser Gly Gln Gln Leu Gly Lys Val
                245                 250                 255
Leu Asp Val Leu Cys Gln Val Asn Gln Ser Lys Val Gln Val Val
                260                 265                 270
Leu Phe Ala Ser Ala Arg Ala Val Tyr Ser Leu Phe Ser Tyr Ser Ile
    275                 280                 285
His His Gly Leu Ser Pro Lys Val Trp Val Ala Ser Glu Ser Trp Leu
    290                 295                 300
Thr Ser Asp Leu Val Met Thr Leu Pro Asn Ile Ala Arg Val Gly Thr
305                 310                 315                 320
Val Leu Gly Phe Leu Gln Arg Gly Ala Leu Leu Pro Glu Phe Ser His
                325                 330                 335
Tyr Val Glu Thr His Leu Ala Leu Ala Ala Asp Pro Ala Phe Cys Ala
                340                 345                 350
Ser Leu Asn Ala Glu Leu Asp Leu Glu Glu His Val Met Gly Gln Arg
                355                 360                 365
Cys Pro Gln Cys Asp Asp Ile Met Leu Gln Asn Leu Ser Ser Gly Leu
    370                 375                 380
Leu Gln Asn Leu Ser Ala Gly Gln Leu His His Gln Ile Phe Ala Thr
385                 390                 395                 400
Tyr Ala Ala Val Tyr Ser Val Ala Gln Ala Leu His Asn Thr Leu Gln
                405                 410                 415
Cys Asn Val Ser His Cys His Val Ser Glu His Val Leu Pro Trp Gln
                420                 425                 430
Leu Leu Glu Asn Met Tyr Asn Met Ser Phe His Ala Arg Asp Leu Thr
    435                 440                 445
Leu Gln Phe Asp Ala Glu Gly Asn Val Asp Met Glu Tyr Asp Leu Lys
    450                 455                 460
Met Trp Val Trp Gln Ser Pro Thr Pro Val Leu His Thr Val Gly Thr
465                 470                 475                 480
Phe Asn Gly Thr Leu Gln Leu Gln Gln Ser Lys Met Tyr Trp Pro Gly
                485                 490                 495
Asn Gln Val Pro Val Ser Gln Cys Ser Arg Gln Cys Lys Asp Gly Gln
                500                 505                 510
Val Arg Arg Val Lys Gly Phe His Ser Cys Cys Tyr Asp Cys Val Asp
                515                 520                 525
Cys Lys Ala Gly Ser Tyr Arg Lys His Pro Asp Asp Phe Thr Cys Thr
    530                 535                 540
Pro Cys Asn Gln Asp Gln Trp Ser Pro Glu Lys Ser Thr Ala Cys Leu
545                 550                 555                 560
```

```
Pro Arg Arg Pro Lys Phe Leu Ala Trp Gly Glu Pro Val Val Leu Ser
                565                 570                 575
Leu Leu Leu Leu Leu Cys Leu Val Leu Gly Leu Ala Leu Ala Ala Leu
            580                 585                 590
Gly Leu Ser Val His His Trp Asp Ser Pro Leu Val Gln Ala Ser Gly
        595                 600                 605
Gly Ser Gln Phe Cys Phe Gly Leu Ile Cys Leu Gly Leu Phe Cys Leu
    610                 615                 620
Ser Val Leu Leu Phe Pro Gly Arg Pro Ser Ser Ala Ser Cys Leu Ala
625                 630                 635                 640
Gln Gln Pro Met Ala His Leu Pro Leu Thr Gly Cys Leu Ser Thr Leu
                645                 650                 655
Phe Leu Gln Ala Ala Glu Thr Phe Val Glu Ser Glu Leu Pro Leu Ser
            660                 665                 670
Trp Ala Asn Trp Leu Cys Ser Tyr Leu Arg Gly Leu Trp Ala Trp Leu
        675                 680                 685
Val Val Leu Ser Ala Thr Phe Val Glu Ala Ala Leu Cys Ala Trp Tyr
    690                 695                 700
Leu Thr Ala Phe Pro Pro Glu Val Val Thr Asp Trp Ser Val Leu Pro
705                 710                 715                 720
Thr Glu Val Leu Glu His Cys His Val Arg Ser Trp Val Ser Leu Gly
                725                 730                 735
Leu Val His Ile Thr Asn Ala Met Leu Ala Phe Leu Cys Phe Leu Gly
            740                 745                 750
Thr Phe Leu Val Gln Ser Gln Pro Gly Arg Tyr Asn Arg Ala Arg Gly
        755                 760                 765
Leu Thr Phe Ala Met Leu Ala Tyr Phe Ile Thr Trp Val Ser Phe Val
    770                 775                 780
Pro Leu Leu Ala Asn Val Gln Val Ala Tyr Gln Pro Ala Val Gln Met
785                 790                 795                 800
Gly Ala Ile Leu Val Cys Ala Leu Gly Ile Leu Val Thr Phe His Leu
                805                 810                 815
Pro Lys Cys Tyr Val Leu Leu Trp Leu Pro Lys Leu Asn Thr Gln Glu
            820                 825                 830
Phe Phe Leu Gly Arg Asn Ala Lys Lys Ala Ala Asp Glu Asn Ser Gly
        835                 840                 845
Gly Gly Glu Ala Ala Gln Glu His Asn Glu
    850                 855

<210> SEQ ID NO 21
<211> LENGTH: 3200
<212> TYPE: DNA
<213> ORGANISM: Mus sp.
<220> FEATURE:
<223> OTHER INFORMATION: mouse Sac taster C57 T1R3 G-protein coupled
      receptor sweet taste receptor genomic sequence

<400> SEQUENCE: 21
cccacacacc cacccattgt tagtgctgga gacttctacc taccatgcca gctttggcta      60
tcatgggtct cagcctggct gctttcctgg agcttgggat gggggcctct ttgtgtctgt     120
cacagcaatt caaggcacaa ggggactaca tactgggcgg gctatttccc ctgggctcaa     180
ccgaggaggc cactctcaac cagagaacac aacccaacag catcccgtgc aacaggtatg     240
gaggctagta gctggggtgg gagtgaaccg aagcttggca gctttggctc cgtggtacta     300
ccaatctggg aagaggtggt gatcagtttc catgtggcct caggttctca ccccttggtt     360
```

```
tgttcctggc catggctatg aagatggctg tggaggagat caacaatgga tctgccttgc    420
tccctgggct gcggctgggc tatgacctat ttgacacatg ctccgagcca gtggtcacca    480
tgaaatccag tctcatgttc ctggccaagg tgggcagtca aagcattgct gcctactgca    540
actacacaca gtaccaaccc cgtgtgctgg ctgtcatcgg cccccactca tcagagcttg    600
ccctcattac aggcaagttc ttcagcttct tcctcatgcc acaggtgagc ccacttcctt    660
tgtgttctca accgattgca cccattgagc tctcatatca gaaagtgctt cttgatcacc    720
acaggtcagc tatagtgcca gcatggatcg gctaagtgac cggaaacgt ttccatcctt     780
cttccgcaca gtgcccagtg accgggtgca gctgcaggca gttgtgactc tgttgcagaa    840
cttcagctgg aactgggtgg ccgccttagg gagtgatgat gactatggcc gggaaggtct    900
gagcatcttt tctagtctgg ccaatgcacg aggtatctgc atcgcacatg agggcctggt    960
gccacaacat gacactagtg gccaacagtt gggcaaggtg ctggatgtac tacgccaagt   1020
gaaccaaagt aaagtacaag tggtggtgct gtttgcctct gcccgtgctg tctactccct   1080
ttttagttac agcatccatc atggcctctc acccaaggta tgggtggcca gtgagtcttg   1140
gctgacatct gacctggtca tgacacttcc caatattgcc cgtgtgggca ctgtgcttgg   1200
gtttttgcag cggggtgccc tactgcctga attttcccat tatgtggaga ctcaccttgc   1260
cctggccgct gacccagcat tctgtgcctc actgaatgcg gagttggatc tggaggaaca   1320
tgtgatgggg caacgctgtc cacggtgtga cgacatcatg ctgcagaacc tatcatctgg   1380
gctgttgcag aacctatcag ctgggcaatt gcaccaccaa atatttgcaa cctatgcagc   1440
tgtgtacagt gtggctcaag cccttcacaa caccctacag tgcaatgtct cacattgcca   1500
cgtatcagaa catgttctac cctggcaggt aagggtaggg tttttgctg ggttttgcct     1560
gctcctgcag gaacactgaa ccaggcagag ccaaatcttg ttgtgactgg agaggcctta   1620
ccctgactcc actccacagc tcctggagaa catgtacaat atgagtttcc atgctcgaga   1680
cttgacacta cagtttgatg ctgaagggaa tgtagacatg gaatatgacc tgaagatgtg   1740
ggtgtggcag agccctacac ctgtattaca tactgtgggc accttcaacg caccccttca   1800
gctgcagcag tctaaaatgt actggccagg caaccaggta aggacaagac aggcaaaaag   1860
gatggtgggt agaagcttgt cggtcttggg ccagtgctag ccaaggggag gcctaaccca   1920
aggctccatg tacaggtgcc agtctcccag tgttcccgcc agtgcaaaga tggccaggtt   1980
cgccgagtaa agggctttca ttcctgctgc tatgactgcg tggactgcaa ggcgggcagc   2040
taccggaagc atccaggtga accgtcttcc ctagacagtc tgcacagccg ggctaggggg   2100
cagaagcatt caagtctggc aagcgccctc ccgcggggct aatgtggaga cagttactgt   2160
gggggctggc tgggaggtc ggtctcccat cagcagaccc cacattactt tcttccttc     2220
catcactaca gatgacttca cctgtactcc atgtaaccag gaccagtggt ccccagagaa   2280
aagcacagcc tgcttacctc gcaggcccaa gtttctggct tggggggagc cagttgtgct   2340
gtcactcctc ctgctgcttt gcctggtgct gggtctagca ctggctgctc tggggctctc   2400
tgtccaccac tgggacagcc ctcttgtcca ggcctcaggt ggctcacagt tctgctttgg   2460
cctgatctgc ctaggcctct tctgcctcag tgtccttctg ttcccagggc ggccaagctc   2520
tgccagctgc cttgcacaac aaccaatggc tcacctccct ctcacaggct gcctgagcac   2580
actcttcctg caagcagctg agacctttgt ggagtctgag ctgccactga gctgggcaaa   2640
ctggctatgc agctaccttc ggggactctg ggcctggcta gtggtactgt tggccacttt   2700
tgtggaggca gcactatgtg cctggtattt gatcgctttc ccaccagagg tggtgacaga   2760
```

```
ctggtcagtg ctgcccacag aggtactgga gcactgccac gtgcgttcct gggtcagcct    2820
gggcttggtg cacatcacca atgcaatgtt agctttcctc tgctttctgg gcactttcct    2880
ggtacagagc cagcctggcc gctacaaccg tgcccgtggt ctcaccttcg ccatgctagc    2940
ttatttcatc acctgggtct cttttgtgcc cctcctggcc aatgtgcagg tggcctacca    3000
gccagctgtg cagatgggtg ctatcctagt ctgtgccctg gcatcctggt caccttcca    3060 cctgcccaag tgctatgtgc ttctttggct gccaaagctc aacacccagg agttcttcct    3120
gggaaggaat gccaagaaag cagcagatga aacagtggc ggtggtgagg cagctcaggg    3180
acacaatgaa tgaccactga                                                3200

<210> SEQ ID NO 22
<211> LENGTH: 2577
<212> TYPE: DNA
<213> ORGANISM: Mus sp.
<220> FEATURE:
<223> OTHER INFORMATION: mouse Sac taster C57 T1R3 G-protein coupled
      receptor sweet taste receptor CDS

<400> SEQUENCE: 22
atgccagctt tggctatcat gggtctcagc ctggctgctt tcctggagct tgggatgggg     60
gcctctttgt gtctgtcaca gcaattcaag gcacaagggg actacatact gggcgggcta    120
tttcccctgg gctcaaccga ggaggccact ctcaaccaga gaacacaacc caacagcatc    180
ccgtgcaaca ggttctcacc ccttggtttg ttcctggcca tggctatgaa gatggctgtg    240
gaggagatca acaatggatc tgccttgctc cctgggctgc ggctgggcta tgacctattt    300
gacacatgct ccgagccagt ggtcaccatg aaatccagtc tcatgttcct ggccaaggtg    360
ggcagtcaaa gcattgctgc ctactgcaac tacacacagt accaaccccg tgtgctggct    420
gtcatcggcc cccactcatc agagcttgcc ctcattacag caagttcttc cagcttcttc    480
ctcatgccac aggtcagcta tagtgccagc atggatcggc taagtgaccg ggaaacgttt    540
ccatccttct ccgcacagt gcccagtgac cgggtgcagc tgcaggcagt tgtgactctg    600
ttgcagaact tcagctggaa ctgggtggcc gccttaggga gtgatgatga ctatggccgg    660
gaaggtctga gcatcttttc tagtctggcc aatgcacgag gtatctgcat cgcacatgag    720
ggcctggtgc acaacatga cactagtggc caacagttgg gcaaggtgct ggatgtacta    780
cgccaagtga accaaagtaa agtacaagtg gtggtgctgt tgcctctgc ccgtgctgtc    840 tactcccttt ttagttacag catccatcat ggctctcac ccaaggtatg ggtggccagt    900
gagtcttggc tgacatctga cctggtcatg acacttccca atattgcccg tgtgggcact    960
gtgcttgggt ttttgcagcg gggtgcccta ctgcctgaat tttcccatta tgtggagact    1020
caccttgccc tggccgctga cccagcattc tgtgcctcac tgaatgcgga gttggatctg    1080
gaggaacatg tgatgggca acgctgtcca cggtgtgacg acatcatgct gcagaaccta    1140
tcatctgggc tgttgcagaa cctatcagct gggcaattgc accaccaaat atttgcaacc    1200
tatgcagctg tgtacagtgt ggctcaagcc cttcacaaca ccctacagtg caatgtctca    1260
cattgccacg tatcagaaca tgttctaccc tggcagctcc tggagaacat gtacaatatg    1320
agtttccatg ctcgagactt gacactacag tttgatgctg aagggaatgt agacatggaa    1380
tatgacctga agatgtgggt gtggcagagc cctacacctg tattacatac tgtgggcacc    1440
ttcaacggca ccctttcagct gcagcagtct aaaatgtact ggccaggcaa ccaggtgcca    1500
gtctcccagt gttccgcca gtgcaaagat ggccagggttc gccgagtaaa gggcttcat    1560
```

-continued

```
tcctgctgct atgactgcgt ggactgcaag gcgggcagct accggaagca tccagatgac    1620
ttcacctgta ctccatgtaa ccaggaccag tggtccccag agaaaagcac agcctgctta    1680
cctcgcaggc ccaagtttct ggcttggggg gagccagttg tgctgtcact cctcctgctg    1740
cttttgcctgg tgctgggtct agcactggct gctctggggc tctctgtcca ccactgggac    1800
agccctcttg tccaggcctc aggtggctca cagttctgct ttggcctgat ctgcctaggc    1860
ctcttctgcc tcagtgtcct tctgttccca gggcggccaa gctctgccag ctgccttgca    1920
caacaaccaa tggctcacct ccctctcaca ggctgcctga gcacactctt cctgcaagca    1980
gctgagacct ttgtggagtc tgagctgcca ctgagctggg caaactggct atgcagctac    2040
cttcggggac tctgggcctg gctagtggta ctgttggcca cttttgtgga ggcagcacta    2100
tgtgcctggt atttgatcgc tttcccacca gaggtggtga cagactggtc agtgctgccc    2160
acagaggtac tggagcactg ccacgtgcgt tcctgggtca gcctgggctt ggtgcacatc    2220
accaatgcaa tgttagcttt cctctgcttt ctgggcactt tcctggtaca gagccagcct    2280
ggccgctaca accgtgcccg tggtctcacc ttcgccatgc tagcttattt catcacctgg    2340
gtctcttttg tgcccctcct ggccaatgtg caggtggcct accagccagc tgtgcagatg    2400
ggtgctatcc tagtctgtgc cctgggcatc ctggtcacct tccacctgcc caagtgctat    2460
gtgcttcttt ggctgccaaa gctcaacacc caggagttct tcctgggaag gaatgccaag    2520
aaagcagcag atgagaacag tggcggtggt gaggcagctc agggacacaa tgaatga       2577
```

<210> SEQ ID NO 23  
<211> LENGTH: 858  
<212> TYPE: PRT  
<213> ORGANISM: Mus sp.  
<220> FEATURE:  
<223> OTHER INFORMATION: mouse Sac taster C57 T1R3 G-protein coupled receptor sweet taste receptor

<400> SEQUENCE: 23

```
Met Pro Ala Leu Ala Ile Met Gly Leu Ser Leu Ala Ala Phe Leu Glu
  1               5                  10                  15

Leu Gly Met Gly Ala Ser Leu Cys Leu Ser Gln Gln Phe Lys Ala Gln
             20                  25                  30

Gly Asp Tyr Ile Leu Gly Gly Leu Phe Pro Leu Gly Ser Thr Glu Glu
         35                  40                  45

Ala Thr Leu Asn Gln Arg Thr Gln Pro Asn Ser Ile Pro Cys Asn Arg
     50                  55                  60

Phe Ser Pro Leu Gly Leu Phe Leu Ala Met Ala Met Lys Met Ala Val
 65                  70                  75                  80

Glu Glu Ile Asn Asn Gly Ser Ala Leu Leu Pro Gly Leu Arg Leu Gly
                 85                  90                  95

Tyr Asp Leu Phe Asp Thr Cys Ser Glu Pro Val Val Thr Met Lys Ser
            100                 105                 110

Ser Leu Met Phe Leu Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190
```

-continued

```
Gln Leu Gln Ala Val Val Thr Leu Leu Gln Asn Phe Ser Trp Asn Trp
            195                 200                 205

Val Ala Ala Leu Gly Ser Asp Asp Tyr Gly Arg Glu Gly Leu Ser
        210                 215                 220

Ile Phe Ser Ser Leu Ala Asn Ala Arg Gly Ile Cys Ile Ala His Glu
225                 230                 235                 240

Gly Leu Val Pro Gln His Asp Thr Ser Gly Gln Gln Leu Gly Lys Val
                245                 250                 255

Leu Asp Val Leu Arg Gln Val Asn Gln Ser Lys Val Gln Val Val
            260                 265                 270

Leu Phe Ala Ser Ala Arg Ala Val Tyr Ser Leu Phe Ser Tyr Ser Ile
        275                 280                 285

His His Gly Leu Ser Pro Lys Val Trp Val Ala Ser Glu Ser Trp Leu
        290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr His Leu Ala Leu Ala Ala Asp Pro Ala Phe Cys Ala
            340                 345                 350

Ser Leu Asn Ala Glu Leu Asp Leu Glu Glu His Val Met Gly Gln Arg
        355                 360                 365

Cys Pro Arg Cys Asp Asp Ile Met Leu Gln Asn Leu Ser Ser Gly Leu
    370                 375                 380

Leu Gln Asn Leu Ser Ala Gly Gln Leu His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Val Ser Glu His Val Leu Pro Trp Gln
            420                 425                 430

Leu Leu Glu Asn Met Tyr Asn Met Ser Phe His Ala Arg Asp Leu Thr
        435                 440                 445

Leu Gln Phe Asp Ala Glu Gly Asn Val Asp Met Glu Tyr Asp Leu Lys
    450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
                485                 490                 495

Asn Gln Val Pro Val Ser Gln Cys Ser Arg Gln Cys Lys Asp Gly Gln
            500                 505                 510

Val Arg Arg Val Lys Gly Phe His Ser Cys Cys Tyr Asp Cys Val Asp
        515                 520                 525

Cys Lys Ala Gly Ser Tyr Arg Lys His Pro Asp Asp Phe Thr Cys Thr
    530                 535                 540

Pro Cys Asn Gln Asp Gln Trp Ser Pro Glu Lys Ser Thr Ala Cys Leu
545                 550                 555                 560

Pro Arg Arg Pro Lys Phe Leu Ala Trp Gly Glu Pro Val Val Leu Ser
                565                 570                 575

Leu Leu Leu Leu Leu Cys Leu Val Leu Gly Leu Ala Leu Ala Ala Leu
            580                 585                 590

Gly Leu Ser Val His His Trp Asp Ser Pro Leu Val Gln Ala Ser Gly
        595                 600                 605

Gly Ser Gln Phe Cys Phe Gly Leu Ile Cys Leu Gly Leu Phe Cys Leu
```

```
                610              615              620
Ser Val Leu Leu Phe Pro Gly Arg Pro Ser Ser Ala Ser Cys Leu Ala
625              630              635              640

Gln Gln Pro Met Ala His Leu Pro Leu Thr Gly Cys Leu Ser Thr Leu
                645              650              655

Phe Leu Gln Ala Ala Glu Thr Phe Val Glu Ser Glu Leu Pro Leu Ser
                660              665              670

Trp Ala Asn Trp Leu Cys Ser Tyr Leu Arg Gly Leu Trp Ala Trp Leu
                675              680              685

Val Val Leu Leu Ala Thr Phe Val Glu Ala Ala Leu Cys Ala Trp Tyr
690              695              700

Leu Ile Ala Phe Pro Pro Glu Val Val Thr Asp Trp Ser Val Leu Pro
705              710              715              720

Thr Glu Val Leu Glu His Cys His Val Arg Ser Trp Val Ser Leu Gly
                725              730              735

Leu Val His Ile Thr Asn Ala Met Leu Ala Phe Leu Cys Phe Leu Gly
                740              745              750

Thr Phe Leu Val Gln Ser Gln Pro Gly Arg Tyr Asn Arg Ala Arg Gly
                755              760              765

Leu Thr Phe Ala Met Leu Ala Tyr Phe Ile Thr Trp Val Ser Phe Val
770              775              780

Pro Leu Leu Ala Asn Val Gln Val Ala Tyr Gln Pro Ala Val Gln Met
785              790              795              800

Gly Ala Ile Leu Val Cys Ala Leu Gly Ile Leu Val Thr Phe His Leu
                805              810              815

Pro Lys Cys Tyr Val Leu Leu Trp Leu Pro Lys Leu Asn Thr Gln Glu
                820              825              830

Phe Phe Leu Gly Arg Asn Ala Lys Lys Ala Ala Asp Glu Asn Ser Gly
                835              840              845

Gly Gly Glu Ala Ala Gln Gly His Asn Glu
    850              855

<210> SEQ ID NO 24
<211> LENGTH: 2577
<212> TYPE: DNA
<213> ORGANISM: Rattus sp.
<220> FEATURE:
<223> OTHER INFORMATION: rat T1R3 G-protein coupled receptor sweet
      taste receptor CDS

<400> SEQUENCE: 24
atgccgggtt tggctatctt gggcctcagt ctggctgctt tcctggagct tgggatgggg     60
tcctctttgt gtctgtcaca gcaattcaag gcacaagggg actatatatt gggtggacta    120
tttcccctgg gcacaactga ggaggccact ctcaaccaga aacacagcc caacggcatc    180 ctatgtacca ggttctcgcc ccttggtttg ttcctggcca tggctatgaa gatggctgta    240
gaggagatca acaatggatc tgccttgctc cctgggctgc gactgggcta tgacctgttt    300
gacacatgct cagagccagt ggtcaccatg aagcccagcc tcatgttcat ggccaaggtg    360
ggaagtcaaa gcattgctgc ctactgcaac tacacacagt accaaccccg tgtgctggct    420
gtcattggtc cccactcatc agagcttgcc ctcattacag caagttcctt cagcttcttc    480
ctcatgccac aggtcagcta tagtgccagc atggatcggc taagtgaccg gaaacatttt    540
ccatccttct ccgcacagt gcccagtgac cgggtgcagc tgcaggccgt tgtgacactg    600
ttgcagaatt tcagctggaa ctgggtggct gccttaggta gtgatgatga ctatggccgg    660
```

```
gaaggtctga gcatcttttc tggtctggcc aactcacgag gtatctgcat tgcacacgag      720
ggcctggtgc cacaacatga cactagtggc caacaattgg gcaaggtggt ggatgtgcta      780
cgccaagtga accaaagcaa agtacaggtg gtggtgctgt ttgcatctgc ccgtgctgtc      840
tactcccttt ttagctacag catccttcat gacctctcac ccaaggtatg ggtggccagt      900
gagtcctggc tgacctctga cctggtcatg acacttccca atattgcccg tgtgggcact      960
gttcttgggt ttctgcagcg cggtgcccta ctgcctgaat tttcccatta tgtgcagact     1020
cgccttgccc tagctgctga cccaacattc tgtgcctccc tgaaagctga gttggatctg     1080
gaggagcgcg tgatggggcc acgctgttca caatgtgact acatcatgct acagaacctg     1140
tcatctgggc tgatgcagaa cctatcagct gggcagttgc accaccaaat atttgcaacc     1200
tatgcagctg tgtacagtgt ggctcaggcc cttcacaaca ccctgcagtg caatgtctca     1260
cattgccaca catcagagcc tgttcaaccc tggcagctcc tggagaacat gtacaatatg     1320
agtttccgtg ctcgagactt gacactgcag tttgatgcca aagggagtgt agacatggaa     1380
tatgacctga agatgtgggt gtggcagagc cctacacctg tactacatac tgtaggcacc     1440
ttcaacggca cccttcagct gcagcactcg aaaatgtatt ggccaggcaa ccaggtgcca     1500
gtctcccagt gctcccggca gtgcaaagat ggccaggtgc gcagagtaaa gggctttcat     1560
tcctgctgct atgactgtgt ggactgcaag gcagggagct accggaagca tccagatgac     1620
ttcacctgta ctccatgtgg caaggatcag tggtccccag aaaaaagcac aacctgctta     1680
cctcgcaggc ccaagtttct ggcttggggg gagccagctg tgctgtcact tctcctgctg     1740
cttttgcctgg tgctgggcct gacactggct gccctggggc tctttgtcca ctactgggac     1800
agccctcttg ttcaggcctc aggtgggtca ctgttctgct ttggcctgat ctgcctaggc     1860
ctcttctgcc tcagtgtcct tctgttccca ggacgaccac gctctgccag ctgccttgcc     1920
caacaaccaa tggctcacct ccctctcaca ggctgcctga gcacactctt cctgcaagca     1980
gccgagatct ttgtggagtc tgagctgcca ctgagttggg caaactggct ctgcagctac     2040
cttcggggcc cctgggcttg gctggtggta ctgctggcca ctcttgtgga ggctgcacta     2100
tgtgcctggt acttgatggc tttccctcca gaggtggtga cagattggca ggtgctgccc     2160
acggaggtac tggaacactg ccgcatgcgt cctgggtca gcctgggctt ggtgcacatc     2220
accaatgcag tgttagcttt cctctgcttt ctgggcactt tcctggtaca gagccagcct     2280
ggtcgctata accgtgcccg tggcctcacc ttcgccatgc tagcttattt catcatctgg     2340
gtctcttttg tgcccctcct ggctaatgtg caggtggcct accagccagc tgtgcagatg     2400
ggtgctatct tattctgtgc cctgggcatc ctggccacct tccacctgcc caaatgctat     2460
gtacttctgt ggctgccaga gctcaacacc caggagttcc tctgggaag agccccaag      2520
gaagcatcag atgggaatag tggtagtagt gaggcaactc ggggacacag tgaatga       2577
```

<210> SEQ ID NO 25
<211> LENGTH: 858
<212> TYPE: PRT
<213> ORGANISM: Rattus sp.
<220> FEATURE:
<223> OTHER INFORMATION: rat T1R3 G-protein coupled receptor sweet
      taste receptor

<400> SEQUENCE: 25

Met Pro Gly Leu Ala Ile Leu Gly Leu Ser Leu Ala Ala Phe Leu Glu
 1               5                  10                  15

Leu Gly Met Gly Ser Ser Leu Cys Leu Ser Gln Gln Phe Lys Ala Gln
            20                  25                  30

```
Gly Asp Tyr Ile Leu Gly Gly Leu Phe Pro Leu Gly Thr Thr Glu Glu
         35                  40                  45

Ala Thr Leu Asn Gln Arg Thr Gln Pro Asn Gly Ile Leu Cys Thr Arg
     50                  55                  60

Phe Ser Pro Leu Gly Leu Phe Leu Ala Met Ala Met Lys Met Ala Val
 65                  70                  75                  80

Glu Glu Ile Asn Asn Gly Ser Ala Leu Leu Pro Gly Leu Arg Leu Gly
                 85                  90                  95

Tyr Asp Leu Phe Asp Thr Cys Ser Glu Pro Val Val Thr Met Lys Pro
                100                 105                 110

Ser Leu Met Phe Met Ala Lys Val Gly Ser Gln Ser Ile Ala Ala Tyr
                115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
                180                 185                 190

Gln Leu Gln Ala Val Val Thr Leu Leu Gln Asn Phe Ser Trp Asn Trp
    195                 200                 205

Val Ala Ala Leu Gly Ser Asp Asp Tyr Gly Arg Glu Gly Leu Ser
210                 215                 220

Ile Phe Ser Gly Leu Ala Asn Ser Arg Gly Ile Cys Ile Ala His Glu
225                 230                 235                 240

Gly Leu Val Pro Gln His Asp Thr Ser Gly Gln Gln Leu Gly Lys Val
                245                 250                 255

Val Asp Val Leu Arg Gln Val Asn Gln Ser Lys Val Gln Val Val Val
                260                 265                 270

Leu Phe Ala Ser Ala Arg Ala Val Tyr Ser Leu Phe Ser Tyr Ser Ile
    275                 280                 285

Leu His Asp Leu Ser Pro Lys Val Trp Val Ala Ser Glu Ser Trp Leu
    290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr Arg Leu Ala Leu Ala Ala Asp Pro Thr Phe Cys Ala
                340                 345                 350

Ser Leu Lys Ala Glu Leu Asp Leu Glu Glu Arg Val Met Gly Pro Arg
    355                 360                 365

Cys Ser Gln Cys Asp Tyr Ile Met Leu Gln Asn Leu Ser Ser Gly Leu
    370                 375                 380

Met Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Thr Ser Glu Pro Val Gln Pro Trp Gln
                420                 425                 430

Leu Leu Glu Asn Met Tyr Asn Met Ser Phe Arg Ala Arg Asp Leu Thr
    435                 440                 445

Leu Gln Phe Asp Ala Lys Gly Ser Val Asp Met Glu Tyr Asp Leu Lys
```

```
                    450              455              460
Met Trp Val Trp Gln Ser Pro Thr Pro Val Leu His Thr Val Gly Thr
465                 470              475                  480

Phe Asn Gly Thr Leu Gln Leu Gln His Ser Lys Met Tyr Trp Pro Gly
                    485              490                  495

Asn Gln Val Pro Val Ser Gln Cys Ser Arg Gln Cys Lys Asp Gly Gln
                    500              505                  510

Val Arg Arg Val Lys Gly Phe His Ser Cys Cys Tyr Asp Cys Val Asp
                    515              520              525

Cys Lys Ala Gly Ser Tyr Arg Lys His Pro Asp Asp Phe Thr Cys Thr
530                 535                  540

Pro Cys Gly Lys Asp Gln Trp Ser Pro Glu Lys Ser Thr Thr Cys Leu
545                 550              555                  560

Pro Arg Arg Pro Lys Phe Leu Ala Trp Gly Glu Pro Ala Val Leu Ser
                    565              570                  575

Leu Leu Leu Leu Leu Cys Leu Val Leu Gly Leu Thr Leu Ala Ala Leu
                    580              585              590

Gly Leu Phe Val His Tyr Trp Asp Ser Pro Leu Val Gln Ala Ser Gly
                    595              600              605

Gly Ser Leu Phe Cys Phe Gly Leu Ile Cys Leu Gly Leu Phe Cys Leu
                    610              615              620

Ser Val Leu Leu Phe Pro Gly Arg Pro Arg Ser Ala Ser Cys Leu Ala
625                 630              635                  640

Gln Gln Pro Met Ala His Leu Pro Leu Thr Gly Cys Leu Ser Thr Leu
                    645              650              655

Phe Leu Gln Ala Ala Glu Ile Phe Val Glu Ser Glu Leu Pro Leu Ser
                    660              665              670

Trp Ala Asn Trp Leu Cys Ser Tyr Leu Arg Gly Pro Trp Ala Trp Leu
                    675              680              685

Val Val Leu Leu Ala Thr Leu Val Glu Ala Ala Leu Cys Ala Trp Tyr
690                 695              700

Leu Met Ala Phe Pro Pro Glu Val Val Thr Asp Trp Gln Val Leu Pro
705                 710              715                  720

Thr Glu Val Leu Glu His Cys Arg Met Arg Ser Trp Val Ser Leu Gly
                    725              730              735

Leu Val His Ile Thr Asn Ala Val Leu Ala Phe Leu Cys Phe Leu Gly
                    740              745              750

Thr Phe Leu Val Gln Ser Gln Pro Gly Arg Tyr Asn Arg Ala Arg Gly
                    755              760              765

Leu Thr Phe Ala Met Leu Ala Tyr Phe Ile Ile Trp Val Ser Phe Val
770                 775              780

Pro Leu Leu Ala Asn Val Gln Val Ala Tyr Gln Pro Ala Val Gln Met
785                 790              795                  800

Gly Ala Ile Leu Phe Cys Ala Leu Gly Ile Leu Ala Thr Phe His Leu
                    805              810              815

Pro Lys Cys Tyr Val Leu Leu Trp Leu Pro Glu Leu Asn Thr Gln Glu
                    820              825              830

Phe Phe Leu Gly Arg Ser Pro Lys Glu Ala Ser Asp Gly Asn Ser Gly
                    835              840              845

Ser Ser Glu Ala Thr Arg Gly His Ser Glu
850                 855
```

<210> SEQ ID NO 26
<211> LENGTH: 2526

```
<212> TYPE: DNA
<213> ORGANISM: Homo sapiens
<220> FEATURE:
<223> OTHER INFORMATION: human T1R1 G-protein coupled receptor sweet
      taste receptor (hT1R1)

<400> SEQUENCE: 26
atgctgctct gcacggctcg cctggtcggc ctgcagcttc tcatttcctg ctgctgggcc        60
tttgcctgcc atagcacgga gtcttctcct gacttcaccc tccccggaga ttacctcctg       120
gcaggcctgt tccctctcca ttctggctgt ctgcaggtga ggcacagacc cgaggtgacc       180
ctgtgtgaca ggtcttgtag cttcaatgag catggctacc acctcttcca ggctatgcgg       240
cttggggttg aggagataaa caactccacg gccctgctgc caacatcac cctggggtac       300
cagctgtatg atgtgtgttc tgactctgcc aatgtgtatg ccacgctgag agtgctctcc       360
ctgccagggc aacaccacat agagctccaa ggagaccttc tccactattc ccctacggtg       420
ctggcagtga ttgggcctga cagcaccaac cgtgctgcca ccacagccgc cctgctgagc       480
cctttcctgg tgcccatgat tagctatgcg ccagcagcg agacgctcag cgtgaagcgg       540
cagtatccct ctttcctgcg caccatcccc aatgacaagt accaggtgga gaccatggtg       600
ctgctgctgc agaagttcgg gtggacctgg atctctctgg ttggcagcag tgacgactat       660
gggcagctag gggtgcaggc actggagaac caggccactg tcaggggat ctgcattgct       720
ttcaaggaca tcatgccctt ctctgcccag gtgggcgatg agaggatgca gtgcctcatg       780
cgccacctgg cccaggccgg ggccaccgtc gtggttgttt tttccagccg gcagttggcc       840
agggtgtttt tcgagtccgt ggtgctgacc aacctgactg gcaaggtgtg ggtcgcctca       900
gaagcctggg ccctctccag gcacatcact ggggtgccg gatccagcg cattgggatg       960
gtgctgggcg tggccatcca agagagggct gtccctggcc tgaaggcgtt tgaagaagcc      1020
tatgcccggg cagacaagaa ggccctagg ccttgccaca gggctcctg gtgcagcagc      1080
aatcagctct gcagagaatg ccaagctttc atggcacaca cgatgccaa gctcaaagcc      1140
ttctccatga gttctgccta caacgcatac cgggctgtgt atgcggtggc ccatggcctc      1200
caccagctcc tgggctgtgc ctctggagct tgttccaggg gccgagtcta cccctggcag      1260
cttttggagc agatccacaa ggtgcatttc cttctacaca aggacactgt ggcgtttaat      1320
gacaacagag atccctcag tagctataac ataattgcct gggactggaa tggacccaag      1380
tggaccttca cggtcctcgg ttcctccaca tggtctccag ttcagctaaa cataaatgag      1440
accaaaatcc agtggcacgg aaaggacaac caggtgccta gtctgtgtg ttccagcgac      1500
tgtcttgaag gcaccagcg agtggttacg ggtttccatc actgctgctt tgagtgtgtg      1560
ccctgtgggg ctgggacctt cctcaacaag agtgacctct acagatgcca gccttgtggg      1620
aaagaagagt gggcacctga ggaagccag acctgcttcc gcgcactgt ggtgttttg      1680
gctttgcgtg agcacacctc ttgggtgctg ctggcagcta cacgctgct gctgctgctg      1740
ctgcttggga ctgctggcct gtttgcctgg cacctagaca cccctgtggt gaggtcagca      1800
gggggccgcc tgtgctttct tatgctgggc tccctggcag caggtagtgg cagcctctat      1860
ggcttctttg gggaacccac aaggcctgcg tgcttgctac gccaggccct cttttgccctt      1920
ggtttcacca tcttcctgtc ctgcctgaca gttcgctcat ccaactaat catcatcttc      1980
aagttttcca ccaaggtacc tacattctac acgcctgggt ccaaaaccca cggtgctggc      2040
ctgtttgtga tgatcagctc agcggcccag ctgcttatct gtctaacttg gctggtggtg      2100
tggacccac tgcctgctag ggaataccag cgcttccccc atcggtgat gcttgagtgc      2160
```

```
acagagacca actccctggg cttcatactg gccttcctct acaatggcct cctctccatc    2220
agtgcctttg cctgcagcta cctgggtaag gacttgccag agaactacaa cgaggccaaa    2280
tgtgtcacct tcagcctgct cttcaacttc gtgtcctgga tcgccttctt caccacggcc    2340
agcgtctacg acggcaagta cctgcctgcg gccaacatga tggctgggct gagcagcctg    2400
agcagcggct tcggtgggta ttttctgcct aagtgctacg tgatcctctg ccgcccagac    2460
ctcaacagca cagagcactt ccaggcctcc attcaggact acacgaggcg ctgcggctcc    2520
acctga                                                                2526
```

```
<210> SEQ ID NO 27
<211> LENGTH: 841
<212> TYPE: PRT
<213> ORGANISM: Homo sapiens
<220> FEATURE:
<223> OTHER INFORMATION: human T1R1 G-protein coupled receptor sweet
      taste receptor (hT1R1)

<400> SEQUENCE: 27
```

```
Met Leu Leu Cys Thr Ala Arg Leu Val Gly Leu Gln Leu Leu Ile Ser
 1               5                  10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Leu Gln Lys Phe Gly Trp
        195                 200                 205

Thr Trp Ile Ser Leu Val Gly Ser Ser Asp Asp Tyr Gly Gln Leu Gly
    210                 215                 220

Val Gln Ala Leu Glu Asn Gln Ala Thr Gly Gln Gly Ile Cys Ile Ala
225                 230                 235                 240

Phe Lys Asp Ile Met Pro Phe Ser Ala Gln Val Gly Asp Glu Arg Met
                245                 250                 255

Gln Cys Leu Met Arg His Leu Ala Gln Ala Gly Ala Thr Val Val Val
            260                 265                 270

Val Phe Ser Ser Arg Gln Leu Ala Arg Val Phe Phe Glu Ser Val Val
        275                 280                 285

Leu Thr Asn Leu Thr Gly Lys Val Trp Val Ala Ser Glu Ala Trp Ala
```

```
              290                 295                 300
Leu Ser Arg His Ile Thr Gly Val Pro Gly Ile Gln Arg Ile Gly Met
305                 310                 315                 320

Val Leu Gly Val Ala Ile Gln Lys Arg Ala Val Pro Gly Leu Lys Ala
                325                 330                 335

Phe Glu Glu Ala Tyr Ala Arg Ala Asp Lys Lys Ala Pro Arg Pro Cys
                340                 345                 350

His Lys Gly Ser Trp Cys Ser Ser Asn Gln Leu Cys Arg Glu Cys Gln
                355                 360                 365

Ala Phe Met Ala His Thr Met Pro Lys Leu Lys Ala Phe Ser Met Ser
370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Gly Arg Val
                405                 410                 415

Tyr Pro Trp Gln Leu Leu Glu Gln Ile His Lys Val His Phe Leu Leu
                420                 425                 430

His Lys Asp Thr Val Ala Phe Asn Asp Asn Arg Asp Pro Leu Ser Ser
                435                 440                 445

Tyr Asn Ile Ile Ala Trp Asp Trp Asn Gly Pro Lys Trp Thr Phe Thr
450                 455                 460

Val Leu Gly Ser Ser Thr Trp Ser Pro Val Gln Leu Asn Ile Asn Glu
465                 470                 475                 480

Thr Lys Ile Gln Trp His Gly Lys Asp Asn Gln Val Pro Lys Ser Val
                485                 490                 495

Cys Ser Ser Asp Cys Leu Glu Gly His Gln Arg Val Val Thr Gly Phe
                500                 505                 510

His His Cys Cys Phe Glu Cys Val Pro Cys Gly Ala Gly Thr Phe Leu
                515                 520                 525

Asn Lys Ser Asp Leu Tyr Arg Cys Gln Pro Cys Gly Lys Glu Glu Trp
                530                 535                 540

Ala Pro Glu Gly Ser Gln Thr Cys Phe Pro Arg Thr Val Val Phe Leu
545                 550                 555                 560

Ala Leu Arg Glu His Thr Ser Trp Val Leu Leu Ala Ala Asn Thr Leu
                565                 570                 575

Leu Leu Leu Leu Leu Gly Thr Ala Gly Leu Phe Ala Trp His Leu
                580                 585                 590

Asp Thr Pro Val Val Arg Ser Ala Gly Gly Arg Leu Cys Phe Leu Met
                595                 600                 605

Leu Gly Ser Leu Ala Ala Gly Ser Gly Ser Leu Tyr Gly Phe Phe Gly
610                 615                 620

Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
                645                 650                 655

Ile Ile Ile Phe Lys Phe Ser Thr Lys Val Pro Thr Phe Tyr His Ala
                660                 665                 670

Trp Val Gln Asn His Gly Ala Gly Leu Phe Val Met Ile Ser Ser Ala
                675                 680                 685

Ala Gln Leu Leu Ile Cys Leu Thr Trp Leu Val Val Trp Thr Pro Leu
                690                 695                 700

Pro Ala Arg Glu Tyr Gln Arg Phe Pro His Leu Val Met Leu Glu Cys
705                 710                 715                 720
```

```
Thr Glu Thr Asn Ser Leu Gly Phe Ile Leu Ala Phe Leu Tyr Asn Gly
            725                 730                 735

Leu Leu Ser Ile Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Phe
            755                 760                 765

Asn Phe Val Ser Trp Ile Ala Phe Phe Thr Thr Ala Ser Val Tyr Asp
        770                 775                 780

Gly Lys Tyr Leu Pro Ala Ala Asn Met Met Ala Gly Leu Ser Ser Leu
785                 790                 795                 800

Ser Ser Gly Phe Gly Tyr Phe Leu Pro Lys Cys Tyr Val Ile Leu
                805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr
            835                 840

<210> SEQ ID NO 28
<211> LENGTH: 2520
<212> TYPE: DNA
<213> ORGANISM: Homo sapiens
<220> FEATURE:
<223> OTHER INFORMATION: human T1R2 G-protein coupled receptor sweet
      taste receptor

<400> SEQUENCE: 28
atggggccca gggcaaagac catctgctcc ctgttcttcc tcctatgggt cctggctgag      60
ccggctgaga actcggactt ctacctgcct ggggattacc tcctgggtgg cctcttctcc     120
ctccatgcca acatgaaggg cattgttcac cttaacttcc tgcaggtgcc catgtgcaag     180
gagtatgaag tgaaggtgat aggctacaac ctcatgcagg ccatgcgctt cgcggtggag     240
gagatcaaca atgacagcag cctgctgcct ggtgtgctgc tgggctatga gatcgtggat     300
gtgtgctaca tctccaacaa tgtccagccg gtgctctact tcctggcaca cgaggacaac     360
ctccttccca tccaagagga ctacagtaac tacatttccc gtgtggtggc tgtcattggc     420
cctgacaact ccgagtctgt catgactgtg gccaacttcc tctccctatt tctccttcca     480
cagatcacct cagcgccat cagcgatgag ctgcgagaca aggtgcgctt cccggctttg     540
ctgcgtacca cacccagcgc cgaccaccac gtcgaggcca tggtgcagct gatgctgcac     600
ttccgctgga actggatcat tgtgctggtg agcagcgaca cctatggccg gacaatggc     660 cagctgcttg gcgagcgcgt ggcccggcgc gacatctgca tcgccttcca ggagacgctg     720
cccacactgc agcccaacca gaacatgacg tcagaggagc gccagcgcct ggtgaccatt     780
gtggacaagc tgcagcagag cacagcgcgc gtcgtggtcg tgttctcgcc cgacctgacc     840
ctgtaccact tcttcaatga ggtgctgcgc cagaacttca cgggcgccgt gtggatcgcc     900
tccgagtcct gggccatcga cccggtcctg cacaacctca cggagctggg ccacttgggc     960
accttcctgg gcatcaccat ccagagcgtg cccatcccgg gcttcagtga gttccgcgag    1020 tgggggcccac aggctgggcc gccaccctc agcaggacca gccagagcta cctgcaac     1080 caggagtgcg acaactgcct gaacgccacc ttgtccttca acaccattct caggctctct    1140
ggggagcgtg tcgtctacag cgtgtactct gcggtctatg ctgtgccca tgccctgcac    1200 agcctcctcg gctgtgacaa aagcacctgc accaagagg tggtctaccc ctggcagctg    1260
cttgaggaga tctggaaggt caacttcact tcctgggacc accaaatctt cttcgacccg    1320
caaggggacg tggctctgca cttggagatt gtccagtggc aatgggaccg gagccagaat    1380
```

```
cccttccaga gcgtcgcctc ctactacccc ctgcagcgac agctgaagaa catccaagac    1440
atctcctggc acaccgtcaa caacacgatc cctatgtcca tgtgttccaa gaggtgccag    1500
tcagggcaaa agaagaagcc tgtgggcatc cacgtctgct gcttcgagtg catcgactgc    1560
cttcccggca ccttcctcaa ccacactgaa gatgaatatg aatgccaggc ctgcccgaat    1620
aacgagtggt cctaccagag tgagacctcc tgcttcaagc ggcagctggt cttcctggaa    1680
tggcatgagg cacccaccat cgctgtggcc ctgctggccg ccctgggctt cctcagcacc    1740
ctggccatcc tggtgatatt ctggaggcac ttccagacac ccatagttcg ctcggctggg    1800
ggcccatgt gcttcctgat gctgacactg ctgctggtgg catacatggt ggtcccggtg    1860
tacgtggggc cgcccaaggt ctccacctgc ctctgccgcc aggccctctt cccctctgc    1920
ttcacaattt gcatctcctg tatcgccgtg cgttctttcc agatcgtctg cgccttcaag    1980
atggccagcc gcttcccacg cgcctacagc tactgggtcc gctaccaggg gcctacgtc    2040
tctatggcat ttatcacggt actcaaaatg gtcattgtgg taattggcat gctggccacg    2100
ggcctcagtc ccaccacccg tactgacccc gatgacccca agatcacaat tgtctcctgt    2160
aaccccaact accgcaacag cctgctgttc aacaccagcc tggacctgct gctctcagtg    2220
gtgggtttca gcttcgccta catgggcaaa gagctgccca ccaactacaa cgaggccaag    2280
ttcatcaccc tcagcatgac cttctatttc acctcatccg tctccctctg caccttcatg    2340
tctgcctaca gcggggtgct ggtcaccatc gtggacctct tggtcactgt gctcaacctc    2400
ctggccatca gcctgggcta cttcggcccc aagtgctaca tgatcctctt ctaccccgag    2460
cgcaacacgc ccgcctactt caacagcatg atccagggct acaccatgag gagggactag    2520
```

```
<210> SEQ ID NO 29
<211> LENGTH: 839
<212> TYPE: PRT
<213> ORGANISM: Homo sapiens
<220> FEATURE:
<223> OTHER INFORMATION: human T1R2 G-protein coupled receptor sweet
      taste receptor

<400> SEQUENCE: 29
```

Met Gly Pro Arg Ala Lys Thr Ile Cys Ser Leu Phe Phe Leu Leu Trp
 1               5                  10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

-continued

```
Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
            340                 345                 350

Thr Ser Gln Ser Tyr Thr Cys Asn Gln Glu Cys Asp Asn Cys Leu Asn
        355                 360                 365

Ala Thr Leu Ser Phe Asn Thr Ile Leu Arg Leu Ser Gly Glu Arg Val
    370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
                485                 490                 495

Lys Arg Cys Gln Ser Gly Gln Lys Lys Pro Val Gly Ile His Val
            500                 505                 510

Cys Cys Phe Glu Cys Ile Asp Cys Leu Pro Gly Thr Phe Leu Asn His
        515                 520                 525

Thr Glu Asp Glu Tyr Glu Cys Gln Ala Cys Pro Asn Asn Glu Trp Ser
    530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
            580                 585                 590
```

Thr Pro Ile Val Arg Ser Ala Gly Gly Pro Met Cys Phe Leu Met Leu
        595                 600                 605

Thr Leu Leu Leu Val Ala Tyr Met Val Pro Val Tyr Val Gly Pro
        610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
                660                 665                 670

Val Arg Tyr Gln Gly Pro Tyr Val Ser Met Ala Phe Ile Thr Val Leu
                675                 680                 685

Lys Met Val Ile Val Val Ile Gly Met Leu Ala Thr Gly Leu Ser Pro
        690                 695                 700

Thr Thr Arg Thr Asp Pro Asp Asp Pro Lys Ile Thr Ile Val Ser Cys
705                 710                 715                 720

Asn Pro Asn Tyr Arg Asn Ser Leu Leu Phe Asn Thr Ser Leu Asp Leu
                725                 730                 735

Leu Leu Ser Val Val Gly Phe Ser Phe Ala Tyr Met Gly Lys Glu Leu
                740                 745                 750

Pro Thr Asn Tyr Asn Glu Ala Lys Phe Ile Thr Leu Ser Met Thr Phe
        755                 760                 765

Tyr Phe Thr Ser Ser Val Ser Leu Cys Thr Phe Met Ser Ala Tyr Ser
        770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
        820                 825                 830

Gly Tyr Thr Met Arg Arg Asp
        835

<210> SEQ ID NO 30
<211> LENGTH: 2553
<212> TYPE: DNA
<213> ORGANISM: Homo sapiens
<220> FEATURE:
<223> OTHER INFORMATION: human T1R3 G-protein coupled receptor sweet
      taste receptor (hT1R3)

<400> SEQUENCE: 30
atgctgggcc ctgctgtcct gggcctcagc ctctgggctc tcctgcaccc tgggacgggg      60
gccccattgt gcctgtcaca gcaacttagg atgaagggg actacgtgct ggggggggctg     120 ttccccctgg gcgaggccga ggaggctggc ctccgcagcg gacacggcc cagcagccct      180 gtgtgcacca ggttctcctc aaacggcctg ctctgggcac tggccatgaa aatggccgtg    240
gaggagatca caacaagtc ggatctgctg cccgggctgc gctgggcta cgacctcttt       300 gatacgtgct cggagcctgt ggtggccatg aagcccagcc tcatgttcct ggccaaggca    360
ggcagccgcg acatcgccgc ctactgcaac tacacgcagt accagcccccg tgtgctggct   420 gtcatcgggc ccactcgtc agagctcgcc atggtcaccg gcaagttctt cagcttcttc    480
ctcatgcccc actacggtgc tagcatggag ctgctgagcg cccggggagac cttcccctcc    540 ttcttccgca ccgtgcccag cgaccgtgtg cagctgacgg ccgccgcgga gctgctgcag    600

```
gagttcggct ggaactgggt ggccgccctg ggcagcgacg acgagtacgg ccggcagggc    660
ctgagcatct tctcggccct ggccgcggca cgcggcatct gcatcgcgca cgagggcctg    720
gtgccgctgc cccgtgccga tgactcgcgg ctggggaagg tgcaggacgt cctgcaccag    780
gtgaaccaga gcagcgtgca ggtggtgctg ctgttcgcct ccgtgcacgc cgcccacgcc    840
ctcttcaact acagcatcag cagcaggctc tcgcccaagg tgtgggtggc cagcgaggcc    900
tggctgacct ctgacctggt catggggctg cccggcatgg cccagatggg cacggtgctt    960
ggcttcctcc agagggtgc ccagctgcac gagttccccc agtacgtgaa gacgcacctg   1020
gccctggcca ccgaccccgg cttctgctct gccctgggcg agagggagca gggtctggag   1080
gaggacgtgg tgggccagcg ctgcccgcag tgtgactgca tcacgctgca gaacgtgagc   1140
gcagggctaa atcaccacca gacgttctct gtctacgcag ctgtgtatag cgtggcccag   1200
gccctgcaca acactcttca gtgcaacgcc tcaggctgcc ccgcgcagga ccccgtgaag   1260
ccctggcagc tcctggagaa catgtacaac ctgaccttcc acgtgggcgg gctgccgctg   1320
cggttcgaca gcagcggaaa cgtggacatg gagtacgacc tgaagctgtg ggtgtggcag   1380
ggctcagtgc ccaggctcca cgacgtgggc aggttcaacg gcagcctcag gacagagcgc   1440
ctgaagatcc gctggcacac gtctgacaac cagaagcccg tgtcccggtg ctcgcggcag   1500
tgccaggagg gccaggtgcg ccgggtcaag ggttccact cctgctgcta cgactgtgtg   1560
gactgcgagg cgggcagcta ccggcaaaac ccagacgaca tcgcctgcac cttttgtggc   1620
caggatgagt ggtccccgga gcgaagcaca cgctgcttcc gccgcaggtc tcggttcctg   1680
gcatggggcg agccggctgt gctgctgctg ctcctgctgc tgagcctggc gctgggcctt   1740
gtgctggctg cttttgggct gttcgttcac catcgggaca gcccactggt tcaggcctcg   1800
gggggccccc tggcctgctt tggcctggtg tgcctggccc tggtctgcct cagcgtcctc   1860
ctgttccctg gccagcccag ccctgcccga tgcctggccc agcagccctt gtcccacctc   1920
ccgctcacgg gctgctgag cacactcttc ctgcaggcgg ccgagatctt cgtggagtca   1980
gaactgcctc tgagctgggc agaccggctg agtggctgcc tgcggggggcc ctgggcctgg   2040 ctggtggtgc tgctggccat gctggtggag gtcgcactgt gcacctggta cctggtggcc   2100
ttcccgccgg aggtggtgac ggactggcac atgctgccca cggaggcgct ggtgcactgc   2160
cgcacacgct cctgggtcag cttcggccta gcgcacgcca ccaatgccac gctggccttt   2220
ctctgcttcc tgggcacttt cctggtgcgg agccagccgg gctgctacaa ccgtgcccgt   2280
ggcctcacct ttgccatgct ggcctacttc atcacctggg tctcctttgt gccccctcctg   2340 gccaatgtgc aggtggtcct caggcccgcc gtgcagatgg gcgccctcct gctctgtgtc   2400
ctgggcatcc tggctgcctt ccacctgccc aggtgttacc tgctcatgcg gcagccaggg   2460
ctcaacaccc ccgagttctt cctgggaggg ggccctggg atgcccaagg ccagaatgac   2520
gggaacacag gaaatcaggg gaaacatgag tga                                2553
```

<210> SEQ ID NO 31
<211> LENGTH: 850
<212> TYPE: PRT
<213> ORGANISM: Homo sapiens
<220> FEATURE:
<223> OTHER INFORMATION: human T1R3 G-protein coupled receptor sweet
      taste receptor (hT1R3)

<400> SEQUENCE: 31

Met Leu Gly Pro Ala Val Leu Gly Leu Ser Leu Trp Ala Leu Leu His
1               5                   10                  15

-continued

```
Pro Gly Thr Gly Ala Pro Leu Cys Leu Ser Gln Gln Leu Arg Met Lys
             20                  25                  30
Gly Asp Tyr Val Leu Gly Gly Leu Phe Pro Leu Gly Glu Ala Glu Glu
         35                  40                  45
Ala Gly Leu Arg Ser Arg Thr Arg Pro Ser Ser Pro Val Cys Thr Arg
 50                  55                  60
Phe Ser Ser Asn Gly Leu Leu Trp Ala Leu Ala Met Lys Met Ala Val
 65                  70                  75                  80
Glu Glu Ile Asn Asn Lys Ser Asp Leu Leu Pro Gly Leu Arg Leu Gly
                 85                  90                  95
Tyr Asp Leu Phe Asp Thr Cys Ser Glu Pro Val Val Ala Met Lys Pro
            100                 105                 110
Ser Leu Met Phe Leu Ala Lys Ala Gly Ser Arg Asp Ile Ala Ala Tyr
        115                 120                 125
Cys Asn Tyr Thr Gln Tyr Gln Pro Arg Val Leu Ala Val Ile Gly Pro
130                 135                 140
His Ser Ser Glu Leu Ala Met Val Thr Gly Lys Phe Phe Ser Phe Phe
145                 150                 155                 160
Leu Met Pro His Tyr Gly Ala Ser Met Glu Leu Leu Ser Ala Arg Glu
                165                 170                 175
Thr Phe Pro Ser Phe Phe Arg Thr Val Pro Ser Asp Arg Val Gln Leu
            180                 185                 190
Thr Ala Ala Ala Glu Leu Leu Gln Glu Phe Gly Trp Asn Trp Val Ala
        195                 200                 205
Ala Leu Gly Ser Asp Asp Glu Tyr Gly Arg Gln Gly Leu Ser Ile Phe
    210                 215                 220
Ser Ala Leu Ala Ala Ala Arg Gly Ile Cys Ile Ala His Glu Gly Leu
225                 230                 235                 240
Val Pro Leu Pro Arg Ala Asp Asp Ser Arg Leu Gly Lys Val Gln Asp
                245                 250                 255
Val Leu His Gln Val Asn Gln Ser Ser Val Gln Val Val Leu Leu Phe
            260                 265                 270
Ala Ser Val His Ala Ala His Ala Leu Phe Asn Tyr Ser Ile Ser Ser
        275                 280                 285
Arg Leu Ser Pro Lys Val Trp Val Ala Ser Glu Ala Trp Leu Thr Ser
    290                 295                 300
Asp Leu Val Met Gly Leu Pro Gly Met Ala Gln Met Gly Thr Val Leu
305                 310                 315                 320
Gly Phe Leu Gln Arg Gly Ala Gln Leu His Glu Phe Pro Gln Tyr Val
                325                 330                 335
Lys Thr His Leu Ala Leu Ala Thr Asp Pro Ala Phe Cys Ser Ala Leu
            340                 345                 350
Gly Glu Arg Glu Gln Gly Leu Glu Glu Asp Val Val Gly Gln Arg Cys
        355                 360                 365
Pro Gln Cys Asp Cys Ile Thr Leu Gln Asn Val Ser Ala Gly Leu Asn
    370                 375                 380
His His Gln Thr Phe Ser Val Tyr Ala Ala Val Tyr Ser Val Ala Gln
385                 390                 395                 400
Ala Leu His Asn Thr Leu Gln Cys Asn Ala Ser Gly Cys Pro Ala Gln
                405                 410                 415
Asp Pro Val Lys Pro Trp Gln Leu Leu Glu Asn Met Tyr Asn Leu Thr
            420                 425                 430
Phe His Val Gly Gly Leu Pro Leu Arg Phe Asp Ser Ser Gly Asn Val
        435                 440                 445
```

```
Asp Met Glu Tyr Asp Leu Lys Leu Trp Val Trp Gln Gly Ser Val Pro
    450                 455                 460

Arg Leu His Asp Val Gly Arg Phe Asn Gly Ser Leu Arg Thr Glu Arg
465                 470                 475                 480

Leu Lys Ile Arg Trp His Thr Ser Asp Asn Gln Lys Pro Val Ser Arg
                485                 490                 495

Cys Ser Arg Gln Cys Gln Glu Gly Gln Val Arg Arg Val Lys Gly Phe
            500                 505                 510

His Ser Cys Cys Tyr Asp Cys Val Asp Cys Glu Ala Gly Ser Tyr Arg
            515                 520                 525

Gln Asn Pro Asp Asp Ile Ala Cys Thr Phe Cys Gly Gln Asp Glu Trp
        530                 535                 540

Ser Pro Glu Arg Ser Thr Arg Cys Phe Arg Arg Ser Arg Phe Leu
545                 550                 555                 560

Ala Trp Gly Glu Pro Ala Val Leu Leu Leu Leu Leu Leu Ser Leu
                565                 570                 575

Ala Leu Gly Leu Val Leu Ala Ala Leu Gly Leu Phe Val His His Arg
            580                 585                 590

Asp Ser Pro Leu Val Gln Ala Ser Gly Gly Pro Leu Ala Cys Phe Gly
            595                 600                 605

Leu Val Cys Leu Gly Leu Val Cys Leu Ser Val Leu Leu Phe Pro Gly
        610                 615                 620

Gln Pro Ser Pro Ala Arg Cys Leu Ala Gln Gln Pro Leu Ser His Leu
625                 630                 635                 640

Pro Leu Thr Gly Cys Leu Ser Thr Leu Phe Leu Gln Ala Ala Glu Ile
                645                 650                 655

Phe Val Glu Ser Glu Leu Pro Leu Ser Trp Ala Asp Arg Leu Ser Gly
            660                 665                 670

Cys Leu Arg Gly Pro Trp Ala Trp Leu Val Val Leu Leu Ala Met Leu
        675                 680                 685

Val Glu Val Ala Leu Cys Thr Trp Tyr Leu Val Ala Phe Pro Pro Glu
    690                 695                 700

Val Val Thr Asp Trp His Met Leu Pro Thr Glu Ala Leu Val His Cys
705                 710                 715                 720

Arg Thr Arg Ser Trp Val Ser Phe Gly Leu Ala His Ala Thr Asn Ala
                725                 730                 735

Thr Leu Ala Phe Leu Cys Phe Leu Gly Thr Phe Leu Val Arg Ser Gln
            740                 745                 750

Pro Gly Cys Tyr Asn Arg Ala Arg Gly Leu Thr Phe Ala Met Leu Ala
        755                 760                 765

Tyr Phe Ile Thr Trp Val Ser Phe Val Pro Leu Leu Ala Asn Val Gln
    770                 775                 780

Val Val Leu Arg Pro Ala Val Gln Met Gly Ala Leu Leu Leu Cys Val
785                 790                 795                 800

Leu Gly Ile Leu Ala Ala Phe His Leu Pro Arg Cys Tyr Leu Leu Met
                805                 810                 815

Arg Gln Pro Gly Leu Asn Thr Pro Glu Phe Phe Leu Gly Gly Gly Pro
            820                 825                 830

Gly Asp Ala Gln Gly Gln Asn Asp Gly Asn Thr Gly Asn Gln Gly Lys
        835                 840                 845

His Glu
    850
```

```
<210> SEQ ID NO 32
<211> LENGTH: 200
<212> TYPE: PRT
<213> ORGANISM: Artificial Sequence
<220> FEATURE:
<223> OTHER INFORMATION: Description of Artificial Sequence:poly Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 32

Gly Gly Gly Gly Gly Gly Gly Gly Gly Gly Gly Gly Gly Gly Gly Gly
 1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly
            180                 185                 190

Gly Gly Gly Gly Gly Gly Gly Gly
        195                 200
```

MAMMALIAN T1R3 SWEET TASTE RECEPTORS

CROSS-REFERENCES TO RELATED APPLICATIONS

This application is a continuation of application Ser. No. 11/402,202, now U.S. Pat. No 7,459,277, filed Apr. 10, 2006, which is a divisional of U.S. application Ser. No. 10/679,102, filed Oct. 2, 2003 (abandoned); each is herein incorporated by reference in its entirety for all purposes.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention provides isolated nucleic acid and amino acid sequences of sweet taste receptors, the receptors comprising consisting of a monomer or homodimer of a T1R3 G-protein coupled receptor polypeptide, antibodies to such receptors, methods of detecting such nucleic acids and receptors, and methods of screening for modulators of sweet taste receptors.

BACKGROUND OF THE INVENTION

The sense of taste is responsible for detecting and responding to sweet, bitter, sour, salty and umami (amino acid) stimuli. It is also capable of distinguishing between these various taste modalities to generate innate behavioral responses. For instance, animals are vigorously averse to bitter-tasting compounds, but are attracted to sweet and umami stimuli. To examine taste signal detection and information processing, we have focused on the isolation and characterization of sweet, umami and bitter taste receptors. These receptors provide powerful molecular tools to delineate the organization of the taste system, and to help define the logic of taste coding.

Two families of candidate mammalian taste receptors, the T1Rs and T2Rs, have been implicated in sweet, umami and bitter detection. The T2Rs are a family of ~30 taste-specific GPCRs distantly related to opsins, and clustered in regions of the genome genetically linked to bitter taste in humans and mice (Adler et al., Cell 100, 693-702 (2000); Matsunami et al., Nature, 404, 601-604 (2000)). Several T2Rs have been shown to function as bitter taste receptors in heterologous expression assays, substantiating their role as bitter sensors (Chandrashekar et al., Cell, 100, 703-711 (2000); Bufe et al., Nat Genet, 32, 397-401 (2002)). Most T2Rs are co-expressed in the same subset of taste receptor cells (Adler, E. et al., Cell 100, 693-702 (2000)), suggesting that these cells function as generalized bitter detectors.

The T1Rs are a small family of 3 GPCRs expressed in taste cells of the tongue and palate epithelium, distantly related to metabotropic glutamate receptors, the calcium sensing receptor and vomeronasal receptors (Hoon et al., Cell., 96, 541-551 (1999); Kitagawa et al., Biochem Biophys Res Commun, 283, 236-242 (2001); Max et al., |Sac. Nat. Genet, 28, 58-63 (2001); Montmayeur et al. Nat Neurosci, 4, 492-498 (2001); Nelson et al., Cell, 106, 381-390 (2001); Sainz et al., J Neurochem, 77, 896-903 (2001)). T1Rs combine to generate at least two heteromeric receptors: T1R1 and T1R3 form an L-amino acid sensor, which in rodents recognizes most amino acids, and T1R2 and T1R3 associate to function as a broadly tuned sweet receptor (Nelson, G. et al., Cell, 106, 381-390 (2001); Nelson, G. et al., Nature, 416, 199-202 (2002); Li, X. et al., Proc Natl Acad Sci USA, 99, 4692-4696 (2002); see also WO 00/06592, WO 00/06593, and WO 03/004992).

Animals can detect a wide range of chemically distinct sweet tasting molecules, including natural sugars, artificial sweeteners, D-amino acids and intensely sweet proteins. How many different receptors does it take to taste the sweet universe? The human and rodent T1R2+3 heteromeric sweet receptors respond in cell-based assays to all classes of sweet compounds, and do so with affinities that approximate their respective in vivo psychophysical and/or behavioral thresholds (Nelson et al., Cell, 106, 381-390 (2001); Li et al., Proc Natl Acad Sci USA, 99, 4692-4696 (2002)). At a fundamental level, the evolution of sweet taste most likely reflects the need to detect and measure sugar content in potential food sources. Therefore, a single broadly tuned receptor for natural sugars might be all that is required. On the other hand, a number of studies with various sugars and artificial sweeteners insinuate the possibility of more than one sweet taste receptor (Schiffman et al., Pharmacol Biochem Behav, 15, 377-388 (1981); Ninomiya et al., J Neurophysiol, 81, 3087-3091 (1999)).

In humans, monosodium L-glutamate (MSG) and L-aspartate, but not other amino acids, elicit a distinctive savory taste sensation called umami (Maga, 1983). Notably, unlike the rodent T1R1+3, the human T1R1+3 amino acid taste receptor is substantially more sensitive to L-glutamate and L-aspartate than to other L-amino acids (Li et al., Proc Natl Acad Sci USA, 99, 4692-4696 (2002)). These findings led to the proposal that T1R1+3 may be the mammalian umami receptor (Nelson. et al., Nature, 416, 199-202 (2002); Li. et al., Proc Natl Acad Sci USA, 99, 4692-4696 (2002)). However, a number of studies, including the recent analysis of T1R3 KO mice (Damak et al., Science, 301, 850-853 (2003)) have suggested that umami taste is mediated by mGluR4t, a truncated variant of the metabotropic glutamate receptor (Chaudhari et al., Neurosci, 16, 3817-3826 (1996); Chaudhari. et al., Nat Neurosci, 3, 113-119 (2000)).

How are the different taste qualities encoded at the taste cell level? In mammals, taste receptor cells are assembled into taste buds that are distributed in different papillae in the tongue epithelium. Each taste bud contains 50-150 cells, including precursor cells, support cells, and taste receptor cells (Lindemann, Physiol Rev, 76, 718-766 (1996)). The receptor cells are innervated by afferent fibers that transmit information to the taste centers of the cortex through synapses in the brain stem and thalamus. In the simplest model of taste coding at the periphery, each taste modality would be encoded by a unique population of cells expressing specific receptors (e.g. sweet cells, bitter cells, salt-sensing cells, etc.). In this scenario, our perception of any one taste quality would result from the activation of distinct cell types in the tongue (labeled line model). Alternatively, individual taste cells could recognize multiple taste modalities, and the ensemble firing pattern of many such broadly tuned receptor cells would encode taste quality (across fiber model).

Recently, we showed that T1Rs and T2Rs are expressed in completely non-overlapping populations of receptor cells in the lingual epithelium (Nelson et al., Cell, 106, 381-390 (2001)), and demonstrated that bitter-receptor expressing cells mediate responses to bitter but not to sweet or amino acid tastants (Zhang et al., Cell, 112, 293-301 (2003)). Together, these results argued that taste receptor cells are not broadly tuned across all modalities, and strongly supported a labeled line model of taste coding at the periphery. A fundamental question we address now is how many types of cells and receptors are necessary to mediate sweet and umami, the two principal attractive taste modalities. We now show that sweet and umami tastes are exclusively mediated by T1Rs, and demonstrate that genetic ablation of individual T1R subunits selectively affects these two attractive taste modalities. The identification of cells and receptors for sweet and umami sensing also allowed us to devise a strategy to separate the role of receptor activation from cell stimulation in encoding taste responses. We show that animals engineered to express a modified k-opioid receptor in T1R2+3-expressing cells become specifically attracted to a k-opioid agonist, and prove that activation of sweet-receptor expressing cells, rather than the T1R receptors themselves, is the key determinant of behavioral attraction to sweet tastants. Finally, we now demonstrate that T1R1 alone, either as a monomer or as a homodimer, acts as a receptor for naturally occurring sugars.

BRIEF SUMMARY OF THE INVENTION

The present invention thus provides for the first time a homodimeric sweet taste receptor, the receptor comprising or consisting of two T1R3 polypeptides. The present invention also provides a monomeric sweet taste receptor comprising or consisting of one T1R3 polypeptide. The receptors transduce a signal in response to sweet taste ligands when T1R3 is expressed in a cell. In one embodiment, the sweet taste ligands are naturally occurring sweet tasting molecules. In another embodiment, the sweet taste ligands and artificial and mimic naturally occurring sweet tasting molecules. In one embodiment, the T1R3 polypeptides of the homodimer are non-covalently linked.

In one aspect, the present invention provides a sweet taste receptor comprising a T1R3 polypeptide, the T1R3 polypeptide comprising greater than about 80% amino acid sequence identity to an amino acid sequence of SEQ ID NO: 15, SEQ ID NO:20, SEQ ID NO:23, SEQ ID NO:25, or SEQ ID NO:31 or encoded by a nucleotide sequence hybridizing under moderately or highly stringent hybridization conditions to a nucleotide sequence encoding an amino acid sequence of SEQ ID NO:15, SEQ ID NO:20, SEQ ID NO:23, SEQ ID NO:25, or SEQ ID NO:31.

In one embodiment, the T1R3-comprising receptor specifically binds to polyclonal antibodies generated against SEQ ID NO: 15, SEQ ID NO:20, SEQ ID NO:23, SEQ ID NO:25, or SEQ ID NO:31. In another embodiment, the receptor has G-protein coupled receptor activity. In another embodiment, the T1R3 polypeptide has an amino acid sequence of SEQ ID NO: 15, SEQ ID NO:20, SEQ ID NO:23, SEQ ID NO:25, or SEQ ID NO:31. In another embodiment, the receptor is from a human, a rat, or a mouse.

In another embodiment, the sweet receptor comprises a T1R3 polypeptide and recognizes natural sugars, e.g., glucose, galactose, fructose, maltose, lactose, and sucrose.

In one aspect, the present invention provides an isolated polypeptide comprising an extracellular, a transmembrane domain, or a cytoplasmic domain of a sweet T1R3-comprising homodimeric or monomeric taste receptor, the extracellular, a transmembrane domain, or a cytoplasmic domain comprising greater than about 80% amino acid sequence identity to the extracellular, a transmembrane domain, or a cytoplasmic domain of SEQ ID NO:15, SEQ ID NO:20, SEQ ID NO:23, SEQ ID NO:25, or SEQ ID NO:31. In another embodiment, the extracellular, transmembrane, or cytoplasmic domain hybridize under highly stringent conditions to an extracellular, transmembrane, or cytoplasmic domain of an amino acid sequence of SEQ ID NO:15, 20, 23, 25, or 31.

In one embodiment, the polypeptide encodes the extracellular, a transmembrane domain, or a cytoplasmic domain of SEQ ID NO: 15, SEQ ID NO:20, SEQ ID NO:23, SEQ ID NO:25, or SEQ ID NO:31. In another embodiment, the extracellular, a transmembrane domain, or a cytoplasmic domain is covalently linked to a heterologous polypeptide, forming a chimeric polypeptide. In another embodiment, the chimeric polypeptide has G-protein coupled receptor activity.

In one aspect, the present invention provides an antibody that selectively binds to a homodimeric or monomeric sweet taste receptor, the receptor comprising one or two T1R3 polypeptides but no T1R1 or T1R2 polypeptides, the antibody raised against a receptor comprising a T1R3 polypeptide comprising greater than about 80% amino acid sequence identity to an amino acid sequence of SEQ ID NO:15, SEQ ID NO:20, SEQ ID NO:23, SEQ ID NO:25, SEQ ID NO:31 or encoded by a nucleotide sequence hybridizing under highly stringent hybridization conditions to a nucleotide sequence encoding an amino acid sequence of SEQ ID NO:15, SEQ ID NO:20, SEQ ID NO:23, SEQ ID NO:25, or SEQ ID NO:31.

In another aspect, the present invention provides a method for identifying a compound that modulates sweet taste signaling in taste cells, the method comprising the steps of: (i) contacting the compound with a homodimeric or monomeric receptor comprising a T1R3 polypeptide but not a T1R1 or a T1R2 polypeptide, the polypeptide comprising greater than about 80% amino acid sequence identity to SEQ ID NO:15, SEQ ID NO:20, SEQ ID NO:23, SEQ ID NO:25, or SEQ ID NO:31; or encoded by a nucleotide sequence hybridizing under highly stringent hybridization conditions to a nucleotide sequence encoding an amino acid sequence of SEQ ID NO:15, SEQ ID NO:20, SEQ ID NO:23, SEQ ID NO:25, or SEQ ID NO:31; and (ii) determining the functional effect of the compound upon the receptor.

In one embodiment, the functional effect is determined in vitro. In one embodiment, the polypeptide is expressed in a cell or cell membrane. In another embodiment, the receptor is linked to a solid phase, either covalently or non-covalently.

In another aspect, the present invention provides a method for identifying a compound that modulates sweet taste signaling in taste cells, the method comprising the steps of: (i) contacting a cell with the compound, the cell expressing a homodimeric or monomeric receptor comprising a T1R3 polypeptide but not expressing a T1R1 or a T1R2 polypeptide, the T1R3 polypeptide comprising greater than about 80% amino acid sequence identity to SEQ ID NO: 15, SEQ ID NO:20, SEQ ID NO:23, SEQ ID NO:25, or SEQ ID NO:31; or encoded by a nucleotide sequence hybridizing under highly stringent hybridization conditions to a nucleotide sequence encoding an amino acid sequence of SEQ ID NO: 15, SEQ ID NO:20, SEQ ID NO:23, SEQ ID NO:25, or SEQ ID NO:31; and (ii) determining the functional effect of the compound upon the receptor.

In one embodiment, the functional effect is determined by measuring changes in intracellular cAMP, IP3, or Ca2+. In another embodiment, the functional effect is a chemical or phenotypic effect. In another embodiment, the functional effect is a physical effect. In another embodiment, the functional effect is determined by measuring binding of the compound to the extracellular domain of the receptor. In another embodiment, the polypeptide is recombinant. In another embodiment, the cell is a eukaryotic cell, e.g., a mammalian cell, e.g., a human cell. In another embodiment, the cell expresses G protein Gα15.

(a) Schematic drawing showing the structure of the three T1R genes and the strategy for generating knockout animals. The targeting constructs deleted all seven predicted transmembrane helices of T1R1 and T1R2, and the entire extracellular ligand binding domain of T1R3. (b) In situ hybridization labeling demonstrating robust expression of T1Rs in taste buds of wild-type animals, but complete absence in the corresponding knock-out mice.

Figure 1A:
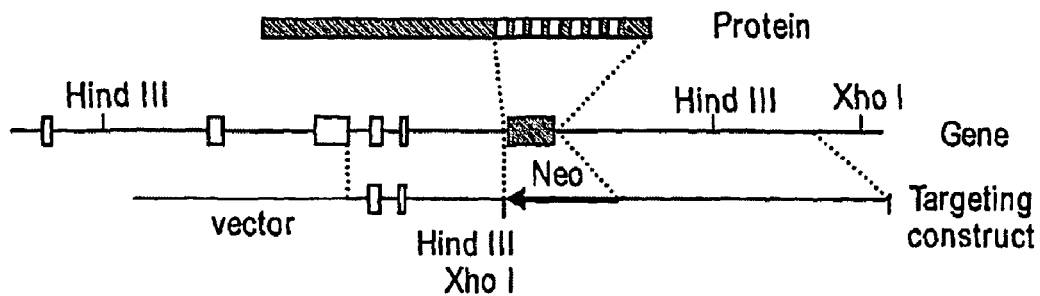
FIG. 1: Targeted KO of T1R1, T1R2 and T1R3.
Figure 1A:
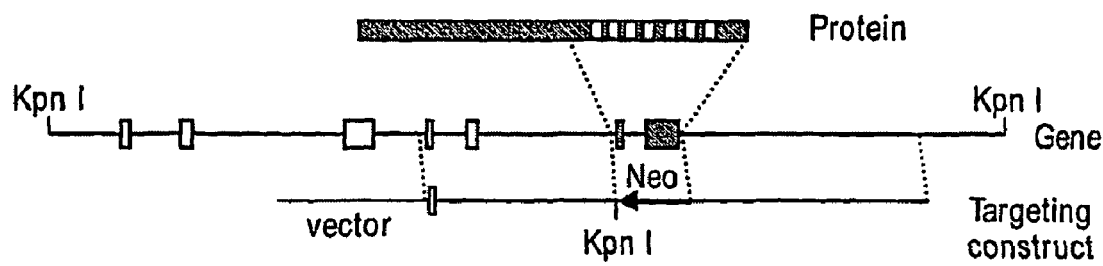
Figure 1A:
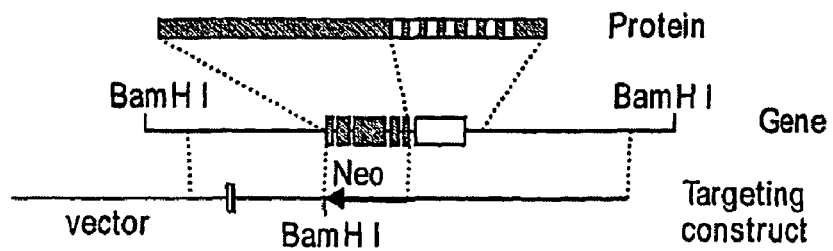
Figure 1B:
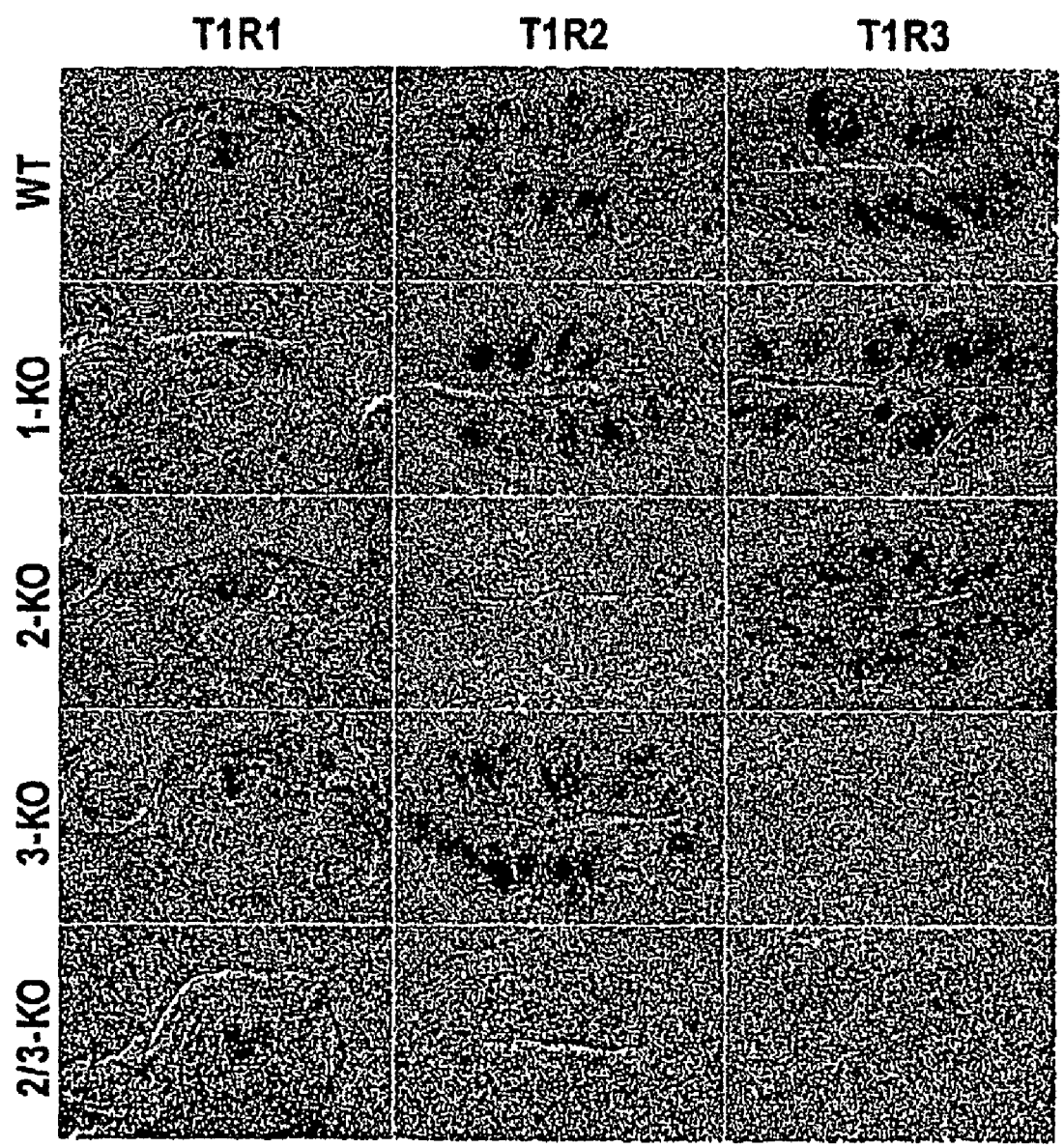
Figure 2A:
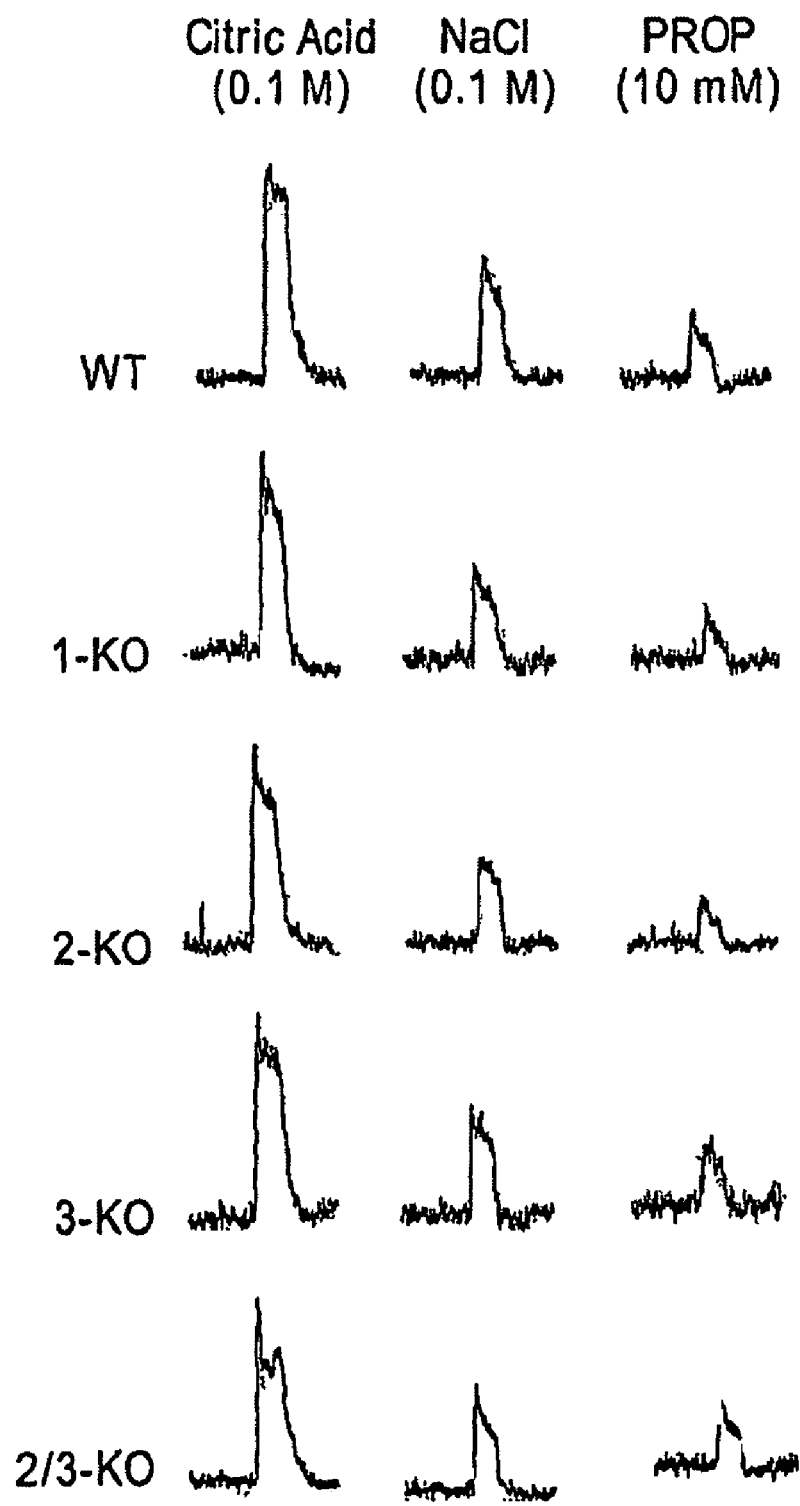
Figure 2B:
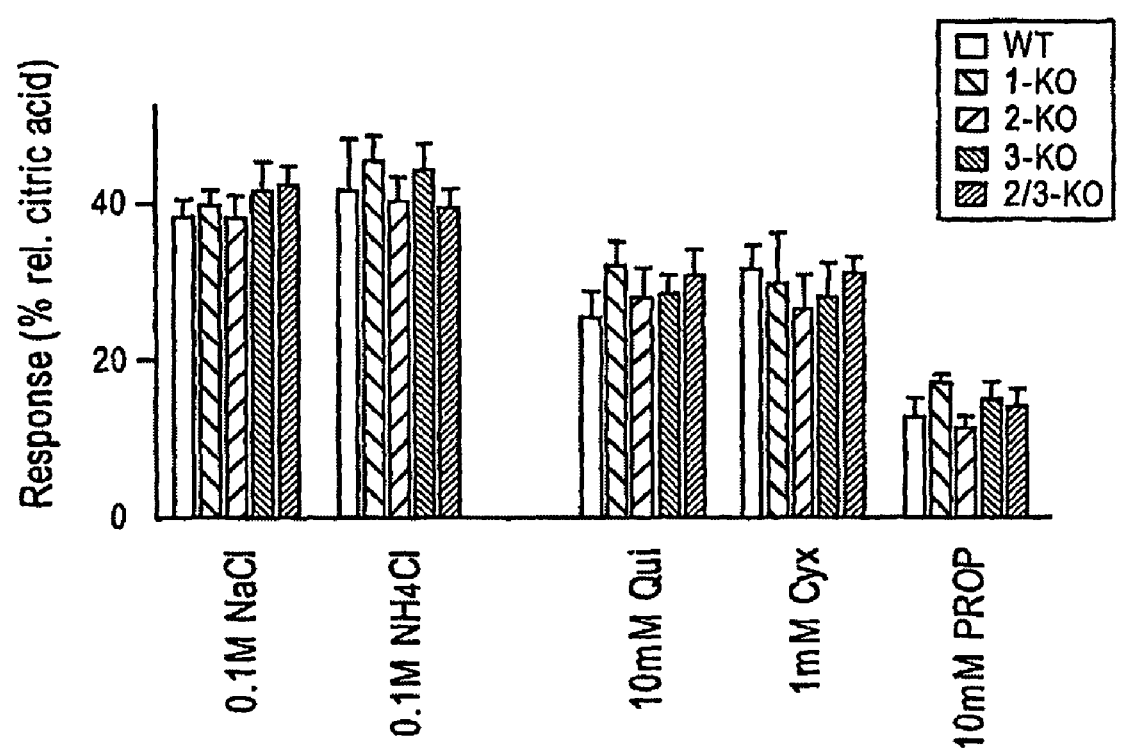
Figure 2C:
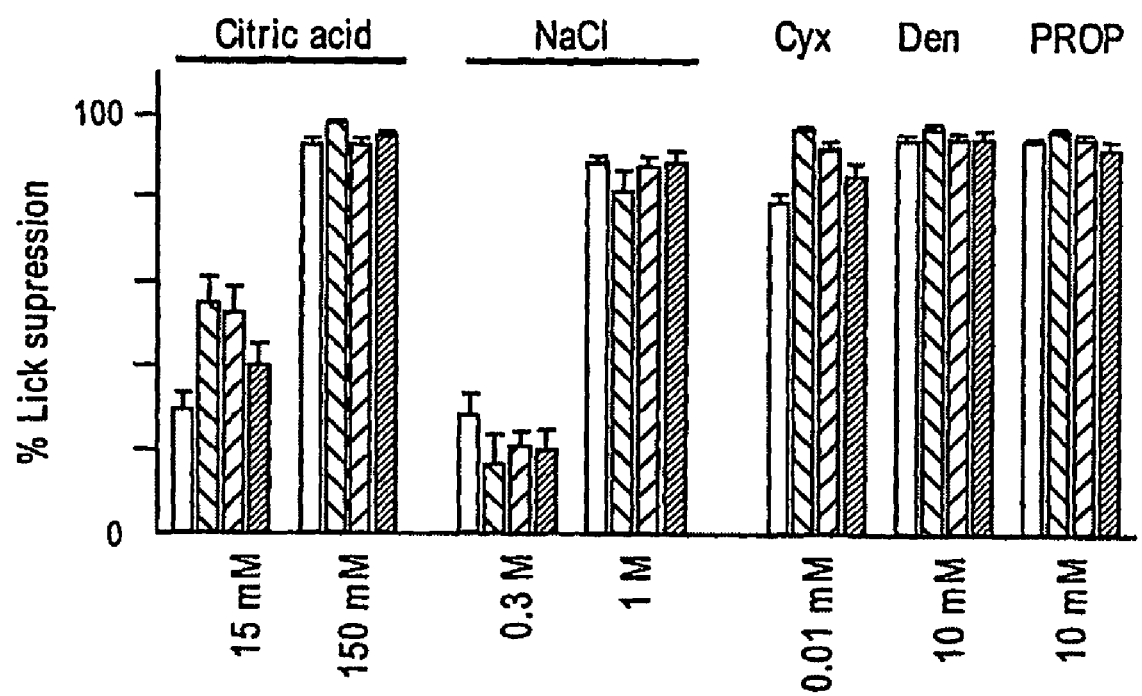

FIG. 2: T1R Mutants Respond Normally to Sour, Salty and Bitter Stimuli (a) Wild-type (WT), T1R1, T1R2 and T1R3 knockout mice (1-KO, 2-KO, 3-KO) show robust neural responses to sour (100 mM citric acid), salty (100 mM NaCl) and bitter (10 mM PROP) tastants. (b) Integrated neural responses, such as those shown in (a), were normalized to the response elicited by 100 mM citric acid; control and KO animals are indistinguishable from each other. The values are means ±s.e.m. (n=4). The data represent chorda tympani responses (see Experimental Procedures for details). (c), Taste preferences of wild-type and T1R knockout animals were measured relative to water using a brief access taste test (Zhang, Y. et al., Cell, 112, 293-301 (2003)). All four lines showed normal responses to sour, salty and bitter stimuli. The values are means ±s.e.m. (n=7). Similar results were obtained using a standard two bottle preference assay (data not shown). Cyx, cycloheximide; Den, denatonium benzoate; PROP, 6-n-propyl-thiouracil; Qui, quinine.

FIG. 3: T1R1+3 Functions as the Mammalian Umami Receptor (a-d) Taste preferences of wild-type (open circles, dashed lines), T1R1 KO (blue circles and bars), T1R2 KO (gray circles and bars) and T1R3 KO mice (brown circles and bars) were measured relative to water using a brief access taste test. T1R2 KO mice are equivalent to wild type controls. In contrast, T1R1 and T1R3 knockout animals exhibit a complete loss in preference for umami tastants (a) MSG+1 mM IMP, (b) MSG, (c) IMP, and (d) L-Asp (100 mM), and AP4 (30 mM). In addition, both knockout have marked impairments in other amino acid responses. L-Asn (100 mM) and L-Arg were used at 100 mM each. (e-f) Integrated chorda tympani responses to umami tastants and amino acids. T1R1 and T1R3 knockouts have a complete loss of responses to (e) umami agonists and L-amino acids if salt effects are avoided by using either amiloride or the potassium salt of MSG (MPG). In contrast, (f) if high concentrations of salt are used (e.g. 100 mM MSG), residual responses are detected.

FIG. 4: T1R2 and T1R3 are Essential for Sweet Taste Perception (a) Taste preferences of wild-type (open circles, dashed lines), T1R1 KO (gray circles and bars), T1R2 KO (green circles and bars) and T1R3 KO mice (brown circles and bars) were measured relative to water using a brief access taste test. T1R1 KO mice are equivalent to wild type controls. In contrast, T1R2 and T1R3 knockout animals exhibit a complete loss in preference for artificial sweeteners and D-amino acids, but retain residual responses to high concentration of natural sugars. These are highlighted in (b) as dose responses in expanded scale for maltose, sucrose and glucose. However, T1R2/T1R3 double KO animals (red circles) have a complete loss of all sweet responses. The values are means ±s.e.m. (n=7). D-Asn and D-Phe were 100 mM each, and D-Trp was used at 30 mM.

Figure 5A:
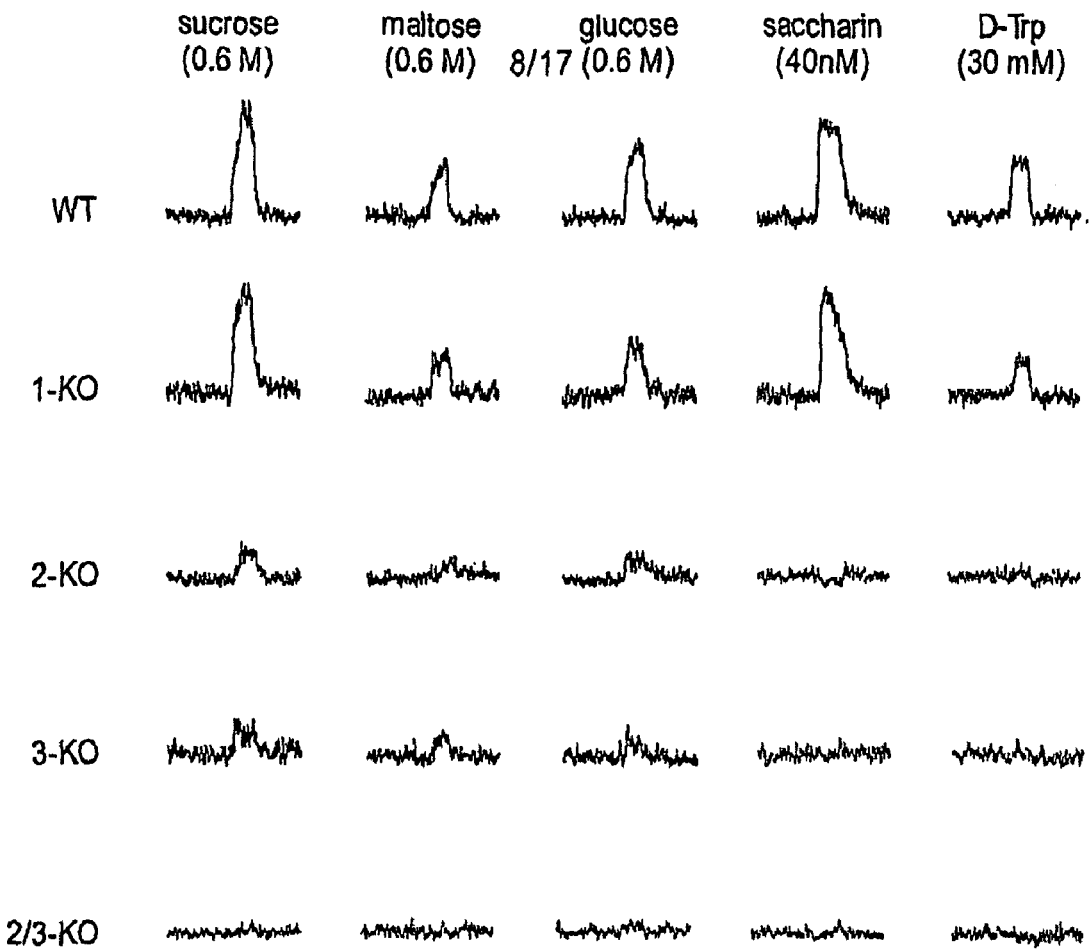
Figure 5B:
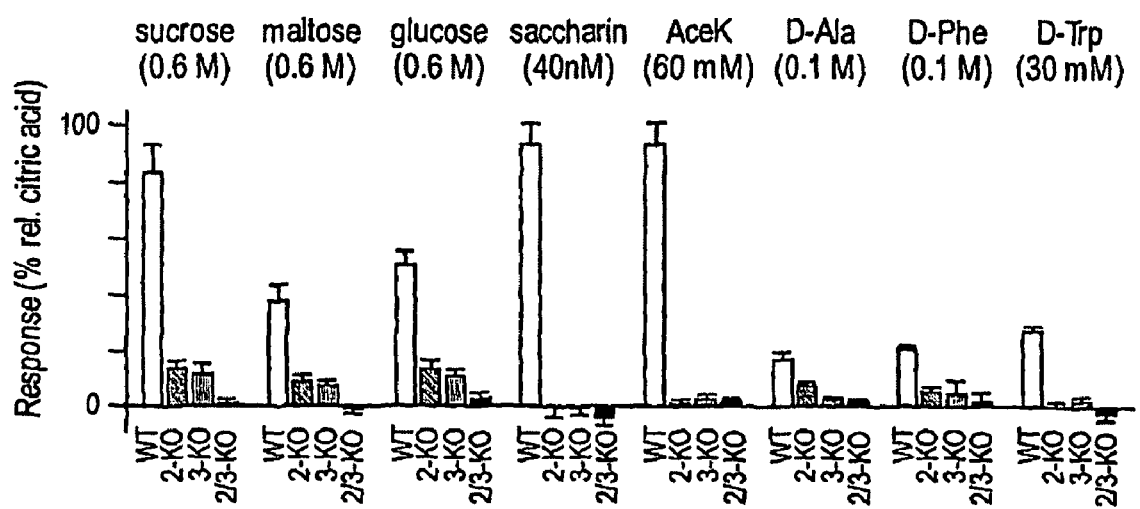

FIG. 5: T1R2 and T1R3 Encode the Mammalian Sweet Taste Receptors

Panel (a) shows integrated chorda tympani responses to natural sugars, artificial sweeteners and D-amino acids in wild type (WT) and T1R knockout animals (1-KO, 2-KO, 3-KO). T1R2 and T1R3 knockouts have a complete loss of responses to artificial sweeteners and D-amino acid (red traces), but show small neural responses to high concentrations of natural sugars. These, however, are completely abolished in T1R2/T1R3 double KO mice (bottom red traces). Panel (b) shows average neural responses to an expanded panel of tastants; wild type, white bars; T1R2 KO, green bars; T1R3 KO, brown bars; T1R2/T1R3 double KO, red bars. The values are means ±s.e.m. (n=4) of normalized chorda tympani responses.

Figure 6:
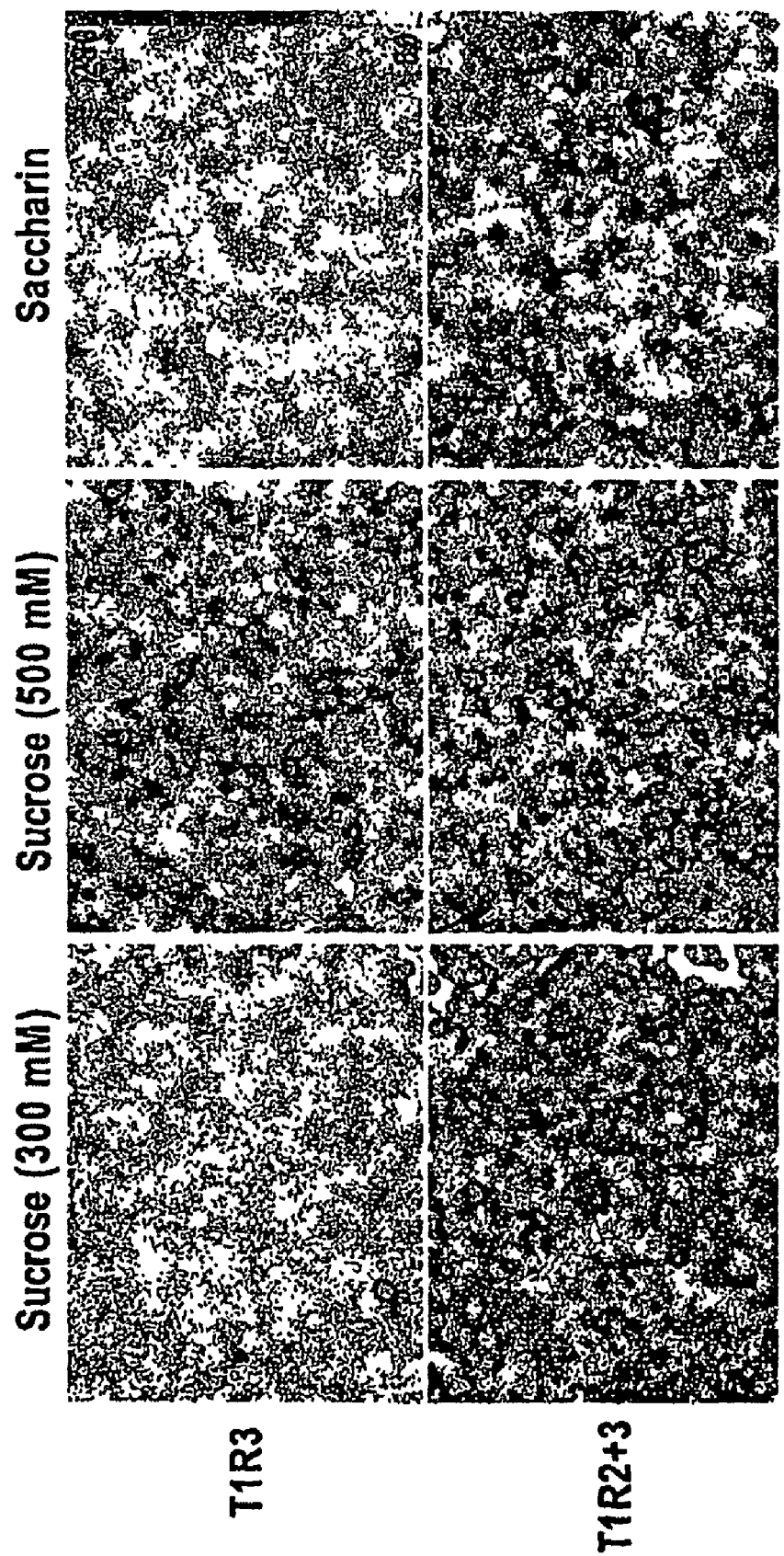

FIG. 6. T1R3 Responds to High Concentrations of Natural Sugars

HEK-293 cells co-expressing the promiscuous G protein $G_{gust-25}$ (see Experimental Procedures) and the mouse T1R3 GPCR, or co-transfected with both T1R2 plus T1R3, were stimulated with various sweet compounds. Upper panels show increases in $[Ca^{2+}]i$ upon stimulation of T1R3-expressing cells with 500 mM, but not 300 mM sucrose. No responses were detected with artificial sweeteners (300 mM saccharin, right panel), or in cells without receptors or $G_{gust-25}$; scale indicates $[Ca^{2+}]i$ (nM) determined from FURA-2 $F_{340}/F_{380}$ ratios. As expected, control cells expressing T1R2+3 (lower panels) respond robustly to lower concentrations of natural (300 mM sucrose) and artificial sweeteners (30 mM saccharin).

FIG. 7. Activation of T1R2-Expressing Cells Triggers Behavioral attraction (a) Wild type and T1R2 KO mice expressing a human T1R2 gene under the control of the rodent T1R2-promoter were (b-d) tested for behavioral responses to a variety of human sweet tastants: (b) Ace-K, acesulfame-K, (c) aspartame, and (d) MON, monellin (~10 μM); THAU, thaumatin (~5 μM); ASP, aspartame (10 mM); GA, glycyrrhizic acid (500 μM); NH, neohesperidin dihydrochalcone (400 μM). The human T1R2 taste receptor is (a) selectively expressed in T1R2-cells, and (b) effectively rescues sweet taste responses of T1R2 KO mice. Importantly, the presence of the transgene (c-d) humanizes the sweet taste preferences of the transgenic animals. See text for details. (e) Expression of RASSL (Redfern, C. H. et al., Nat Biotechnol, 17, 165-169 (1999)) in T1R2-cells generates animals that exhibit specific behavioral attraction to spiradoline. Note that no responses are seen in uninduced animals, or control mice, even at 100× the concentration needed to elicit strong responses in RASSL-expressing animals. The values are means ±s.e.m. (n=7)

FIG. 8

FIG. 8 provides a nucleotide sequence of hT1R1 (SEQ ID NO:26).

FIG. 9

FIG. 9 provides an amino acid sequence of hT1R1 (SEQ ID NO:27).

FIG. 10

FIG. 10 provides a nucleotide sequence of hT1R2 (SEQ ID NO:28).

FIG. 11

FIG. 11 provides a amino acid sequence of hT1R2 (SEQ ID NO:29).

FIG. 12

FIG. 12 provides a nucleotide sequence of hT1R3 (SEQ ID NO:30).

FIG. 13

FIG. 13 provides an amino acid sequence of hT1R3 (SEQ ID NO:31).

DETAILED DESCRIPTION OF THE INVENTION

Introduction

T1Rs and T2Rs are two families of G-protein-coupled receptors (GPCRs) selectively expressed in subsets of taste receptor cells (Hoon et al., *Cell* 96:541-551 (1999); Adler et al., *Cell* 100:693-702 (2000); Chandrashekar et al., *Cell* 100: 703-711 (2000); Matsunami et al., *Nature* 404:601-604 (2000); Nelson et al., *Cell* 106:381-390 (2001); Kitagawa et al., *Biochem. Biophys. Res. Cummun.* 283:236-242 (2001); Montmayeur et al., *Nature Neurosci.* 4:492-498 (2001); Max et al., *Nature Genet.* 28:58-63 (2001); Sainz et al., *J. Neurochem.* 77:896-903 (2001)). T2Rs are involved in bitter taste detection (Adler et al., *Cell* 100:693-702 (2000); Chandrashekar et al. *Cell*, 100:703-711 (2000)); T1R2 and T1R3 combine to function as a sweet taste receptor (see also Nelson et al., Cell 106:381-390 (2001); and T1R1 and T1R3 combine to function as an amino acid taste receptors, as described herein (see also Nelson et al., *Nature* 24 Feb. 2002 and WO 03/004992))). We have now identified a homodimeric taste receptor, in which two T1R3 polypeptides combine to function as a sweet taste receptor. The monomeric form of T1R3 also acts as a sweet receptor.

Using a heterologous expression system, we demonstrate that T1R3 combines with itself and also acts as a monomer to function as a sweet receptor, recognizing sweet-tasting molecules such as sucrose, galactose, fructose, glucose, maltose, and lactose. Candidate receptors are expressed in human embryonic kidney (HEK) cells containing the $G\alpha_{16}$-$G\alpha_z$ promiscuous G proteins (Offermanns et al., *J. Biol. Chem.* 270: 15175-15180 (1995); Mody et al., *Mol. Pharmacol.* 57:13-23 (2000)), and assayed for stimulus-evoked changes in intracellular calcium. In this system, receptor activation leads to activation of phospholipase Cβ (PLC-β and release of calcium from internal stores, which can be monitored at the single-cell level using calcium-indicator dyes (Chandrashekar et al., *Cell* 100:703-711 (2000); Nelson et al., *Cell* 106:381-390 (2001); Tsien et al., *Cell Calcium* 6:145-157 (1985)).

These nucleic acids and proteins encoding the receptors provide valuable probes for the identification of taste cells, as the nucleic acids are specifically expressed in taste cells. The receptors are useful for assaying for novel tastants, such as artificial sweetener molecules. For example, probes for GPCR polypeptides and proteins can be used to identity subsets of taste cells such as foliate cells, palate cells, and circumvallate cells, or specific taste receptor cells, e.g., sweet taste receptor cells. They also serve as tools for the generation of taste topographic maps that elucidate the relationship between the taste cells of the tongue and taste sensory neurons leading to taste centers in the brain. Furthermore, the nucleic acids and the proteins they encode can be used as probes to dissect taste-induced behaviors.

The invention also provides methods of screening for modulators, e.g., activators, inhibitors, stimulators, enhancers, agonists, and antagonists, of these novel monomeric or homodimeric sweet taste receptors comprising T1R3. In one embodiment, the monomeric or homodimeric T1R3-comprising receptors of the invention can be used to screen for naturally occurring or artificial sweet tasting molecules or modulators of sweet taste transduction, e.g., small organic molecules, amino acids, peptides, carbohydrates, lipids, polysaccharides, etc. For example, homodimeric or monomeric T1R3-comprising receptors of the invention recognize naturally occurring sweet tastants, as described below in the example section. Such receptors can be used to screen for artificial sweeteners, or altered naturally occurring sweeteners, that mimic the naturally occurring sugar ligands of the homodimeric or monomeric T1R3-comprising receptor. Such modulators of sweet taste transduction are useful for pharmacological and genetic modulation of sweet taste signaling pathways, and for the discovery of novel sweet taste ligands. These methods of screening can be used to identify agonists and antagonists of sweet taste cell activity. These modulatory compounds can then be used in the food and pharmaceutical industries to customize taste. Thus, the invention provides assays for taste modulation, where the T1R3-comprising receptor acts as an direct or indirect reporter molecule for the effect of modulators on sweet taste transduction. GPCRs can be used in assays, e.g., to measure changes in ligand binding, G-protein binding, regulatory molecule binding, ion concentration, membrane potential, current flow, ion flux, transcription, signal transduction, receptor-ligand interactions, neurotransmitter and hormone release; and second messenger concentrations, in vitro, in vivo, and ex vivo. In one embodiment, a receptor comprising T1R3 can be used as an indirect reporter via attachment to a second reporter molecule such as green fluorescent protein (see, e.g. Mistili & Spector, *Nature Biotechnology* 15:961-964 (1997)). In another embodiment, a receptor comprising T1R3 is recombinantly expressed in cells that do not express either T1R1 or T1R2, and modulation of taste transduction via GPCR activity is assayed by measuring changes in Ca2+ levels.

Methods of assaying for modulators of taste transduction include in vitro ligand binding assays using receptors comprising T1R3, portions thereof such as the extracellular domain, or chimeric proteins comprising one or more domains of T1R3, and in in vivo (cell-based and animal) assays such as oocyte T1R3 receptor expression; tissue culture cell T1R3 receptor expression; transcriptional activation of T1R3; phosphorylation and dephosphorylation of GPCRs; G-protein binding to GPCRs; ligand binding assays; voltage, membrane potential and conductance changes; ion flux assays; changes in intracellular second messengers such as cAMP and inositol triphosphate; changes in intracellular calcium levels; and neurotransmitter release.

Definitions

A "T1R family taste receptor" refers to a receptor comprising a member of the T1R family of G-protein coupled receptors, e.g., T1R1, T1R2, and T1R3, or any combination thereof as a homodimer receptor, a heterodimer receptor, or a monomer receptor. In one embodiment, the T1R family receptor comprises T1R3 (a "T1R3-comprising taste receptor" or a "T1R3-comprising sweet taste receptor"). In one embodiment, the T1R family receptor comprises a first T1R3 polypeptide and a second T1R3 polypeptide, which form a homodimeric receptor, either covalently or non-covalently linked. In another embodiment, the T1R family receptor comprises a single T1R3 polypeptide and no other T1R polypeptide, and forms a monomeric receptor. In another embodiment, the T1R family receptor comprises T1R3 and a heterologous polypeptide of the T1R family. In one embodiment, the receptor comprises T1R1 and T1R3. In another embodiment, the receptor comprises T1R2 and T1R3. In one embodiment the T1R3-comprising receptor is active when the two members of the receptor are co-expressed in the same cell, e.g., T1R3 and T1R3, or T1R1 and T1R3 or T1R2 and T1R3. In another embodiment, the T1R polypeptides are co-expressed in the same cell and form a heterodimeric or homodimeric receptor, in which the T1R polypeptides of the receptor are non-covalently linked or covalently linked. The receptor has the ability to recognize, e.g., naturally occurring and/or artificial sweet tasting molecule such as sucrose, fructose, galactose, mannose, glucose, lactose, saccharin, dulcin, acesulfame-K, as well as other molecules, sweet and non-sweet. These molecules are examples of compounds that "modulate sweet taste signal transduction" by acting as ligands for the taste-transducing G protein coupled receptor comprising T1R3.

The terms "GPCR-B3 or T1R1," "GPCR-B4 or T1R2," and "T1R3" or a nucleic acid encoding "GPCR-B3 or T1R1," "GPCR-B4 or T1R2," and "T1R3" refer to nucleic acid and polypeptide polymorphic variants, alleles, mutants, and interspecies homologs that are members of the T1R family of G protein coupled receptors and: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by SEQ ID NO: 1, 2, 3, 7, 8, 9, 15, 18, 20, 23, 25, 27, or 31; (2) bind to antibodies, e.g., polyclonal antibodies, raised against an immunogen comprising an amino acid sequence encoded by SEQ ID NO: 1, 2, 3, 7, 8, 9, 15, 18, 20, 23, 25, 27, or 31, and conservatively modified variants thereof; (3) specifically hybridize under stringent hybridization conditions to an antisense strand corresponding to a nucleic acid sequence encoding a T1R protein, e.g., SEQ ID NO:4, 5, 6, 10, 11, 12, 13, 14, 16, 17, 19, 21, 22, 24, 26, 28, or 30, and conservatively modified variants thereof; (4) have a nucleic acid sequence that has greater than about 60% sequence identity, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to SEQ ID NO:4, 5, 6, 10, 11, 12, 13, 14, 16, 17, 19, 21, 22, 24, 26, or 28, or 30. The T1R family polypeptide of the invention (e.g., T1R1, T1R2, or T1R3) or T1R3-comprising receptor (e.g., T1R3, T1R3+T1R3, T1R1+3 or T1R2+3) further has G protein coupled receptor activity, either alone or when co-expressed in the same cell, or when co-expressed as a monomer, homodimer, or heterodimer with another T1R family member. Accession numbers for amino acid sequences and nucleotide sequences of human, rat, and mouse T1R1, T1R2, and T1R3 can be found in GenBank (for human T1R1 amino acid sequences, see, e.g., Accession No. DAA00012 and NP_619642; for human T1R1 nucleotide sequences, see, e.g. Accession No. BK000153; for human T1R2 amino acid sequences, see, e.g. Accession No. DAA00019, AAM12239, and NP_619642.1; for human T1R2 nucleotide sequences, see, e.g., Accession No. BK000151, NM_138697.1, AF458149S1-6; for human T1R3 amino acid sequences, see, e.g., Accession No. DAA00013, for human T1R3 nucleotide sequences, see, e.g., Accession NO. BK000152). See also WO 00/06592, WO 00/06593, WO 01/66563, WO 03/001876, WO 02/064631, WO 03/004992, WO 03/025137, WO 02/086079 and WO 01/83749 for amino acid and nucleotide sequences of T1R1, T1R2, and T1R3, each herein incorporated by reference in its entirety.

T1R proteins have "G-protein coupled receptor activity," e.g., they bind to G-proteins in response to extracellular stimuli, such as ligand binding (e.g., sweet ligands), and promote production of second messengers such as IP3, cAMP, and Ca2+ via stimulation of enzymes such as phospholipase C and adenylate cyclase. Such activity can be measured in a heterologous cell, by coupling a GPCR (or a chimeric GPCR) to either a G-protein or promiscuous G-protein such as $G\alpha 15$ or $G\alpha_{16}$-$G\alpha_z$ and an enzyme such as PLC, and measuring increases in intracellular calcium using (Offermans & Simon, *J. Biol. Chem.* 270:15175-15180 (1995)). Receptor activity can be effectively measured, e.g., by recording ligand-induced changes in $[Ca^{2+}]_i$ using fluorescent $Ca^{2+}$-indicator dyes and fluorometric imaging.

Such GPCRs have transmembrane, extracellular and cytoplasmic domains that can be structurally identified using methods known to those of skill in the art, such as sequence analysis programs that identify hydrophobic and hydrophilic domains (see, e.g., Kyte & Doolittle, *J. Mol. Biol.* 157:105-132 (1982)). Such domains are useful for making chimeric proteins and for in vitro assays of the invention (see, e.g., WO 94/05695 and U.S. Pat. No. 5,508,384).

The phrase "functional effects" in the context of assays for testing compounds that modulate activity (e.g., signal transduction) of a sweet taste receptor or protein of the invention includes the determination of a parameter that is indirectly or directly under the influence of a GPCR or sweet taste receptor, e.g., a physical, phenotypic, or chemical effect, such as the ability to transduce a cellular signal in response to external stimuli such as ligand binding, or the ability to bind a ligand. It includes binding activity and signal transduction. "Functional effects" include in vitro, in vivo, and ex vivo activities.

By "determining the functional effect" is meant assaying for a compound that increases or decreases a parameter that is indirectly or directly under the influence of a T1R GPCR protein or a sweet taste receptor comprising one or more T1R GPCR proteins, e.g., physical and chemical or phenotypic effect. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for the protein; measuring inducible markers or transcriptional activation of the protein; measuring binding activity or binding assays, e.g., binding to antibodies; measuring changes in ligand binding activity or analogs thereof, either naturally occurring or synthetic; measuring cellular proliferation; measuring cell surface marker expression, measurement of changes in protein levels for T1R-associated sequences; measurement of RNA stability; G-protein binding; GPCR phosphorylation or dephosphorylation; signal transduction, e.g., receptor-ligand interactions, second messenger concentrations (e.g., cAMP, cGMP, IP3, PI, or intracellular $Ca^{2+}$); neurotransmitter release; hormone release; voltage, membrane potential and conductance changes; ion flux; regulatory molecule binding; identification of downstream or reporter gene expression (CAT, luciferase, β-gal, GFP and the like), e.g., via chemiluminescence, fluorescence, calorimetric reactions, antibody binding, and inducible markers.

"Inhibitors," "activators," and "modulators" of T1R family polynucleotide and polypeptide sequences and T1R family taste receptors are used to refer to activating, inhibitory, or modulating molecules identified using in vitro and in vivo assays of T1R polynucleotide and polypeptide sequences and T1R family taste receptors, including monomeric, homodimeric and heterodimeric receptors. Inhibitors are compounds that, e.g., bind to, partially or totally block activity, decrease, prevent, delay activation, inactivate, desensitize, or down regulate the activity or expression of the T1R family of taste receptors such as a receptor comprising a T1R3 polypeptide, e.g., antagonists. "Activators" are compounds that increase, open, activate, facilitate, enhance activation, sensitize, agonize, or up regulate a T1R family taste receptor, such as a receptor comprising a T1R3 polypeptide, e.g., agonists. Inhibitors, activators, or modulators also include genetically modified versions of T1R family taste receptors, e.g., versions with altered activity, as well as naturally occurring and synthetic ligands, antagonists, agonists, antibodies, antisense molecules, ribozymes, small chemical molecules and the like. Such assays for inhibitors and activators include, e.g., expressing T1R family taste receptors in vitro, in cells, or cell membranes, applying putative modulator compounds, and then determining the functional effects on activity, as described above. In one embodiment, taste receptor comprising a T1R3 polypeptide has the ability to recognize a sweet tasting molecule such as sucrose, glucose, fructose, lactose, mannose, galactose, saccharin, dulcin, acesulfame-K. In another embodiment, a taste receptor comprising a T1R3 polypeptide has the ability to recognize other molecules, such as potential artificial sweeteners. These molecules are examples of compounds that modulate taste signal transduction by acting as extracellular ligands for the G protein coupled receptor and activating the receptor. In other embodiments, compounds that modulate taste signal transduction are molecules that act as intracellular ligands of the receptor, or inhibit or activate binding of an extracellular ligand, or inhibit or activate binding of intracellular ligands of the receptor.

Samples or assays comprising the T1R family of taste receptors are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of a T1R family receptor is achieved when the activity value relative to the control is about 80%, preferably 50%, more preferably 25-0%. Activation of a T1R family receptor is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, such as an artificial sweetener or naturally occurring sugar, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation taste. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

A "heterodimer" is a dimer receptor comprising two different polypeptide subunits, e.g., two different polypeptides, where the molecules are associated via either covalent, e.g., through a linker or a chemical bond, or non-covalent, e.g., ionic, van der Waals, electrostatic, or hydrogen bonds linkages. The T1R3-comprising receptors of the invention function when co-expressed in the same cell, preferably when co-expressed so that they form a heterodimer, either covalently or non-covalently linked. For example, T1R1 and T1R3 form a heteromeric receptor, and T1R2 and T1R3 form a heteromeric receptor.

A "homodimer" is a dimer receptor comprising two of the same polypeptide subunits, e.g., two T1R3 polypeptides, where the molecules are associated via either covalent, e.g., through a linker or a chemical bond, or non-covalent, e.g., ionic, van der Waals, electrostatic, or hydrogen bonds linkages. The T1R3-comprising receptors of the invention function when co-expressed in the same cell, preferably when co-expressed so that they form a homodimer, either covalently or non-covalently linked.

A "monomer" is a receptor comprising one polypeptide subunit, e.g., one T1R3 polypeptide.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequences SEQ ID NO:1-25), when compared and aligned for maximum correspondence over a comparison window or designated region) as measured using a BLAST or BLAST 2.0 sequence comparison algorithms with default parameters described below, or by manual alignment and visual inspection (see, e.g. NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g. *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, enantiomers (D- and L-forms), and achiral amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine(Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g. Creighton, *Proteins* (1984)).

Macromolecular structures such as polypeptide structures can be described in terms of various levels of organization. For a general discussion of this organization, see, e.g. Alberts et al., *Molecular Biology of the Cell* (3$^{rd}$ ed., 1994) and Cantor and Schimmel, *Biophysical Chemistry Part I: The Conforma-*

*tion of Biological Macromolecules* (1980). "Primary structure" refers to the amino acid sequence of a particular peptide. "Secondary structure" refers to locally ordered, three dimensional structures within a polypeptide. These structures are commonly known as domains, e.g., extracellular domains, transmembrane domains, and cytoplasmic domains. Domains are portions of a polypeptide that form a compact unit of the polypeptide and are typically 15 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

"Nucleic acid" refers to deoxyribonucleotides or ribonucleotides and polymers thereof in either single- or double-stranded form, as well as the complements of any such sequence. Also included are DNA, cDNA, RNA, polynucleotides, nucleotides, and the like. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include 30-40 cycles of the following conditions: a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications* (1990).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H 1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g. McCafferty et al., *Nature* 348:552-554 (1990))

For preparation of antibodies, e.g., recombinant, monoclonal, or polyclonal antibodies, many technique known in the art can be used (see, e.g. Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology*(1991); Harlow & Lane, *Antibodies, A Laboratory Manual* (1988); and Goding, *Monoclonal Antibodies: Principles and Practice* (2d ed. 1986)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a T1R protein or a homodimeric or heterodimeric T1R3-comprising taste receptor comprising a sequence of or encoded by SEQ ID NO: 1-25, polymorphic variants, alleles, orthologs, and conservatively modified variants, or splice variants, or portions thereof, can be selected to obtain only those polyclonal antibodies that are specifically immunoreactive with T1R proteins and/or homodimeric or heterodimeric T1R3-comprising taste receptors and not with other proteins. In one embodiment, the antibodies react with a homodimeric T1R3-comprising taste receptor, but not with individual protein members of the T1R family. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g. Harlow & Lane, *Antibodies, A Laboratory Manual* (1988) for a description of immunoassay formats and conditions that can be used to determine specific immunoreactivity).

Isolation of Nucleic Acids Encoding T1R Family Members

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

T1R nucleic acids, polymorphic variants, orthologs, and alleles that are substantially identical to an amino acid sequences disclosed herein can be isolated using T1R nucleic acid probes and oligonucleotides under stringent hybridization conditions, by screening libraries. Alternatively, expression libraries can be used to clone T1R protein, polymorphic variants, orthologs, and alleles by detecting expressed homologs immunologically with antisera or purified antibodies made against human T1R or portions thereof.

To make a cDNA library, one should choose a source that is rich in T1R RNA, e.g., taste buds such as circumvallate, foliate, fungiform, and palate. The mRNA is then made into cDNA using reverse transcriptase, ligated into a recombinant vector, and transfected into a recombinant host for propagation, screening and cloning. Methods for making and screening cDNA libraries are well known (see, e.g. Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

An alternative method of isolating T1R nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human T1R directly from mRNA, from cDNA, from genomic libraries or cDNA libraries. Degenerate oligonucleotides can be designed to amplify T1R homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of T1R encoding mRNA in physiological samples, for nucleic acid sequencing, or for other purposes. Genes amplified by the PCR reaction can be purified from agarose gels and cloned into an appropriate vector.

Gene expression of T1R can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like. Nucleic acids encoding T1R protein can be used with high density oligonucleotide array technology (e.g., GeneChip™) to identify T1R protein, orthologs, alleles, conservatively modified variants, and polymorphic variants in this invention (see, e.g. Gunthand et al., *AIDS Res. Hum. Retroviruses* 14: 869-876 (1998); Kozal et al., *Nat. Med.* 2:753-759 (1996); Matson et al., *Anal. Biochem.* 224: 110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998)).

The gene for T1R is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding a T1R protein, one typically subclones T1R into an expression vector that contains a strong promoter to direct transcription, a transcription/translation terminator, and if for a nucleic acid encoding a protein, a ribosome binding site for translational initiation. The T1R nucleic acids can be co-expressed or separately expressed, preferably co-expressed on the same or a different vector. Suitable bacterial promoters are well known in the art and described, e.g., in Sambrook et al., and Ausubel et al, supra. Bacterial expression systems for expressing the T1R protein are available in, e.g., *E. coli*, *Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the T1R encoding nucleic acid in host cells. A typical expression cassette thus contains a promoter operably linked to the nucleic acid sequence encoding T1R and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/$A^+$, PMTO10/$A^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g. Gossen & Bujard, *Proc. Nat'l Acad. Sci. USA* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a T1R encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of T1R protein, which are then purified using standard techniques (see, e.g. Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g. Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g. Sambrook et al., supra). It is only necessary that the particular genetic engineering procedure used be capable of successfully introducing at least one gene into the host cell capable of expressing T1R.

After the expression vector is introduced into the cells, the transfected cells are cultured under conditions favoring expression of T1R, which is recovered from the culture using standard techniques identified below.

Purification of T1R Polypeptides

Either naturally occurring or recombinant T1R polypeptides or T1R3-comprising receptors can be purified for use in functional assays. Naturally occurring T1R proteins or T1R3-comprising receptors can be purified, e.g., from human tissue. Recombinant T1R proteins or T1R3-comprising receptors can be purified from any suitable expression system. T1R polypeptides are typically co-expressed in the same cell to form T1R3-comprising receptors.

The T1R protein or T1R3-comprising receptor may be purified to substantial purity by standard techniques, including selective precipitation with such substances as ammonium sulfate; column chromatography, immunopurification methods, and others (see, e.g. Scopes, *Protein Purification: Principles and Practice* (1982); U.S. Pat. No. 4,673,641; Ausubel et al., supra; and Sambrook et al., supra).

A number of procedures can be employed when recombinant T1R protein or T1R3-comprising receptor is being purified. For example, proteins having established molecular adhesion properties can be reversible fused to the T1R protein or T1R3-comprising receptor. With the appropriate ligand, T1R protein or T1R3-comprising receptor can be selectively adsorbed to a purification column and then freed from the column in a relatively pure form. The fused protein is then removed by enzymatic activity. Finally, T1R protein or T1R3-comprising receptor could be purified using immunoaffinity columns.

A. Purification of T1R from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of T1R protein or T1R3-comprising receptor inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g. Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human T1R proteins or T1R3-comprising receptors are separated from other bacterial proteins by standard separation techniques, e.g., with Ni-NTA agarose resin.

Alternatively, it is possible to purify T1R protein or T1R3-comprising receptor from bacteria periplasm. After lysis of the bacteria, when the T1R protein or T1R3-comprising receptor is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying T1R Proteins Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the T1R proteins or T 1R3-comprising receptors can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The T1R proteins or T1R3-comprising receptors can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of T1R Protein

A. Assays

Modulation of a T1R3-comprising taste receptor, and corresponding modulation of taste, can be assessed using a variety of in vitro and in vivo assays. Such assays can be used to test for inhibitors and activators of T1R3-comprising taste receptors, and, consequently, inhibitors and activators of taste. Such modulators of T1R3-comprising sweet taste receptors, which are involved in taste signal transduction. Modulators of T1R3-comprising taste receptors are tested using either recombinant or naturally occurring T1R3-comprising taste receptors, preferably human receptors.

In one embodiment, the monomeric or homodimeric T1R3-comprising receptors of the invention can be used to screen for naturally occurring or artificial sweet tasting molecules, e.g., small organic molecules, amino acids, peptides, carbohydrates, lipids, polysaccharides, etc. For example, homodimeric or monomeric T1R3-comprising receptors of the invention recognize naturally occurring sweet tastants, as described below in the example section. Such receptors can be used to screen for artificial sweeteners, or altered naturally occurring sweeteners, that mimic the naturally occurring sugar ligands of the homodimeric or monomeric T1R3-comprising receptor.

Preferably, the T1R3-comprising taste receptor will have a sequence as encoded by a sequence provided herein or a conservatively modified variant thereof. Alternatively, the T1R3-comprising taste receptor of the assay will be derived from a eukaryote and include an amino acid subsequence having substantial amino acid sequence identity to the sequences provided herein or is encoded by a nucleotide sequence that hybridizes under stringent conditions (moderate or high) to a nucleotide sequence as described herein. Generally, the amino acid sequence identity will be at least 60%, preferably at least 65%, 70%, 75%, 80%, 85%, or 90%, most preferably at least 95%.

Measurement of sweet taste signal transduction or loss-of-sweet taste signal transduction phenotype on T1R3-comprising taste receptor or cell expressing the T1R3-comprising taste receptor, either recombinant or naturally occurring, can be performed using a variety of assays, in vitro, in vivo, and ex vivo, as described herein. A suitable physical, chemical or phenotypic change that affects activity or binding can be used to assess the influence of a test compound on the polypeptide of this invention. When the functional effects are determined using intact cells or animals, one can also measure a variety of effects such as, in the case of signal transduction, e.g., ligand binding, hormone release, transcriptional changes to both known and uncharacterized genetic markers (e.g., northern blots), changes in cell metabolism such as pH changes, and changes in intracellular second messengers such as $Ca^{2+}$, IP3, cGMP, or cAMP.

In Vitro Assays

Assays to identify compounds with T1R3-comprising taste receptor modulating activity can be performed in vitro. Such assays can use a full length T1R3-comprising taste receptor or a variant thereof, or a fragment of a T1R3-comprising taste receptor, such as an extracellular domain, fused to a heterologous protein to form a chimera (see, e.g., WO 01/66563, WO 03/001876, WO 02/064631, and WO 03/004992). Purified recombinant or naturally occurring T1R3-comprising taste receptor can be used in the in vitro methods of the invention. In addition to purified T1R3-comprising taste receptor, the recombinant or naturally occurring T1R3-comprising taste receptor can be part of a cellular lysate or a cell membrane. As described below, the binding assay can be either solid state or soluble. Preferably, the protein or membrane is bound to a solid support, either covalently or non-covalently. Often, the in vitro assays of the invention are ligand binding or ligand affinity assays, either non-competitive or competitive (with known extracellular ligands as described herein, or with a known intracellular ligand GTP). Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the T1R3-comprising taste receptor or chimera comprising a fragment thereof is contacted with a potential modulator and incubated for a suitable amount of time. In one embodiment, the potential modulator is bound to a solid support, and the T1R3-comprising taste receptor is added. In another embodiment, the T1R3-comprising taste receptor is bound to a solid support. A wide variety of modulators can be used, as described below, including small organic molecules, peptides, antibodies, and T1R3-comprising taste receptor ligand analogs. A wide variety of assays can be used to identify T1R3-comprising taste receptor-modulator binding, including labeled protein-protein binding assays, electrophoretic mobility shifts, immunoassays, enzymatic assays such as phosphorylation assays, and the like. In some cases, the binding of the candidate modulator is determined through the use of competitive binding assays, where interference with binding of a known ligand is measured in the presence of a potential modulator. Ligands for T1R3-comprising taste receptors are provided herein. Either the modulator or the known ligand is bound first, and then the competitor is added. After the T1R3-comprising taste receptor is washed, interference with binding, either of the potential modulator or of the known ligand, is determined. Often, either the potential modulator or the known ligand is labeled.

Cell-Based In Vivo Assays

In another embodiment, a T1R3-comprising taste receptor is expressed in a cell (e.g., by expression or co-expression one or two members of the T1R family such as T1R1 and T1R3 or T1R2 and T1R3, preferably by expression of T1R3 alone without expression of any other T1R family members), and functional, e.g., physical and chemical or phenotypic, changes are assayed to identify T1R3-comprising taste receptor taste modulators. Cells expressing T1R3-comprising taste receptor can also be used in binding assays. Any suitable functional effect can be measured, as described herein. For example, ligand binding, G-protein binding, and GPCR signal transduction, e.g., changes in intracellular $Ca^{2+}$ levels, are all suitable assays to identify potential modulators using a cell based system. Suitable cells for such cell based assays include both primary cells and cell lines, as described herein. The T1R3-comprising taste receptor can be naturally occurring or recombinant. Also, as described above, chimeric T1R3-comprising taste receptors with GPCR activity can be used in cell based assays. For example, the extracellular domain of an T1R protein can be fused to the transmembrane and/or cytoplasmic domain of a heterologous protein, preferably a heterologous GPCR. Such a chimeric GPCR would have GPCR activity and could be used in cell based assays of the invention.

In another embodiment, cellular T1R polypeptide levels are determined by measuring the level of protein or mRNA. The level of T1R protein or proteins related to T1R signal transduction are measured using immunoassays such as western blotting, ELISA and the like with an antibody that selectively binds to the T1R3-comprising taste receptor or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, T1R3-comprising receptor expression can be measured using a reporter gene system. Such a system can be devised using an T1R protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g. Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

In another embodiment, a functional effect related to GPCR signal transduction can be measured. An activated or inhibited T1R3-comprising G-coupled protein receptor will alter the properties of target enzymes, second messengers, channels, and other effector proteins. The examples include the activation of cGMP phosphodiesterase, adenylate cyclase, phospholipase C, IP3, and modulation of diverse channels by G proteins. Downstream consequences can also be examined such as generation of diacyl glycerol and IP3 by phospholipase C, and in turn, for calcium mobilization by IP3. Activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. For a general review of GPCR signal transduction and methods of assaying signal transduction, see, e.g., *Methods in Enzymology*, vols. 237 and 238 (1994) and volume 96 (1983); Bourne et al., *Nature* 10:349:117-27 (1991); Bourne et al., *Nature* 348:125-32 (1990); Pitcher et al., *Annu. Rev. Biochem.* 67:653-92 (1998).

As described above, activation of some G-protein coupled receptors stimulates the formation of inositol triphosphate (IP3) through phospholipase C-mediated hydrolysis of phosphatidylinositol (Berridge & Irvine, *Nature* 312:315-21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

In one example, T1R3-comprising taste receptor GPCR activity is measured by expressing a T1R3-comprising taste receptor in a heterologous cell with a promiscuous G-protein that links the receptor to a phospholipase C signal transduction pathway (see Offermanns & Simon, *J. Biol. Chem.* 270: 15175-15180 (1995)). Modulation of signal transduction is assayed by measuring changes in intracellular $Ca^{2+}$ levels, which change in response to modulation of the GPCR signal transduction pathway via administration of a molecule that associates with an T1R3-comprising taste receptor. Changes in $Ca^{2+}$ levels are optionally measured using fluorescent $Ca^{2+}$ indicator dyes and fluorometric imaging.

In another example, phosphatidyl inositol (PI) hydrolysis can be analyzed according to U.S. Pat. No. 5,436,128, herein incorporated by reference. Briefly, the assay involves labeling of cells with $^3H$-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

Other assays can involve determining the activity of receptors which, when activated, result in a change in the level of intracellular cyclic nucleotides, e.g., cAMP or cGMP, by activating or inhibiting enzymes such as adenylate cyclase. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay.

In one example, the changes in intracellular cAMP or cGMP can be measured using immunoassays. The method described in Offermanns & Simon, *J. Biol. Chem.* 270:15175-15180 (1995) may be used to determine the level of cAMP. Also, the method described in Felley-Bosco et al., *Am. J. Resp. Cell and Mol. Biol.* 11: 159-164 (1994) may be used to determine the level of cGMP. Further, an assay kit for measuring cAMP and/or cGMP is described in U.S. Pat. No. 4,115,538, herein incorporated by reference.

In one example, assays for G-protein coupled receptor activity include cells that are loaded with ion or voltage sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as $G\alpha15$ and $G\alpha16$ can be used in the assay of choice (Wilkie et al., *Proc. Nat'l Acad. Sci. USA* 88:10049-10053 (1991)). Such promiscuous G-proteins allow coupling of a wide range of receptors.

Animal Models

Animal models of taste also find use in screening for modulators of taste, such as the T1R knockout mouse strains as described herein. Transgenic animal technology including gene knockout technology, for example as a result of homologous recombination with an appropriate gene targeting vector, or gene overexpression, will result in the absence or increased expression of the T1R3-comprising receptor or components thereof. When desired, tissue-specific expression or knockout of the T1R3-comprising receptors or components thereof may be necessary. Transgenic animals generated by such methods find use as animal models of taste modulation and are additionally useful in screening for modulators of taste modulation.

B. Modulators

The compounds tested as modulators of T1R3-comprising taste receptors can be any small organic molecule, or a biological entity, such as a protein, e.g., an antibody or peptide, an amino acid, a lipid, a fat, a sugar, e.g., a mono-, di-, or polysaccharide, a nucleic acid, e.g., an antisense oligonucleotide or a ribozyme, or a small organic molecule. Alternatively, modulators can be genetically altered versions of a T1R3-comprising taste receptor. Typically, test compounds will be small organic molecules, amino acids, peptides, lipids, and mono-, di- and polysaccharides.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g. U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g. Liang et al., *Science,* 274:1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. Nos. 5,506,337; benzodiazepines, 5,288,514, and the like).

Devices for the preparation of combinatorial libraries are commercially available (see, e.g. 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g. ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using a T1R3-comprising taste receptor, or a cell or tissue expressing a T1R3-comprising taste receptor, either naturally occurring or recombinant. In another embodiment, the invention provides solid phase based in vitro assays in a high throughput format, where the T1R3-comprising taste receptor is attached to a solid phase substrate. Any one of the assays described herein can be adapted for high throughput screening, e.g., ligand binding, cellular proliferation, cell surface marker flux e.g., screening, radiolabeled GTP binding, second messenger flux, e.g., $Ca^{2+}$, IP3, cGMP, or cAMP, cytokine production, etc.

In the high throughput assays of the invention, either soluble or solid state, it is possible to screen up to several thousand different modulators or ligands in a single day. This methodology can be used for T1R3-comprising taste receptors in vitro, or for cell-based or membrane-based assays comprising T1R3-comprising taste receptors. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:32). Such flexible linkers are known to persons of skill in the art. For example, poly(ethylene glycol) linkers are available from Shearwater Polymers, Inc. Huntsville, Ala. These Linkers optionally have amide linkage, sulfhydryl linkages, or heterofunctional linkages.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. A minoalkylsilanes and hydroxyalkylsilanes can be used to functionalize a variety of surfaces, such as glass surfaces. The construction of such solid phase biopolymer arrays is well described in the literature. See, e.g. Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Immunological Detection of T1R3—Comprising Receptors

In addition to the detection of T1R genes and gene expression using nucleic acid hybridization technology, one can also use immunoassays to detect T1R3-comprising taste receptors of the invention. Such assays are useful for screening for modulators of T1R3-comprising taste receptors, as well as for therapeutic and diagnostic applications. Immunoassays can be used to qualitatively or quantitatively analyze T1R3-comprising taste receptors. A general overview of the applicable technology can be found in Harlow & Lane, *Antibodies: A Laboratory Manual* (1988).

A. Production of Antibodies

Methods of producing polyclonal and monoclonal antibodies that react specifically with the T1R proteins and T1R3-comprising taste receptors are known to those of skill in the art (see, e.g. Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341: 544-546 (1989)).

A number of immunogens comprising portions of T1R protein or T1R3-comprising taste receptor may be used to produce antibodies specifically reactive with T1R protein. For example, recombinant T1R protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of 104 or greater are selected and tested for their cross reactivity against non-T1R or T1R3-comprising taste receptor proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better.

Antibodies specific only for a particular T1R3-comprising taste receptor ortholog, such as human T1R3-comprising taste receptor, can also be made, by subtracting out other cross-reacting orthologs from a species such as a non-human mammal. In addition, individual T1R proteins can be used to subtract out antibodies that bind both to the receptor and the individual T1R proteins. In this manner, antibodies that bind only to a particular receptor may be obtained.

Once the specific antibodies against T1R3-comprising taste receptors are available, the protein can be detected by a variety of immunoassay methods. In addition, the antibody can be used therapeutically as a T1R3-comprising taste receptor modulators. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunolozical Binding Assays

T1R3-comprising taste receptors can be detected and/or quantified using any of a number of well recognized immunological binding assays (see, e.g. U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the T1R3-comprising taste receptor or antigenic subsequence thereof). The antibody (e.g., anti-T1R3-comprising taste receptor) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled T1R3-comprising taste receptor or a labeled anti-T1R3-comprising taste receptor antibody. Alternatively, the labeling agent may be a third moiety, such a secondary antibody, that specifically binds to the antibody/T1R3-comprising taste receptor complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135: 2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting T1R3-comprising taste receptors in samples may be either competitive or noncompetitive.

Noncompetitive immunoassays are assays in which the amount of antigen is directly measured. In one preferred "sandwich" assay, for example, the anti-T1R3-comprising taste receptor antibodies can be bound directly to a solid substrate on which they are immobilized. These immobilized antibodies then capture T1R3-comprising taste receptors present in the test sample. T1R3-comprising taste receptors thus immobilized are then bound by a labeling agent, such as a second T1R3-comprising taste receptor antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of T1R3-comprising taste receptor present in the sample is measured indirectly by measuring the amount of a known, added (exogenous) T1R3-comprising taste receptor displaced (competed away) from an anti-T1R3-comprising taste receptor antibody by the unknown T1R3-comprising taste receptor present in a sample. In one competitive assay, a known amount of T1R3-comprising taste receptor is added to a sample and the sample is then contacted with an antibody that specifically binds to a T1R3-comprising taste receptor. The amount of exogenous T1R3-comprising taste receptor bound to the antibody is inversely proportional to the concentration of T1R3-comprising taste receptor present in the sample. In a particularly preferred embodiment, the antibody is immobilized on a solid substrate. The amount of T1R3-comprising taste receptor bound to the antibody may be determined either by measuring the amount of T1R3-comprising taste receptor present in a T1R3-comprising taste receptor/antibody complex, or alternatively by measuring the amount of remaining uncomplexed protein. The amount of T1R3-comprising taste receptor may be detected by providing a labeled T1R3-comprising taste receptor molecule.

A hapten inhibition assay is another preferred competitive assay. In this assay the known T1R3-comprising taste receptor is immobilized on a solid substrate. A known amount of anti-T1R3-comprising taste receptor antibody is added to the sample, and the sample is then contacted with the immobilized T1R3-comprising taste receptor. The amount of anti-T1R3-comprising taste receptor antibody bound to the known immobilized T1R3-comprising taste receptor is inversely proportional to the amount of T1R3-comprising taste receptor present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a T1R3-comprising taste receptor can be immobilized to a solid support. Proteins (e.g., T1R3-comprising taste receptors and homologs) are added to the assay that compete for binding of the antisera to the immobilized antigen. The ability of the added proteins to compete for binding of the antisera to the immobilized protein is compared to the ability of the T1R3-comprising taste receptor to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a T1R3-comprising taste receptor, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the T1R3-comprising taste receptor that is required to inhibit 50% of binding, then the second protein is said to specifically bind to the polyclonal antibodies generated to a T1R3-comprising taste receptor immunogen.

Other Assay Formats

Western blot (immunoblot) analysis is used to detect and quantify the presence of T1R3-comprising taste receptors in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind T1R3-comprising taste receptors. The anti-T1R3-comprising taste receptor antibodies specifically bind to the T1R3-comprising taste receptor on the solid support. These antibodies may be directly labeled or alternatively may be subsequently detected using labeled antibodies (e.g., labeled sheep anti-mouse antibodies) that specifically bind to the anti-T1R3-comprising taste receptor antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize T1R3-comprising taste receptors, or secondary antibodies that recognize anti-T1R3-comprising taste receptor.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Pharmaceutical Compositions and Administration

Pharmaceutically acceptable carriers are determined in part by the particular composition being administered (e.g., nucleic acid, oligonucleotide, amino acid, protein, peptide, small organic molecule, lipid, carbohydrate, mono-, di- or polysaccharide, particle, or transduced cell), as well as by the particular method used to administer the composition. Accordingly, there are a wide variety of suitable formulations of pharmaceutical compositions of the present invention (see, e.g. *Remington's Pharmaceutical Sciences,* 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of a T1R3-comprising taste receptor, the physician evaluates circulating plasma levels of the vector, vector toxicities, progression of the disease, and the production of anti-vector antibodies. In general, the dose equivalent of a naked nucleic acid from a vector is from about 1 μg to 100 μg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

Cellular Transfection and Gene Therapy

The present invention provides the nucleic acids of T1R3-comprising taste receptors for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a T1R3-comprising taste receptor of the present invention, by co-expressing two members of the T1R family, thereby mitigating the effects of absent, partial inactivation, or abnormal expression of a T1R3-comprising taste receptor. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, Biotechnology 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1: 13-26 (1994)).

REFERENCES

Adler, E., Hoon, M. A., Mueller, K. L., Chandrashekar, J., Ryba, N. J. P., and Zuker, C. S. (2000). A novel family of mammalian taste receptors. *Cell* 100, 693-702.

Bachmanov, A. A., Reed, D. R., Ninomiya, Y., Inoue, M., Tordoff, M. G., Price, R. A., and Beauchamp, G. K. (1997). Sucrose consumption in mice: major influence of two genetic loci affecting peripheral sensory responses. *Mamm. Genome* 8, 545-548.

Baker, E. K., Colley, N. J., and Zuker, C. S. (1994). The cyclophilin homolog NinaA functions as a chaperone, forming a stable complex in vivo with its protein target rhodopsin. *EMBO J.* 13, 4886-4895.

Boughter Jr., J. D., Pumplin, D. W., Yu, C., Christy, R. C., and Smith, D. V. (1997). Differential expression of alpha-gustducin in taste bud populations of the rat and hamster. *J. Neurosci.* 17, 2852-2858.

Brown, E. M., Gamba, G., Riccardi, D., Lombardi, M., Butters, R., Kifor, O., Sun, A., Hediger, M. A., Lytton, J., and Hebert, S. C. (1993). Cloning and characterization of an extracellular Ca (2+)-sensing receptor from bovine parathyroid. *Nature* 366, 575-580.

Capeless, C. G., and Whitney, G. (1995). The genetic basis of preference for sweet substances among inbred strains of mice: preference ratio phenotypes and the alleles of the Sac and DNA loci. *Chem. Senses* 20, 291-298.

Chandrashekar, J., Mueller, K. L., Hoon, M. A., Adler, E., Feng, L., Guo, W., Zuker, C. S., and Ryba, N. J. P. (2000). T2Rs function as bitter taste receptors. *Cell* 100, 703-11.

Danilova, V., Hellekant, G., Tinti, J.-M., and Nofre, C. (1998). Gustatory Responses of the Hamster *Mesocricetus auratus* to Various Compounds Considered Sweet by Humans. *J. Neurophysiol.* 80, 2102-2112.

Dwyer, N. D., Troemel, E. R., Sengupta, P., and Bargmann, C. I. (1998). Odorant receptor localization to olfactory cilia is mediated by ODR-4, a novel membrane-associated protein. *Cell* 93, 455-466.

Fuller, J. L. (1974). Single-locus control of saccharin preference in mice. *J. Hered.* 65, 33-36.

Herrada, G., and Dulac, C. (1997). A novel family of putative pheromone receptors in mammals with a topographically organized and sexually dimorphic distribution. *Cell* 90, 763-773.

Hoon, M. A., Adler, E., Lindemeier, J., Battey, J. F., Ryba, N. J. P., and Zuker, C. S. (1999). Putative mammalian taste receptors: a class of taste-specific GPCRs with distinct topographic selectivity. *Cell* 96, 541-551.

Kaupmann, K., Huggel, K., Heid, J., Flor, P. J., Bischoff, S., Mickel, S. J., McMaster, G., Angst, C., Bittiger, H., Froestl, W., and Bettler, B. (1997). Expression cloning of GABA(B) receptors uncovers similarity to metabotropic glutamate receptors. *Nature* 386, 239-246.

Kitagawa, M., Kusakabe, Y., Miura, H., Ninomiya, Y., and Hino, A. (2001). Molecular genetic identification of a candidate receptor gene for sweet taste. *Biochem. Biophys. Res. Commun.* 283, 236-242.

Krautwurst, D., Yau, K. W., and Reed, R. R. (1998). Identification of ligands for olfactory receptors by functional expression of a receptor library. *Cell* 95, 917-926.

Lefkowitz, R. J., Inglese, J., Koch, W. J., Pitcher, J., Attramadal, H., and Caron, M. G. (1992). G-protein-coupled receptors: regulatory role of receptor kinases and arrestin proteins. *Cold Spring Harb. Symp. Quant. Biol.* 57, 127-133.

Li, X., Inoue, M., Reed, D. R., Huque, T., Puchalski, R. B., Tordoff, M. G., Ninomiya, Y., Beauchamp, G. K., and Bachmanov, A. A. (2001). High-resolution genetic mapping of the saccharin preference locus (Sac) and the putative sweet taste receptor (T1R1) gene (Gpr70) to mouse distal Chromosome 4. *Mamm. Genome* 12, 13-16.

Lindemann, B. (1996). Taste reception. *Physiol. Rev.* 76, 718-766.

Lush, I. E. (1989). The genetics of tasting in mice. VI. Saccharin, acesulfame, dulcin and sucrose. *Genet. Res.* 53, 95-99.

Matsunami, H., and Buck, L. B. (1997). A multigene family encoding a diverse array of putative pheromone receptors in mammals. *Cell* 90, 775-784.

Matsunami, H., Montmayeur, J. P., and Buck, L. B. (2000). A family of candidate taste receptors in human and mouse. *Nature* 404, 601-604.

Max, M., Shanker, Y. G., Huang, L., Rong, M., Liu, Z., Campagne, F., Weinstein, H., Damak, S., and Margolskee, R. F. (2001). Tas1r3, encoding a new candidate taste receptor, is allelic to the sweet responsiveness locus Sac. *Nat. Genet.* 28, 58-63.

McBurney, D. H., and Gent, J. F. (1979). On the nature of taste qualities. *Psychol. Bull.* 86, 151-167.

Mistretta, C. M., and Hill, D. L. (1995). Development of the taste system. Basic neurobiology. In *Handbook of olfaction and gustation*, R. L. Doty, ed. (New York: Marcel Dekker), pp. 635-668.

Mody, S. M., Ho, M. K., Joshi, S. A., and Wong, Y. H. (2000). Incorporation of Galpha(z)-specific sequence at the carboxyl terminus increases the promiscuity of galpha(16) toward G(i)-coupled receptors. *Mol. Pharmacol.* 57, 13-23.

Montmayeur, J. P., Liberles, S. D., Matsunami, H., and Buck, L. B. (2001). A candidate taste receptor gene near a sweet taste locus. Nat. Neurosci. 4, 492-498.

Nagarajan, S., Kellogg, M. S., DuBois, G. E., and Hellekant, G. (1996). Understanding the mechanism of sweet taste: synthesis of ultrapotent guanidinoacetic acid photoaffinity labeling reagents. *J. Med. Chem.* 39, 4167-4172.

Nakanishi, S. (1992). Molecular diversity of glutamate receptors and implications for brain function. *Science* 258, 597-603.

Ninomiya, Y., Inoue, M., Imoto, T., and Nakashima, K. (1997). Lack of gurmarin sensitivity of sweet taste receptors innervated by the glossopharyngeal nerve in C57BL mice. *Am. J. Physiol.* 272, R1002-R1006.

Ninomiya, Y., Mizukoshi, T., Higashi, T., Katsukawa, H., and Funakoshi, M. (1984). Gustatory neural responses in three different strains of mice. *Brain Res.* 302, 305-314.

Offermanns, S., and Simon, M. I. (1995). G alpha 15 and G alpha 16 couple a wide variety of receptors to phospholipase C. *J. Biol. Chem.* 270, 15175-80.

Ryba, N. J. P., and Tirindelli, R. (1997). A new multigene family of putative pheromone receptors. *Neuron* 19, 371-379.

Sainz, E., Korley, J. N., Battey, J. F., and Sullivan, S. L. (2001). Identification of a novel member of the T1R family of putative taste receptors. *J. Neurochem.* 77, 896-903.

Salahpour, A., Angers, S., and Bouvier, M. (2000). Functional significance of oligomerization of G-protein-coupled receptors. *Trends Endocrinol. Metab.* 11, 163-168.

Schiffman, S. S., Cahn, H., and Lindley, M. G. (1981). Multiple receptor sites mediate sweetness: evidence from cross adaptation. *Pharmacol. Biochem. Behav.* 15, 377-388.

Scott, K., Brady, R., Jr., Cravchik, A., Morozov, P., Rzhetsky, A., Zuker, C., and Axel, R. (2001). A chemosensory gene family encoding candidate gustatory and olfactory receptors in *Drosophila*. *Cell* 104, 661-673.

Smith, D. V., and Frank, M. E. (1993). Sensory coding by peripheral taste fibers. *In Mechanisms of Taste Transduction*, S. A. Simon and S. D. Roper, eds. (Boca Raton: CRC Press), pp. 295-338.

Troemel, E. R., Chou, J. H., Dwyer, N. D., Colbert, H. A., and Bargmann, C. I. (1995). Divergent seven transmembrane receptors are candidate chemosensory receptors in *C. elegans*. *Cell* 83, 207-218.

Tsien, R. Y., Rink, T. J., and Poenie, M. (1985). Measurement of cytosolic free Ca2+ in individual small cells using fluorescence microscopy with dual excitation wavelengths. *Cell Calcium* 6, 145-157.

EXAMPLES

The following examples are offered to illustrate, but not to limit the claimed invention.

Example 1

Results

Generation of T1R1, T1R2 and T1R3 KO Mice

Expression of T1R receptors defines three largely non-overlapping populations of taste cells in the tongue and palate: cells co-expressing T1R1 and T1R3 (T1R1+3), cells co-expressing T1R2 and T1R3 (T1R2+3), and cells expressing T1R3 alone (Nelson, G. et al., *Cell*, 106, 381-390 (2001)). Heterologous expression studies of T1Rs in HEK cells demonstrated that T1R1 and T1R3 combine to form a broadly tuned L-amino acid receptor, while co-expression of T1R2 and T1R3 generates a sweet taste receptor that responds to all classes of sweet-tasting compounds (Nelson, G. et al., *Cell*, 106, 381-390 (2001); Nelson, G. et al., *Nature*, 416, 199-202 (2002); Li, X. et al., *Proc Natl Acad Sci USA*, 99, 4692-4696 (2002)). If T1R3 functions in vivo as a common component of the sweet and amino acid taste receptors, then a knockout of this GPCR should generate mice devoid of sweet and amino acid taste reception. In contrast, knockout of T1R1 or T1R2 might be expected to selectively affect a single taste modality.

To define the role of T1Rs in vivo, we generated knockout mice that lack each of the T1Rs by deleting exons encoding domains essential for receptor function. FIG. 1 illustrates the KO strategies and shows in situ hybridization experiments demonstrating a complete lack of specific T1R staining in the corresponding homozygous KO animals. In order to ensure that loss of any one T1R did not affect the viability or integrity of taste cells, we also compared the expression of other T1Rs, T2Rs, PLCb2 (Rossler, P. et al., *Eur J Cell Biol*, 77, 253-261 (1998); Zhang, Y. et al., *Cell*, 112, 293-301 (2003)) and TRPM5 (Perez, C. A. et al., *Nat Neurosci*, 5, 1169-1176 (2002); Zhang, Y. et al., *Cell*, 112, 293-301 (2003)) in control and KO animals. No significant differences were observed in the number or distribution of T1R-, T2R, PLCb2 and TRPM5-positive cells between wild type and KO taste tissue (FIG. 1 and data not shown).

Two complementary strategies were used to assay the taste responses of the genetically modified mice. First, we recorded tastant-induced action potentials from one of the major nerves innervating taste receptor cells of the tongue (chorda tympani). This physiological assay monitors the activity of the taste system at the periphery, and provides a measure of taste receptor cell function. Second, we examined taste behavior by measuring taste-choices in standard long-term two-bottle intake preference assays, or by direct counting of immediate licking responses in a multi-channel gustometer (Glendinning, J. I. et al., *Chem Senses*, 27, 461-474 (2002); Zhang, Y. et al., *Cell*, 112, 293-301 (2003); see Experimental Procedures). This second method relies on very short exposures to tastants (5 s events over a total of 30 min versus 48 hrs for two-bottle preference assays), and therefore has the great advantage of minimizing the impact of other sensory inputs, and post-ingestive and learning effects from the assay.

FIG. 2 shows that knockouts of T1Rs have no significant effect either on physiological or behavioral responses to citric acid, sodium chloride, and a variety of bitter tastants. These results demonstrate that bitter, salty and sour taste reception and perception operate through pathways independent of T1R receptors, and further substantiate a model of coding at the periphery in which individual modalities operate independently of each other.

T1R1+3 is the Umami Receptor

Previously, Chaudhari et al described a truncated variant of the metabotropic glutamate receptor-4 (mGluR4t) and suggested that it functions as the umami taste receptor (Chaudhari, N. et al., *Nat Neurosci*, 3, 113-119 (2000)). We find this proposal unsatisfactory for many reasons. (1) The mGluR4t variant is missing the mGluR4 signal sequence needed for surface targeting. (2) This putative receptor also lacks large fractions of the domains essential for glutamate recognition as revealed by the crystal structure of the glutamate binding domain of mGluR (Kunishima, N., et al., *Nature*, 407, 971-977 (2000)). (3) mGluR4t umami signaling has been proposed to operate via a cAMP pathway (Abaffy, T. et al., *Am J Physiol Cell Physiol*, 284, C1420-1428 (2003); Chaudhari, N. et al., *Nat Neurosci*, 3, 113-119 (2000)). However, amino acid/umami taste is a PLCβ2/TRPM5-dependent process (Zhang, Y. et al., *Cell*, 112, 293-301 (2003)). (4) Umami taste, but not mGluR4 activity, is strongly affected by the umami enhancers IMP and GMP. (5) Finally, mGluR4 KO animals retain responses to umami stimuli (Chaudhari, N., and Roper, S. D., *Ann N Y Acad Sci*, 855, 398-406 (1998)). In contrast, recent evidence suggest that the T1R1+3 amino acid receptor may function as the mammalian umami (glutamate) taste sensor: First, the human and rodent T1R1+3 receptors display selectivity and sensitivity differences that mimic amino acid taste differences between rodents and humans (Nelson, G. et al., *Nature*, 416, 199-202 (2002); Yoshii et al., 1986). Second, T1R1+3 activity is reliably enhanced by IMP and GMP, the two best known potentiators of umami taste in vivo (Nelson, G. et al., *Nature*, 416, 199-202 (2002); Li, X. et al., *Proc Natl Acad Sci USA*, 99, 4692-4696 (2002)). Thirdly, T1R1+3 is activated by psychophysically relevant concentrations of the umami agonists L-Asp and L-AP4 (Nelson, G. et al., *Nature*, 416, 199-202 (2002); Li, X. et al., *Proc Natl Acad Sci USA*, 99, 4692-4696 (2002)). In order to rigorously assess the role of T1R1+3 in umami taste, we examined T1R1 and T1R3 KO animals (see FIG. 1).

Figures 3E, 3F:
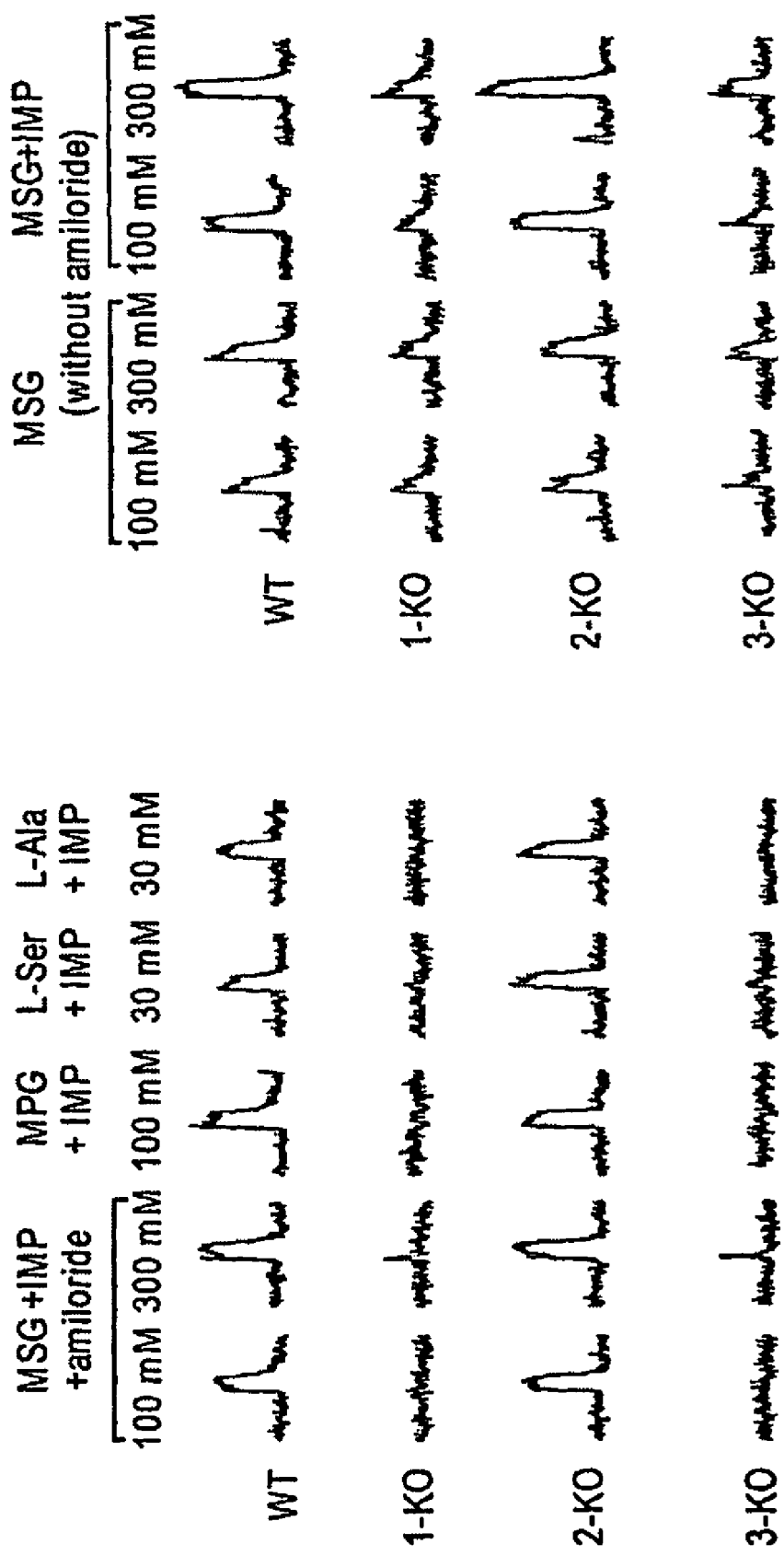
Figure 4A:
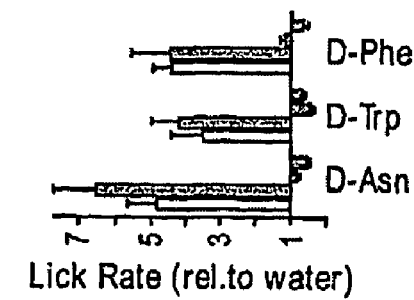
Figure 4A:
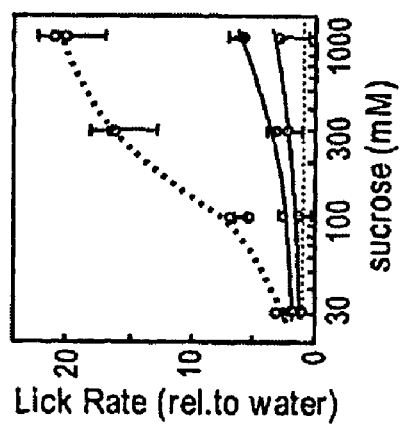
Figure 4A:
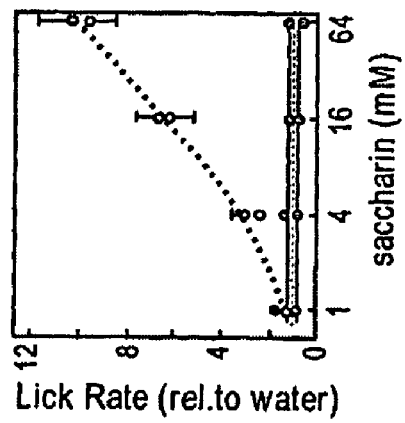
Figure 4A:
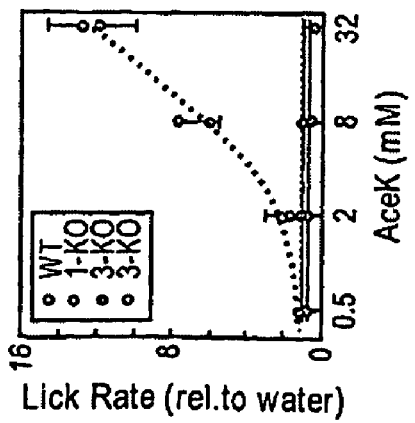
Figure 4B:
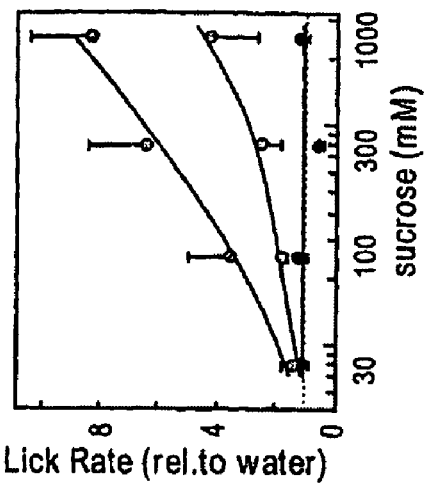
Figure 4B:
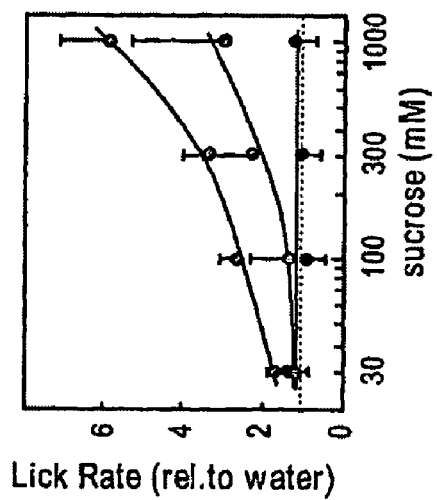
Figure 4B:
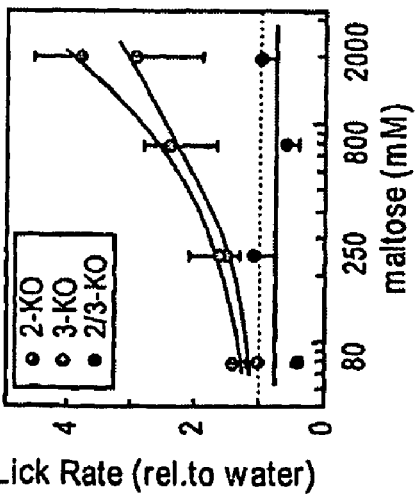

Because of its Na+ content, monosodium glutamate (MSG) evokes both salty and umami taste. We therefore assayed umami responses using several strategies that allowed us to isolate salt taste from that of glutamate in behavioral and electrophysiological studies. These included testing MSG in the presence of the sodium channel blocker amiloride, using MPG, the potassium salt of glutamate, and testing the umami agonists AP4 and aspartic acid, all in the presence or absence of the umami enhancer IMP. FIG. 3 shows that when salt effects are minimized, T1R3 KO mice have a dramatic loss of behavioral attraction—and a profound corresponding deficit in physiological responses to all umami tastants—including glutamate, aspartate, glutamate plus IMP, and IMP alone. Very recently, Damak et al independently generated T1R3 KO animals but concluded that multiple umami receptors must exist as significant MSG responses remained in their studies of KO mice (Damak, S. et al., *Science*, 301, 850-853 (2003)). Notably, the MSG responses of the KO animals were strictly independent of IMP, a contradiction given that IMP enhancement is the hallmark of the umami modality. Since salt effects were not accounted for, we suspect that much of their remaining responses reflect Na+ content in MSG rather than umami taste (compare responses to MSG+IMP versus MPG+IMP or MSG+IMP+amiloride in FIG. 3*e-f*).

If T1R1 combines with T1R3 (T1R1+3) to generate the mammalian umami receptor, then a knockout of T1R1 should also eliminate all umami responses. FIG. 3 demonstrates that this is absolutely the case. In contrast, these very same tastants elicit normal, robust responses in control and in T1R2 KO animals. Together, these results prove that T1R1+3 is the mammalian umami receptor.

Previously, we showed that in addition to typical umami tastants, the mouse T1R1+3 receptor is also activated by other L-amino amino acids, and in the presence of IMP functions as a broadly tuned L-amino acid sensor (Nelson, G. et al., *Nature*, 416, 199-202 (2002)). Therefore, we tested responses of T1R1 and T1R3 KO animals to L-amino acids in the presence or absence of IMP. Indeed, responses to amino acid tastants are severely defective in T1R1 and T1R3, but not T1R2 KO strains (FIG. 3), firmly establishing the T1R1+3 heteromeric GPCR complex as the taste receptor for a wide range of L-amino acids and IMP. Interestingly, when we assayed exceedingly high concentrations of L-amino acids that taste sweet to humans (e.g. >300 mM Ala, Ser, and Thr), T1R1 KO animals, but not T1R3 KO mice retained a small residual attraction (see panel d in FIG. 3); these trace behavioral responses likely reflect the activation of the T1R2+3 sweet taste receptor (Nelson, G. et al., *Cell*, 106, 381-390 (2001); see below).

T1R2+3 and T1R3 are Required for Sweet Reception and Perception

T1R2+3 functions in cell based assays as a heteromeric receptor for diverse chemical classes of sweet compounds including natural sugars, artificial sweeteners, D amino acids and sweet-tasting proteins (Nelson, G. et al., *Cell*, 106, 381-390 (2001); Li, X. et al., *Proc Natl Acad Sci USA*, 99, 4692-4696 (2002)). However, a number of studies have suggested that animals may express distinct types of sweet receptors (Schiffman, S. S. et al., *Pharmacol Biochem Behav*, 15, 377-388 (1981); Ninomiya, Y. et al., *J Neurophysiol*, 81, 3087-3091 (1999)). To define the role of T1R2+3 in vivo, we examined sweet responses of knockout mice that lack functional T1R2 and T1R3 proteins. FIGS. 4 and 5 demonstrate that responses to all classes of sweet tastants are dramatically impaired in T1R2 and T1R3 knockout strains. We tested a broad panel of sugars, artificial sweeteners and D-amino acids, and in all cases responses were severely defective: behavioral attraction is nearly abolished and nerve responses are greatly diminished. These results confirm T1R2+3 as the principal sweet taste sensor in vivo.

Notably, very high concentrations (>300 mM) of natural sugars, but not of artificial sweeteners or D-amino acids, elicited modest but detectable attractive responses in both T1R2 and T1R3 knockout strains. Thus, either there are additional sweet taste receptors (i.e. T1R-independent pathways), or T1R2 and T1R3 may also function on their own as low affinity receptors for natural sugars in the absence of their heteromeric partners. If the remaining responses are in fact due to T1R2 or T1R3, then a double knockout of these GPCRs should eliminate all sweet responses. Since T1R2 and T1R3 loci are linked at the distal end of chromosome 4 (Nelson, G. et al., *Cell*, 106, 381-390 (2001)), we first generated recombinant T1R2 KO, T1R3 KO mice and then tested them physiologically and behaviorally. FIGS. 4 and 5 (red traces) show that T1R2, T1R3 double KO mice have lost all responses to high concentration of sugars. Together, these results illustrate the in vivo significance of the combinatorial assembly of T1Rs, and demonstrate that all sweet taste reception operates via the T1R2 and T1R3 GPCRs.

Do T1R2 or T1R3 homodimeric receptors play a significant role in sweet sensing in wild type mice? T1R2 is always expressed in cells containing T1R3 (T1R2+3 cells; Nelson, G. et al., *Cell*, 106, 381-390 (2001)). Therefore, even if some T1R2 were not associated with T1R3 in these cells, the much higher affinity of the T1R2+3 heteromeric receptor for sweet tastants would likely dominate the cellular response. In contrast, we previously reported that T1R3 is also found in a significant fraction of cells of the tongue and palate epithelium independent of T1R1 and T1R2 (T1R3 alone cells; Nelson, G. et al., *Cell*, 106, 381-390 (2001)). This class of cells may provide animals with additional means of detecting and responding to high concentrations of sugars. To demonstrate that T1R3 alone can function as a low affinity receptor for natural sugars, we generated HEK cells stably expressing T1R3 and an optimized G protein chimera engineered to couple to T1Rs (see Experimental Procedures). FIG. 6 shows that T1R3 alone in fact responds to very high concentrations of natural sugars, but not to lower concentrations (<300 mM), or to artificial sweeteners. These results confirm T1R3 as a low affinity sugar receptor, and support the postulate that T1R3 alone cells function in vivo as additional sweet sensors (Nelson, G. et al., Cell, 106, 381-390 (2001)). This partial cellular segregation of sensing natural and artificial sweeteners may help explain why artificial sweeteners never attain the level of sweetness afforded by high concentrations of natural sugars (i.e. activation of T1R2+3 cells versus T 1R2+3 and T1R3 alone cells).

T1R2 Delimits Species-Specific Sweet Taste Preferences

Humans can taste a number of natural and artificial sweeteners that rodents cannot. For example, monellin, thaumatin, aspartame and neohesperidin dihydrochalcone taste sweet to humans at sub-millimolar concentrations, whereas rodents show no preference even at 100 times higher concentrations (Danilova, V. et al., *J Neurophysiol*, 80, 2102-2112 (1998)). Previously, we reported that rodent and human T1Rs are more than 30% dissimilar in their amino acid sequences, and hypothesized that such differences underlie the species-specific selectivity in sweet taste detection (Nelson, G. et al., Cell, 106, 381-390 (2001); Nelson, G. et al., *Nature*, 416, 199-202 (2002)). Because T1R2 participates exclusively in sweet taste detection while T1R3 is involved in both sweet and amino acid recognition, we reasoned that T1R2 would be a particularly critical determinant of sweet taste selectivity in vivo. Therefore, we predicted that introducing the human T1R2 gene in T1R2 KO mice should both rescue and "humanize" sweet responses.

We generated mice that were homozygous for the T1R2 KO allele, but instead expressed a human T1R2 transgene in the native "T1R2-cells". A 12 kb genomic clone containing the T1R2 regulatory sequences was fused to a hT1R2 full length cDNA and introduced into T1R2 KO mice. Multiple independent lines were assayed for their selectivity and sensitivity to sweet tastants. To examine expression of hT1R2, we performed two-color fluorescent in situ hybridization experiments in transgenic animals carrying the wild type mT1R2 allele. FIG. 7 (panel a-d) demonstrate that human T1R2 is selectively expressed in T1R2-expressing cells, and effectively restores sweet taste function. More importantly, the human transgene now confers these mice with the ability to detect and respond to several compounds that taste sweet to humans, but are not normally attractive to rodents; these include aspartame, glycyrrhizic acid and the sweet proteins thaumatin and monellin. Interestingly, the humanized T1R2 mice still do not respond to the intensely sweet compound neohesperidin dihydrochalcone, nor do HEK cells transfected with the human T1R2 and mouse T1R3 GPCRs. However, when cells are transfected with human T1R2 and human T1R3 they robustly respond to neohesperidin dihydrochalcone. Taken together, these experiments validate T1Rs as key determinants of differences in sweet taste selectivity and specificity between rodents and humans, and further substantiate T1R2+3, and T1R2-expressing cells, as an principal mediator of sweet taste in vivo. Finally, we propose that polymorphisms in both T1R2 and T1R3 are important determinants of human individual sweet taste preferences.

T1R2-Expressing Cells Encode Behavioral Attraction In Vivo

Activation of taste receptors trigger distinct behavioral responses in animals. For example, excitation of the T1R2+3 receptor stimulates behavioral attraction to sugars and sweet-tasting compounds in mice. Is this response a property of the receptors or the cells in which they are expressed? One way to answer this question would be to express a novel receptor unrelated to the taste system in the T1R2+3 cells and examine whether its selective stimulation elicits attractive responses (Troemel, E. R. et al., *Cell* 91, 161-169 (1997)).

Our approach was to target expression of a GPCR that could couple to the endogenous signaling pathways in T1R2+3 cells, but could only be activated by a nonnatural ligand. In order to examine taste responses in the very same animals before and after receptor expression we utilized an inducible system. To accomplish this, we used transgenic mice in which a modified k-opioid receptor activated solely by a synthetic ligand (RASSL; Redfern, C. H. et al., *Nat Biotechnol*, 17, 165-169 (1999)) was targeted to the T1R2-expressing cells under the control of the Tet-on inducible system (see Experimental Procedures).

Figure 7A:
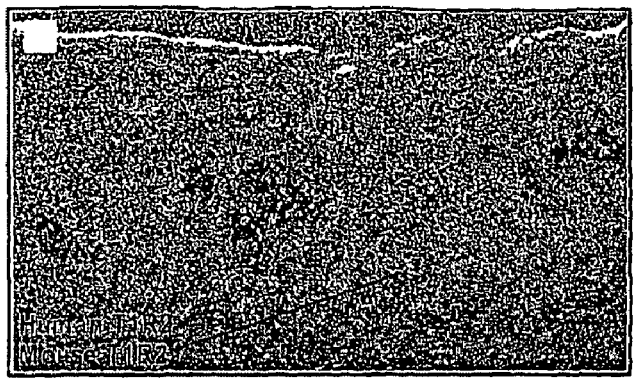
Figure 7B:
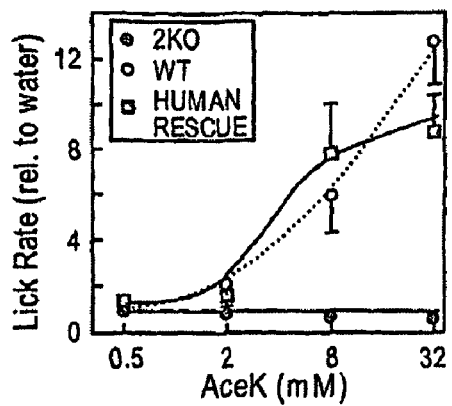
Figure 7C:
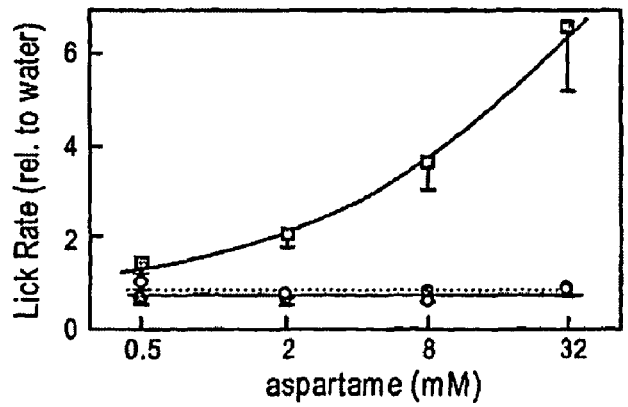
Figure 7D:
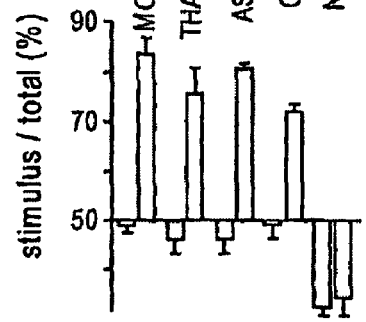
Figure 7E:
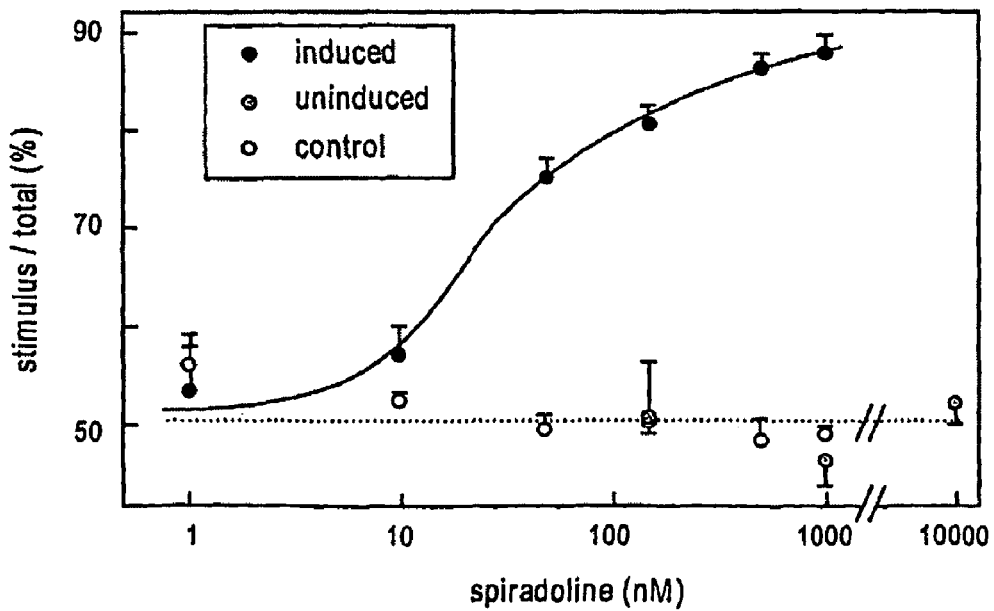

FIG. 7e shows that un-induced animals, or wild type controls treated with doxycycline, are completely insensitive to the k-opioid agonist spiradoline. Remarkably, induction of RASSL expression in the T1R2-cells generates animals that are now strongly attracted to nanomolar concentrations of spiradoline (FIG. 7, red trace). Thus, we conclude that activation of T1R2-expressing cells, rather than the receptors they express, determines behavioral attraction in mice. Furthermore, these results unequivocally show that activating a single cell type is sufficient to trigger specific taste responses; therefore a model requiring a combinatorial pattern of activity, or temporal coding, is not needed to account for attraction mediated by T1R2-expressing cells. By extension we suggest that activation of these taste signaling pathways in human T1R2+3 cells, regardless of the nature of the receptor, would evoke sweet taste.

Multiple receptors have been proposed to mediate sweet and umami taste in mammals. Notably, even within each of these two modalities several GPCRs, ion channels, and models invoking intracellular targets directly activated by cell-permeable tastants have been postulated (Kinnamon, S. C. *Neuron*, 25, 507-510 (2000); Margolskee, R. F., *J Biol Chem*, 277, 1-4 (2002)). We have used a combination of cell-based assays, genetic, physiological and behavioral approaches to prove that the receptors for sweet and umami taste in mammals are the T1Rs: umami taste is mediated by the T1R1+3 heteromeric GPCR, and sweet by the two T1R-based receptors, T1R2 and T1R3 (T1R2+3, and most likely, a homodimer of T1R3). Therefore, sweet and amino acid taste (umami)- two chemosensory inputs that trigger behavioral attraction, share a common receptor repertoire and evolutionary origin.

The human T1R1+3 receptor is activated by glutamate and aspartate far more effectively than by other amino acids (Li, X. et al., *Proc Natl Acad Sci USA*, 99, 4692-4696 (2002)). In contrast, the mouse T1R1+3 receptor recognizes a much broader range of L-amino acids, both in cell based assays (Nelson, G. et al., *Nature*, 416, 199-202 (2002)) and in vivo (this paper). If the evolutionary role of the T1R1+3 receptor was to mediate attractive responses to protein-rich foods, one may question whether the tuning of receptor selectivity in primates to just two amino acids substantially altered the ability to detect diets rich these nutrients. Since amino acids are usually found as complex mixtures, detecting any one should generally be adequate, and thus this "narrowing" of tastant selectivity should not have had a significant dietary impact. Given that the same cells and receptors recognize glutamate, other amino acids and IMP, we suggest that in rodents the umami taste modality must be generalized to include most L-amino acids and the very concept of a distinct glutamate taste in rodents (Chaudhari, N. et al., *Nat Neurosci*, 3, 113-119 (2000); Lin, W. et al., *J Neurophysiol*, 89, 1434-1439 (2003)) needs to be re-evaluated.

A spoonful of sugar or a few tablets of artificial sweetener? Our day to day experiences tell us that natural and artificial sweeteners do not taste the same. In this manuscript we showed that T1R2 and T1R3 are responsible for all sweet sensing. How do they account for the perceived taste differences between sweet tastants? Many sweeteners are likely to activate receptors for other taste modalities, like T2R bitter sensing cells accounting for the bitter aftertaste of saccharin (data not shown). Therefore, the "taste" of even a single sweet molecular species may reflect the combined activity of cells tuned to different taste modalities, and not just the activity of sweet sensing cells. We have also shown that at higher, but still physiologically relevant concentrations of sugars (>300 mM), natural and artificial sweeteners activate partially overlapping, yet distinct sweet receptor types (T1R2+3 and T1R3 alone).

We have shown that T1Rs are the mediators of the two principal attractive taste modalities, and demonstrated that mice expressing a RASSL opioid receptor became powerfully attracted to spiradoline, a normally tasteless and nutriionally irrelevant compound, proving that to taste is to believe. The discovery and functional characterization of the cells and receptors for bitter, sweet, and umami taste now provide a compelling view of how taste is encoded at the periphery: dedicated taste receptor cells mediate attractive and aversive behaviors (see, e.g., Zhang, Y. et al., *Cell*, 112, 293-301 (2003)).

Experimental Procedures

Gene Targeting of T1R1, T1R2 and T1R3

The strategy used to create T1R knockout animals is shown in FIG. 1. For T1R1, exon 6 encoding the predicted seven transmembrane domain of the receptor was replaced by the PGK-neo$^r$ cassette. Homologous recombination in R1 ES cells was detected by diagnostic Southern hybridization with probes outside the targeting construct. Two targeted ES clones were injected into C57BL/6 blastocysts. Chimeric mice were bred with C57BL/6 mice and progeny backcrossed to C57BL/6 mice for two generations prior to establishing a homozygous knockout colony.

For T1R2, a similar approach deleted exons 5 and 6 (see FIG. 1). Chimeric animals were bred with C57BL/6 mice and progeny backcrossed to C57BL/6 mice for four generations. The T1R3 taster (C57) and non-taster (129) alleles (Nelson, G. et al., *Cell*, 106, 381-390 (2001)) were identified based on an EcoRI polymorphism ~12 kb upstream of the starting ATG of T1R3. All of the T1R2 knockout animals used in this study carried a taster allele of T1R3. However, studies with T1R2 KO mice homozygous for the non-taster T1R3 allele produced qualitatively similar results (data not shown). To generate T1R3 KO knockout animals, we replaced exons 1 to 5 encoding the N-terminal extracellular domain with the PGK-neor cassette (see FIG. 1). Chimeric mice were bred with C57BL/6 mice and progeny backcrossed to C57BL/6 mice for two generations.

T1R knockouts have normal viability, body weight, overall anatomy and general behavior. Similarly, taste receptor cells appear normal morphologically and numerically in all knockout backgrounds.

In Situ Hybridization

Fresh frozen sections (16 μm/section) were attached to silanized slides and prepared for in situ hybridization or immunohistochemistry as previously described (Hoon, M. A. et al., *Cell.*, 96, 541-551 (1999)). Single label in situ hybridization was carried out using digoxigenin labeled probes; T1R1 and T1R2 probes were to the predicted transmembrane domains, while T1R3 and RASSL (Redfem, C. H. et al., *Nat Biotechnol*, 17, 165-169 (1999)) probes utilized the full coding sequences. Double-label fluorescent detection used fluorescein (full-length hT1R2) and digoxigenin (full-length mT1R2) probes at high stringency (hybridization, 5×SSC, 50% formamide, 65-72° C.; washing, 0.2×SSC, 72° C.). Hybridization was detected with distinct fluorescent substrates (Adler, E. et al., *Cell*, 100, 693-702 (2000)) and specificity of labeling was checked using T1R2-knockout and non transgenic controls.

Generation of Transgenic Mice Expressing Human T1R2 and RASSL

An approx. 12 kb genomic fragment upstream of mouse T1R2 was fused to a human T R2 cDNA and to a reverse-tetracycline dependent transactivator (rtTA) construct (Gossen, M. et al., *Curr Opin Biotechnol*, 5, 516-520 (1994)). Transgenic lines were produced by pronuclear injection of zygotes from FVB/N mice. Three independent human T1R2 transgenic lines displayed behavioral attraction to aspartame (10 mM). One line was crossed into the T1R2 knockout background, and assayed for taste responses and transgene expression. No expression outside T1R2-cells was detected. T1R2-rtTA transgenic lines were crossed with tetO-Rol/tetO-lacZ transgenic animals (Redfem, C. H. et al., *Nat Biotechnol*, 17, 165-169 (1999)). Doubleheterozygous progeny were induced by doxycycline treatment (6 gm/kg) (Bio-Serv) for 3 days (Gogos, J. A. et al., *Cell*, 103, 609-620 (2000)) and examined for β-galactosidase activity (Zack, D. J. et al., *Neuron* 6, 187-199 (1991)) and RASSL expression in the tongue and palate. A line displaying appropriate β-galactosidase staining and RASSL expression pattern was selected for behavioral assays.

Behavioral Assays

Taste behavior was assayed using a short term assay that directly measures taste preferences by counting immediate licking responses in a multi-channel gustometer (Davis MS160-Mouse gustometer; DiLog Instruments, Tallahassee, Fla.). Mice were trained and tested as described previously (Zhang, Y. et al., *Cell*, 112, 293-301 (2003)). Individual mice were placed in the gustometer for 30 minutes, and stimuli were presented in random order for 5s trials that were initiated by the mouse licking the stimulus spout. For sodium saccharin, glutamate and aspartate, 100 μM amiloride was added to all solutions (including the control) to minimize effects of salt taste. Data points represent the mean rate that mice licked a tastant relative to their sampling of an appropriate control tastant (ratio defined as lick rate relative to control); lick suppression is defined as 1 minus the lick rate relative to control. In most cases the control tastant was water but for amino acids+1 mM IMP, 200 mM MSG and 10 mM IMP the controls were 1 mM IMP, 200 mM sodium gluconate and 10 mM CMP, respectively.

Standard two-bottle preference assays were carried out as described previously (Nelson, G. et al., *Cell*, 106, 381-390 (2001)). For mice carrying T1R2-rtTA and tetO-Rol/tetO-lacZ transgenes, expression was induced by doxycycline treatment 3 days prior to, and during the behavioral testing. Controls included testing the same mice without induction as well as mice carrying just the T1R2-rtTA transgene treated with doxycycline. All three groups displayed normal responses to sucrose.

We noted that in 2-bottle assays T1R-KO animals appear to "learn" to identify solutions containing very high concentrations of natural sugars (>500 mM); successive exposure resulted in decreased detection threshold and increased preference ratios. Because mice are repeatedly exposed to test compounds for 48 hrs in standard twobottle assays, they may use other sensory inputs like texture or smell to distinguish tastant from water. If not properly controlled, this could be easily misunderstood as behavioral attraction via taste pathways. To avoid this problem, we used either short term immediate lick response assays (see above) or two-bottle assays with naive knockout mice (i.e. never exposed to such tastants during either training or testing).

Nerve Recordings

Lingual stimulation and recording procedures were performed as previously described (Dahl, M. et al., *Brain Res*, 756, 22-34 (1997); Nelson, G. et al., *Nature*, 416, 199-202 (2002)). Neural signals were amplified (5,000×) with a Grass P511 AC amplifier (Astro-Med), digitized with a Digidata 1200B A/D converter (Axon Instruments), and integrated (r.m.s. voltage) with a time constant of 0.5 s. Taste stimuli were presented at a constant flow rate of 4 ml min$^{-1}$ for 20 s intervals interspersed by 2 min rinses with artificial saliva (Danilova, V., and Hellekant, G., *BMC Neurosci*, 4, 5. (2003)) between presentations. All data analyses used the integrated response over a 25 s period immediately after the application of the stimulus. Each experimental series consisted of the application of 6 tastants bracketed by presentations of 0.1 M citric acid to ensure the stability of the recording. The mean response to 0.1 M citric acid was used to normalize responses to each experimental series.

Tastants used for nerve recordings (maximal concentrations) were: sucrose, glucose, maltose (600 mM); sodium saccharin (40 mM); AceK (60 mM); Citric Acid (100 mM); NaCl (100 mM); NH$_4$Cl (100 mM); 6-n-propyl thiouracil (10 mM), quinine (10 mM); cycloheximide (1 mM); L-Ser, L-Ala, (30 mM with 0.5 mM IMP added) MSG and MPG (300 mM with or without 0.5 mM IMP); D-Ala, D-Phe, and D-Trp (100 mM). Amiloride (50 uM) was added to reduce sodium responses as indicated in the figure legends.

Heterologous Expression of T1R5 and Calcium Imaging

Modified HEK-293 cells (PEAK$^{rapid}$ cells; Edge BioSystems, MD) were grown, transfected with T1Rs and promiscuous G-proteins and assayed for functional responses to tastants by Ca-imaging essentially as described previously (Nelson, G. et al., *Cell*, 106, 381-390 (2001)). Minor differences in FURA-2 loading and Ca-imaging included using 199(H) Medium (Biosource) containing 0.1% BSA, 100 µM EGTA and 200 µM CaCl$_2$ as assay buffer as well as reducing the time allowed for FURA-AM ester cleavage to 10 minutes. The imaging system was an Olympus IX50 microscope equipped with a 10×/0.5 N.A. fluor objective (Zeiss), the TILL imaging system (TILL Photonics GmbH), and a cooled CCD camera. Acquisition and analysis of fluorescence images used TILL-Vision software.

To optimize coupling of T1R-responses to changes in [Ca$^{2+}$]$_i$, C-terminal residues of human Gα16 (Offermanns, S., and Simon, M. I., *J Biol Chem*, 270, 15175-15180 (1995)) were replaced with the corresponding residues from Gz (Mody, S. M. et al., *Mol Pharmacol*, 57, 13-23 (2000)), gustducin (McLaughlin, S. K. et al., *Nature*, 357, 563-569 (1992)) or Gαi2. A chimera containing the C-terminal 25 residues of gustducin (G$_{gust-25}$) proved particularly effective at mediating responses of mouse T1R2+3 and T1R1+3 in transient transfection assays, and was used for further studies. Cell lines stably expressing T1R3 and G$_{gust-25}$ were established using puromycin and Zeocin (Invitrogen) selection. Three independent lines expressing T1R3 and G$_{gust-25}$ were used to examine the specificity and dose response of the T1R3 receptor. Sucrose and maltose (>300 mM) elicited dose dependent responses that were T1R3 and G$_{gust-25}$ dependent, but attempts to use high concentrations of several other sugars (glucose, fructose, trehalose and galactose) proved impractical because they induced significant receptor independent rises in [Ca$^{2+}$]$_i$.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

The invention claimed is:

1. A method of identifying a compound that modulates taste signal transduction in taste cells, the method comprising the steps of:
   (i) contacting a test compound with an isolated taste receptor comprising at least one T1R3 polypeptide and not comprising T1R1 or T1R2, and wherein the T1R3 polypeptide is at least 90% identical to an amino acid sequence of SEQ ID NO: 15, 20, 23, 25, or 31;
   (ii) determining a functional effect of the test compound on the receptor, wherein said functional effect comprises binding to the receptor or having an effect on the activity of the receptor; and
   (iii) comparing the functional effect of the test compound to a functional effect of >300 mM natural sugar on said receptor, and identifying the test compound as a compound that modulates taste signal transduction if the effect of the test compound is equal to or greater than the effect of >300 mM natural sugar on said receptor.

2. The method of claim 1, wherein the taste receptor comprises a plurality of T1R3 polypeptides.

3. The method of claim 1, wherein the receptor is recombinant.

4. The method of claim 1, wherein the receptor comprises G protein coupled receptor activity.

5. The method of claim 1, wherein the functional effect is measured in vitro.

6. The method of claim 5, wherein the functional effect comprises a physical effect.

7. The method of claim 5, wherein the receptor is linked to a solid phase.

8. The method of claim 5, wherein the functional effect is determined by measuring binding of the compound to the receptor.

9. The method of claim 8, wherein the functional effect is determined by measuring binding of the compound to an extracellular domain of the receptor.

10. The method of claim 1, wherein the receptor is expressed in a cell or cell membrane, wherein the cell or cell membrane does not express T1R1 or T1R2.

11. The method of claim 10, wherein the functional effect comprises a physical effect.

12. The method of claim 11, wherein the functional effect is determined by measuring compound binding to the receptor.

13. The method of claim 12, wherein the functional effect is determined by measuring binding of the compound to an extracellular domain of the receptor.

14. The method of claim 10, wherein the functional effect comprises a chemical effect or a phenotypic effect.

15. The method of claim 14, wherein the functional effect is determined by measuring changes in intracellular cAMP, IP3, or Ca2+.

16. The method of claim 10, wherein the cell is a mammalian cell.

17. The method of claim 16, wherein the mammalian cell is a human cell.

18. The method of claim 16, wherein the mammalian cell is a mouse cell.

19. The method of claim 1, wherein the T1R3 polypeptide consists of the amino acid sequence of SEQ ID NO: 15.

20. The method of claim 1, wherein the T1R3 polypeptide consists of the amino acid sequence of SEQ ID NO: 20.

21. The method of claim 1, wherein the T1R3 polypeptide consists of the amino acid sequence of SEQ ID NO: 23.

22. The method of claim 1, wherein the T1R3 polypeptide consists of the amino acid sequence of SEQ ID NO: 25.

23. The method of claim 1, wherein the T1R3 polypeptide consists of the amino acid sequence of SEQ ID NO: 31.

24. A method of identifying a modulator of taste signal transduction in taste cells, the method comprising the steps of:

(i) contacting a cell or cell membrane with a candidate compound and a natural sugar, wherein the cell or cell membrane comprises a T1R3 polypeptide and does not express T1R1 and T1R2, and wherein the T1R3 polypeptide is at least 90% identical to an amino acid sequence of SEQ ID NO: 15, 20, 23, 25, or 31; and (ii) determining whether the candidate compound modulates an effect of the natural sugar on the receptor, thereby identifying the candidate compound as the modulator of taste signal transduction.

25. A method of identifying a compound that modulates taste signal transduction in taste cells, the method comprising the steps of:

(i) contacting a test compound with an isolated taste receptor comprising at least one T1R3 polypeptide and not comprising T1R1 or T1R2, and wherein the T1R3 polypeptide is at least 90% identical to an amino acid sequence of SEQ ID NO: 15, 20, 23, 25, or 31;

(ii) determining an effect of the test compound on the receptor, wherein said effect comprises binding to the receptor or altering the activity of the receptor; and (iii) comparing the effect of the test compound to an effect of a natural sweetener on said receptor, and identifying the test compound as a compound that modulates taste signal transduction if the effect of the test compound is equal to or greater than the effect of the natural sweetener on said receptor.

* * * * *